(12) United States Patent
Wykes

(10) Patent No.: US 11,725,041 B2
(45) Date of Patent: Aug. 15, 2023

(54) IMMUNE-MODULATING COMPOUNDS

(71) Applicant: The Council of the Queensland Institute of Medical Research, Herston (AU)

(72) Inventor: Michelle Wykes, Toowong (AU)

(73) Assignee: The Council of the Queensland Institute of Medical Research, Herson (AU)

( * ) Notice: Subject to any disclaimer, the term of this patent is extended or adjusted under 35 U.S.C. 154(b) by 609 days.

(21) Appl. No.: 16/324,857

(22) PCT Filed: Aug. 11, 2016

(86) PCT No.: PCT/AU2016/050726
§ 371 (c)(1),
(2) Date: Feb. 11, 2019

(87) PCT Pub. No.: WO2018/027252
PCT Pub. Date: Feb. 15, 2018

(65) Prior Publication Data
US 2019/0389929 A1    Dec. 26, 2019

(51) Int. Cl.
*C07K 14/705* (2006.01)
*A61K 38/00* (2006.01)
*C12N 15/62* (2006.01)
*A61P 35/00* (2006.01)
*A61P 31/00* (2006.01)
*A61P 37/02* (2006.01)
*A61P 35/04* (2006.01)

(52) U.S. Cl.
CPC ........ *C07K 14/70532* (2013.01); *A61P 35/04* (2018.01); *A61P 37/02* (2018.01); *A61K 38/00* (2013.01); *C07K 2319/30* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 2010/0285039 A1* | 11/2010 | Chen | A61P 35/00 424/174.1 |
| 2012/0065385 A1* | 3/2012 | Pardoll | A61P 31/00 536/23.5 |
| 2012/0114649 A1* | 5/2012 | Langermann | A61K 31/675 424/135.1 |
| 2012/0269859 A1 | 10/2012 | Minato et al. | |
| 2013/0017199 A1* | 1/2013 | Langermann | A61P 35/02 424/134.1 |
| 2015/0361155 A1* | 12/2015 | Tykocinski | C07K 14/525 514/17.9 |
| 2017/0058015 A1* | 3/2017 | Seidel, III | A61P 31/00 |
| 2019/0381184 A1* | 12/2019 | Huang | A61P 5/00 |

FOREIGN PATENT DOCUMENTS

| | | |
|---|---|---|
| EP | 1997887 | 9/2013 |
| JP | 2012-157357 | 8/2012 |
| WO | WO 2001/49866 | 7/2001 |
| WO | WO 2010/027827 | 3/2010 |
| WO | WO 2010/037402 | 4/2010 |
| WO | WO 2014/121085 | 8/2014 |
| WO | WO 2015/195531 | 12/2015 |
| WO | WO 2016/008005 | 1/2016 |
| WO | WO 2016/022994 | 2/2016 |
| WO | WO 2016/090347 | 6/2016 |

OTHER PUBLICATIONS

Arthos et al. (2002) The Journal of Biological Chemistry, vol. 277, No. 13, pp. 11456-11464.*
Edgar JDM, J. Clin. Pathol. (2008), 61: 988-993.*
Karunarathne et al., Programmed Death-1 Ligand 2-Mediated Regulation of the PD-L1 to PD-1 Axis Is Essential for Establishing CD4+ T Cell Immunity. Immunity. 2016;45:333-45.
Terawaki et al., Specific and high-affinity binding of tetramerized PD-L1 extracellular domain to PD-1-expressing cells: possible application to enhance T cell function. Intl Immunol 2007;19:881-890.
International Search Report and Written Opinion for PCT/AU2016/050726, dated Sep. 21, 2016, 10 pages.
Extended EP Search Report for EP16911787.6, dated Dec. 17, 2019, 7 pages.

* cited by examiner

*Primary Examiner* — Ilia I Ouspenski
(74) *Attorney, Agent, or Firm* — Casimir Jones, S.C.; Mary Ann D. Brow

(57) ABSTRACT

Disclosed are compounds for use in modulating immune responses. More particularly, the present invention discloses oligomeric forms of PD-L2 for use in modulating Th1 immune responses. The compounds of the present invention find utility in a range of Th1-mediated disorders including pathogenic infections and hyperproliferative disorders.

21 Claims, 14 Drawing Sheets
Specification includes a Sequence Listing.

SEQUENCE LISTING

```
<160> NUMBER OF SEQ ID NOS: 58

<210> SEQ ID NO 1
<211> LENGTH: 273
<212> TYPE: PRT
<213> ORGANISM: Homo sapiens

<400> SEQUENCE: 1

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
```

```
              245                 250                 255
Thr Thr Lys Arg Pro Val Thr Thr Lys Arg Glu Val Asn Ser Ala
            260                 265                 270
Ile

<210> SEQ ID NO 2
<211> LENGTH: 310
<212> TYPE: PRT
<213> ORGANISM: Pan troglodytes

<400> SEQUENCE: 2

Met Arg Trp Ala Lys Arg Ser Arg Tyr Glu Leu Arg Glu Arg Asp Ser
1               5                   10                  15

Met Asn His Glu Arg Trp Ala Lys Lys Ala Ala Ser Pro Glu Val Ser
            20                  25                  30

Asp Gln Ile Gln Asn Met Ile Phe Leu Leu Met Leu Ser Leu Glu
        35                  40                  45

Leu Gln Leu His Gln Ile Ala Ala Leu Phe Thr Val Thr Val Pro Lys
    50                  55                  60

Glu Leu Tyr Ile Ile Glu His Gly Ser Asn Val Thr Leu Glu Cys Asn
65                  70                  75                  80

Phe Asp Thr Gly Ser His Val Asn Leu Gly Ala Ile Thr Ala Ser Leu
                85                  90                  95

Gln Lys Val Glu Asn Asp Thr Ser Pro His Cys Glu Arg Ala Thr Leu
            100                 105                 110

Leu Glu Glu Gln Leu Pro Leu Gly Lys Ala Leu Phe His Ile Pro Gln
        115                 120                 125

Val Gln Val Arg Asp Glu Gly Gln Tyr Gln Cys Ile Ile Ile Tyr Gly
    130                 135                 140

Val Ala Trp Asp Tyr Lys Tyr Leu Thr Leu Lys Val Lys Ala Ser Tyr
145                 150                 155                 160

Arg Lys Ile Asn Thr His Ile Leu Lys Val Pro Glu Thr Asp Glu Val
                165                 170                 175

Glu Leu Thr Cys Gln Ala Thr Gly Tyr Pro Leu Ala Glu Val Ser Trp
            180                 185                 190

Pro Asn Val Ser Val Pro Ala Asn Thr Ser His Ser Arg Thr Pro Glu
        195                 200                 205

Gly Leu Tyr Gln Val Thr Ser Val Leu Arg Leu Lys Pro Pro Pro Gly
    210                 215                 220

Arg Asn Phe Ser Cys Val Phe Trp Asn Thr His Val Arg Glu Leu Thr
225                 230                 235                 240

Leu Ala Ser Ile Asp Leu Gln Ser Gln Met Glu Pro Arg Thr His Pro
                245                 250                 255

Thr Trp Leu Leu His Ile Phe Ile Pro Ser Cys Ile Ile Ala Phe Ile
            260                 265                 270

Phe Ile Ala Thr Val Ile Ala Leu Arg Lys Gln Leu Cys Gln Lys Leu
        275                 280                 285

Tyr Ser Ser Lys Asp Thr Thr Lys Arg Pro Val Thr Thr Thr Lys Arg
    290                 295                 300

Glu Val Asn Ser Ala Ile
305                 310

<210> SEQ ID NO 3
<211> LENGTH: 247
<212> TYPE: PRT
```

<213> ORGANISM: Mus musculus

<400> SEQUENCE: 3

Met Leu Leu Leu Leu Pro Ile Leu Asn Leu Ser Gln Leu His Pro
1               5                   10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
                35                  40                  45

Cys Thr Glu Leu Glu Gly Ile Arg Ala Ser Leu Gln Lys Val Glu Asn
50                  55                  60

Asp Thr Ser Leu Gln Ser Glu Arg Ala Thr Leu Glu Glu Gln Leu
65                  70                  75                  80

Pro Leu Gly Lys Ala Leu Phe His Ile Pro Ser Val Gln Val Arg Asp
                85                  90                  95

Ser Gly Gln Tyr Arg Cys Leu Val Ile Cys Gly Ala Ala Trp Asp Tyr
                100                 105                 110

Lys Tyr Leu Thr Val Lys Val Lys Ala Ser Tyr Met Arg Ile Asp Thr
                115                 120                 125

Arg Ile Leu Glu Val Pro Gly Thr Gly Glu Val Gln Leu Thr Cys Gln
130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
                180                 185                 190

Met Phe Trp Asn Ala His Met Lys Glu Leu Thr Ser Ala Ile Ile Asp
                195                 200                 205

Pro Leu Ser Arg Met Glu Pro Lys Val Pro Arg Thr Trp Pro Leu His
210                 215                 220

Val Phe Ile Pro Ala Cys Thr Ile Ala Leu Ile Phe Leu Ala Ile Val
225                 230                 235                 240

Ile Ile Gln Arg Lys Arg Ile
                245

<210> SEQ ID NO 4
<211> LENGTH: 220
<212> TYPE: PRT
<213> ORGANISM: Artificial
<220> FEATURE:
<223> OTHER INFORMATION: Human PD-L2 ectodomain plus signal peptide

<400> SEQUENCE: 4

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
                35                  40                  45

His Val Asn Leu Gly Ala Ile Thr Ala Ser Leu Gln Lys Val Glu Asn
                50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

```
Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr
    210                 215                 220
```

<210> SEQ ID NO 5
<211> LENGTH: 257
<212> TYPE: PRT
<213> ORGANISM: Artificial
<220> FEATURE:
<223> OTHER INFORMATION: Chimpanzee PD-L2 ectodomain plus signal peptide

<400> SEQUENCE: 5

```
Met Arg Trp Ala Lys Arg Ser Arg Tyr Glu Leu Arg Glu Arg Asp Ser
1               5                   10                  15

Met Asn His Glu Arg Trp Ala Lys Lys Ala Ala Ser Pro Glu Val Ser
                20                  25                  30

Asp Gln Ile Gln Asn Met Ile Phe Leu Leu Leu Met Leu Ser Leu Glu
            35                  40                  45

Leu Gln Leu His Gln Ile Ala Ala Leu Phe Thr Val Thr Val Pro Lys
        50                  55                  60

Glu Leu Tyr Ile Ile Glu His Gly Ser Asn Val Thr Leu Glu Cys Asn
65                  70                  75                  80

Phe Asp Thr Gly Ser His Val Asn Leu Gly Ala Ile Thr Ala Ser Leu
                85                  90                  95

Gln Lys Val Glu Asn Asp Thr Ser Pro His Cys Glu Arg Ala Thr Leu
                100                 105                 110

Leu Glu Glu Gln Leu Pro Leu Gly Lys Ala Leu Phe His Ile Pro Gln
            115                 120                 125

Val Gln Val Arg Asp Glu Gly Gln Tyr Gln Cys Ile Ile Ile Tyr Gly
        130                 135                 140

Val Ala Trp Asp Tyr Lys Tyr Leu Thr Leu Lys Val Lys Ala Ser Tyr
145                 150                 155                 160

Arg Lys Ile Asn Thr His Ile Leu Lys Val Pro Glu Thr Asp Glu Val
                165                 170                 175

Glu Leu Thr Cys Gln Ala Thr Gly Tyr Pro Leu Ala Glu Val Ser Trp
            180                 185                 190

Pro Asn Val Ser Val Pro Ala Asn Thr Ser His Ser Arg Thr Pro Glu
        195                 200                 205

Gly Leu Tyr Gln Val Thr Ser Val Leu Arg Leu Lys Pro Pro Gly
210                 215                 220

Arg Asn Phe Ser Cys Val Phe Trp Asn Thr His Val Arg Glu Leu Thr
225                 230                 235                 240
```

Leu Ala Ser Ile Asp Leu Gln Ser Gln Met Glu Pro Arg Thr His Pro
                245                 250                 255

Thr

<210> SEQ ID NO 6
<211> LENGTH: 220
<212> TYPE: PRT
<213> ORGANISM: Artificial
<220> FEATURE:
<223> OTHER INFORMATION: Mouse PD-L2 ectodomain plus signal peptide

<400> SEQUENCE: 6

Met Leu Leu Leu Leu Pro Ile Leu Asn Leu Ser Leu Gln Leu His Pro
1               5                   10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
        35                  40                  45

Cys Thr Glu Leu Glu Gly Ile Arg Ala Ser Leu Gln Lys Val Glu Asn
    50                  55                  60

Asp Thr Ser Leu Gln Ser Glu Arg Ala Thr Leu Leu Glu Glu Gln Leu
65                  70                  75                  80

Pro Leu Gly Lys Ala Leu Phe His Ile Pro Ser Val Gln Val Arg Asp
                85                  90                  95

Ser Gly Gln Tyr Arg Cys Leu Val Ile Cys Gly Ala Ala Trp Asp Tyr
            100                 105                 110

Lys Tyr Leu Thr Val Lys Val Lys Ala Ser Tyr Met Arg Ile Asp Thr
        115                 120                 125

Arg Ile Leu Glu Val Pro Gly Thr Gly Glu Val Gln Leu Thr Cys Gln
130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
            180                 185                 190

Met Phe Trp Asn Ala His Met Lys Glu Leu Thr Ser Ala Ile Ile Asp
        195                 200                 205

Pro Leu Ser Arg Met Glu Pro Lys Val Pro Arg Thr
210                 215                 220

<210> SEQ ID NO 7
<211> LENGTH: 201
<212> TYPE: PRT
<213> ORGANISM: Homo sapiens

<400> SEQUENCE: 7

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln

```
                65                  70                  75                  80
Tyr Gln Cys Ile Ile Ile Tyr Gly Val Ala Trp Asp Tyr Lys Tyr Leu
                    85                  90                  95
Thr Leu Lys Val Lys Ala Ser Tyr Arg Lys Ile Asn Thr His Ile Leu
                100                 105                 110
Lys Val Pro Glu Thr Asp Glu Val Glu Leu Thr Cys Gln Ala Thr Gly
                115                 120                 125
Tyr Pro Leu Ala Glu Val Ser Trp Pro Asn Val Ser Val Pro Ala Asn
            130                 135                 140
Thr Ser His Ser Arg Thr Pro Glu Gly Leu Tyr Gln Val Thr Ser Val
145                 150                 155                 160
Leu Arg Leu Lys Pro Pro Gly Arg Asn Phe Ser Cys Val Phe Trp
                165                 170                 175
Asn Thr His Val Arg Glu Leu Thr Leu Ala Ser Ile Asp Leu Gln Ser
                180                 185                 190
Gln Met Glu Pro Arg Thr His Pro Thr
                195                 200

<210> SEQ ID NO 8
<211> LENGTH: 201
<212> TYPE: PRT
<213> ORGANISM: Pan troglodytes

<400> SEQUENCE: 8

Leu Phe Thr Val Thr Val Pro Lys Glu Leu Tyr Ile Ile Glu His Gly
1               5                   10                  15
Ser Asn Val Thr Leu Glu Cys Asn Phe Asp Thr Gly Ser His Val Asn
                20                  25                  30
Leu Gly Ala Ile Thr Ala Ser Leu Gln Lys Val Glu Asn Asp Thr Ser
            35                  40                  45
Pro His Cys Glu Arg Ala Thr Leu Leu Glu Glu Gln Leu Pro Leu Gly
        50                  55                  60
Lys Ala Leu Phe His Ile Pro Gln Val Gln Val Arg Asp Glu Gly Gln
65                  70                  75                  80
Tyr Gln Cys Ile Ile Ile Tyr Gly Val Ala Trp Asp Tyr Lys Tyr Leu
                    85                  90                  95
Thr Leu Lys Val Lys Ala Ser Tyr Arg Lys Ile Asn Thr His Ile Leu
                100                 105                 110
Lys Val Pro Glu Thr Asp Glu Val Glu Leu Thr Cys Gln Ala Thr Gly
                115                 120                 125
Tyr Pro Leu Ala Glu Val Ser Trp Pro Asn Val Ser Val Pro Ala Asn
            130                 135                 140
Thr Ser His Ser Arg Thr Pro Glu Gly Leu Tyr Gln Val Thr Ser Val
145                 150                 155                 160
Leu Arg Leu Lys Pro Pro Gly Arg Asn Phe Ser Cys Val Phe Trp
                165                 170                 175
Asn Thr His Val Arg Glu Leu Thr Leu Ala Ser Ile Asp Leu Gln Ser
                180                 185                 190
Gln Met Glu Pro Arg Thr His Pro Thr
                195                 200

<210> SEQ ID NO 9
<211> LENGTH: 201
<212> TYPE: PRT
<213> ORGANISM: Mus musculus
```

<400> SEQUENCE: 9

```
Leu Phe Thr Val Thr Ala Pro Lys Glu Val Tyr Thr Val Asp Val Gly
1               5                   10                  15

Ser Ser Val Ser Leu Glu Cys Asp Phe Asp Arg Arg Glu Cys Thr Glu
            20                  25                  30

Leu Glu Gly Ile Arg Ala Ser Leu Gln Lys Val Glu Asn Asp Thr Ser
        35                  40                  45

Leu Gln Ser Glu Arg Ala Thr Leu Leu Glu Gln Leu Pro Leu Gly
    50                  55                  60

Lys Ala Leu Phe His Ile Pro Ser Val Gln Val Arg Asp Ser Gly Gln
65                  70                  75                  80

Tyr Arg Cys Leu Val Ile Cys Gly Ala Ala Trp Asp Tyr Lys Tyr Leu
                85                  90                  95

Thr Val Lys Val Lys Ala Ser Tyr Met Arg Ile Asp Thr Arg Ile Leu
            100                 105                 110

Glu Val Pro Gly Thr Gly Glu Val Gln Leu Thr Cys Gln Ala Arg Gly
        115                 120                 125

Tyr Pro Leu Ala Glu Val Ser Trp Gln Asn Val Ser Val Pro Ala Asn
    130                 135                 140

Thr Ser His Ile Arg Thr Pro Glu Gly Leu Tyr Gln Val Thr Ser Val
145                 150                 155                 160

Leu Arg Leu Lys Pro Gln Pro Ser Arg Asn Phe Ser Cys Met Phe Trp
                165                 170                 175

Asn Ala His Met Lys Glu Leu Thr Ser Ala Ile Ile Asp Pro Leu Ser
            180                 185                 190

Arg Met Glu Pro Lys Val Pro Arg Thr
        195                 200
```

<210> SEQ ID NO 10
<211> LENGTH: 330
<212> TYPE: PRT
<213> ORGANISM: Homo sapiens

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
        260                 265                 270
Asn Tyr Lys Thr Thr Pro Pro Val Leu Asp Ser Asp Gly Ser Phe Phe
    275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 11
<211> LENGTH: 326
<212> TYPE: PRT
<213> ORGANISM: Homo sapiens

<400> SEQUENCE: 11

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
            85                  90                  95
Thr Val Glu Arg Lys Cys Cys Val Glu Cys Pro Pro Cys Pro Ala Pro
        100                 105                 110
Pro Val Ala Gly Pro Ser Val Phe Leu Phe Pro Pro Lys Pro Lys Asp
    115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
            165                 170                 175
Ser Thr Phe Arg Val Val Ser Val Leu Thr Val Val His Gln Asp Trp
        180                 185                 190
Leu Asn Gly Lys Glu Tyr Lys Cys Lys Val Ser Asn Lys Gly Leu Pro
    195                 200                 205
```

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 12
<211> LENGTH: 377
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
```

```
                        245                 250                 255
Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 14
<211> LENGTH: 231
<212> TYPE: PRT
<213> ORGANISM: Homo sapiens

<400> SEQUENCE: 14

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 15
<211> LENGTH: 223
<212> TYPE: PRT
<213> ORGANISM: Homo sapiens

<400> SEQUENCE: 15
```

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
            130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Pro Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
    210                 215                 220

<210> SEQ ID NO 16
<211> LENGTH: 227
<212> TYPE: PRT
<213> ORGANISM: Homo sapiens

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                  170                  175

Val Leu Asp Ser Asp Gly Ser Phe Phe Leu Tyr Ser Lys Leu Thr Val
            180                  185                  190

Asp Lys Ser Arg Trp Gln Gln Gly Asn Val Phe Ser Cys Ser Val Met
          195                  200                  205

His Glu Ala Leu His Asn His Tyr Thr Gln Lys Ser Leu Ser Leu Ser
          210                  215                  220

Pro Gly Lys
225

<210> SEQ ID NO 17
<211> LENGTH: 39
<212> TYPE: PRT
<213> ORGANISM: Homo sapiens

<400> SEQUENCE: 17

Arg Ile Ala Arg Leu Glu Glu Lys Val Lys Thr Leu Lys Ala Gln Asn
1                 5                 10                15

Ser Glu Leu Ala Ser Thr Ala Asn Met Leu Arg Glu Gln Val Ala Gln
          20                  25                  30

Leu Lys Gln Lys Val Met Asn
          35

<210> SEQ ID NO 18
<211> LENGTH: 39
<212> TYPE: PRT
<213> ORGANISM: Homo sapiens

<400> SEQUENCE: 18

Leu Thr Asp Thr Leu Gln Ala Glu Thr Asp Gln Leu Glu Asp Glu Lys
1                 5                 10                15

Ser Ala Leu Gln Thr Glu Ile Ala Asn Leu Leu Lys Glu Lys Glu Lys
          20                  25                  30

Leu Glu Phe Ile Leu Ala Ala
          35

<210> SEQ ID NO 19
<211> LENGTH: 32
<212> TYPE: PRT
<213> ORGANISM: Homo sapiens

<400> SEQUENCE: 19

Arg Met Lys Gln Leu Glu Asp Lys Val Glu Glu Leu Leu Ser Lys Asn
1                 5                 10                15

Tyr His Leu Glu Asn Glu Val Ala Arg Leu Lys Lys Leu Val Gly Glu
          20                  25                  30

<210> SEQ ID NO 20
<211> LENGTH: 32
<212> TYPE: PRT
<213> ORGANISM: Homo sapiens

<400> SEQUENCE: 20

Met Lys Gln Leu Glu Asp Lys Val Glu Glu Leu Leu Ser Lys Asn Tyr
1                 5                 10                15

His Leu Glu Asn Glu Val Ala Arg Leu Lys Lys Leu Val Gly Glu Arg
          20                  25                  30

<210> SEQ ID NO 21
<211> LENGTH: 32
<212> TYPE: PRT
<213> ORGANISM: Homo sapiens

<400> SEQUENCE: 21

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

<210> SEQ ID NO 22
<211> LENGTH: 27
<212> TYPE: PRT
<213> ORGANISM: Homo sapiens

<400> SEQUENCE: 22

Met Lys Gln Ile Glu Asp Lys Ile Glu Glu Ile Glu Ser Lys Gln Lys
1               5                   10                  15

Lys Ile Glu Asn Glu Ile Ala Arg Ile Lys Lys
            20                  25

<210> SEQ ID NO 23
<211> LENGTH: 32
<212> TYPE: PRT
<213> ORGANISM: Homo sapiens

<400> SEQUENCE: 23

Arg Met Lys Gln Ile Glu Asp Lys Leu Glu Glu Ile Leu Ser Lys Leu
1               5                   10                  15

Tyr His Ile Glu Asn Glu Leu Ala Arg Ile Lys Lys Leu Leu Gly Glu
            20                  25                  30

<210> SEQ ID NO 24
<211> LENGTH: 31
<212> TYPE: PRT
<213> ORGANISM: Homo sapiens

<400> SEQUENCE: 24

Met Lys Gln Ile Glu Asp Lys Leu Glu Glu Ile Leu Ser Lys Leu Tyr
1               5                   10                  15

His Ile Glu Asn Glu Leu Ala Arg Ile Lys Lys Leu Leu Gly Glu
            20                  25                  30

<210> SEQ ID NO 25
<211> LENGTH: 27
<212> TYPE: PRT
<213> ORGANISM: Bacteriophage T4

<400> SEQUENCE: 25

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 26
<211> LENGTH: 29
<212> TYPE: PRT
<213> ORGANISM: Bacteriophage T4

<400> SEQUENCE: 26

Gly Ser Gly Tyr Ile Pro Glu Ala Pro Arg Asp Gly Gln Ala Tyr Val
1               5                   10                  15

-continued

Arg Lys Asp Gly Glu Trp Val Leu Leu Ser Thr Phe Leu
            20                  25

<210> SEQ ID NO 27
<211> LENGTH: 49
<212> TYPE: PRT
<213> ORGANISM: Staphylothermus marinus

<400> SEQUENCE: 27

Ile Ile Asn Glu Thr Ala Asp Asp Ile Val Tyr Arg Leu Thr Val Ile
1               5                   10                  15

Ile Asp Asp Arg Tyr Glu Ser Leu Lys Asn Leu Ile Thr Leu Arg Ala
            20                  25                  30

Asp Arg Leu Met Ile Ile Asn Asp Asn Val Ser Thr Ile Leu Ala Ser
        35                  40                  45

Gly

<210> SEQ ID NO 28
<211> LENGTH: 44
<212> TYPE: PRT
<213> ORGANISM: Homo sapiens

<400> SEQUENCE: 28

Leu Ala Pro Gln Met Leu Arg Glu Leu Gln Glu Thr Asn Ala Ala Leu
1               5                   10                  15

Gln Asp Val Arg Glu Leu Leu Arg Gln Gln Val Lys Gln Ile Thr Phe
            20                  25                  30

Leu Lys Asn Thr Val Met Glu Cys Asp Ala Cys Gly
        35                  40

<210> SEQ ID NO 29
<211> LENGTH: 53
<212> TYPE: PRT
<213> ORGANISM: Homo sapiens

<400> SEQUENCE: 29

Ser Ser Asn Ala Lys Trp Asp Gln Trp Ser Ser Asp Trp Gln Thr Trp
1               5                   10                  15

Asn Ala Lys Trp Asp Gln Trp Ser Asn Asp Trp Asn Ala Trp Arg Ser
            20                  25                  30

Asp Trp Gln Ala Trp Lys Asp Asp Trp Ala Arg Trp Asn Gln Arg Trp
        35                  40                  45

Asp Asn Trp Ala Thr
        50

<210> SEQ ID NO 30
<211> LENGTH: 18
<212> TYPE: PRT
<213> ORGANISM: Homo sapiens

<400> SEQUENCE: 30

Pro Thr His Val Asn Val Ser Val Val Met Ala Glu Val Asp Gly Thr
1               5                   10                  15

Cys Tyr

<210> SEQ ID NO 31
<211> LENGTH: 44
<212> TYPE: PRT
<213> ORGANISM: Homo sapiens

```
<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 32
<211> LENGTH: 16
<212> TYPE: PRT
<213> ORGANISM: Homo sapiens

<400> SEQUENCE: 32

Gln Ile Glu Tyr Leu Ala Lys Gln Ile Val Asp Asn Ala Ile Gln Gln
1               5                   10                  15

<210> SEQ ID NO 33
<211> LENGTH: 45
<212> TYPE: PRT
<213> ORGANISM: Homo sapiens

<400> SEQUENCE: 33

Cys Ser His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 34
<211> LENGTH: 21
<212> TYPE: PRT
<213> ORGANISM: Homo sapiens

<400> SEQUENCE: 34

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 35
<211> LENGTH: 5
<212> TYPE: PRT
<213> ORGANISM: Artificial
<220> FEATURE:
<223> OTHER INFORMATION: Linker

<400> SEQUENCE: 35

Gly Gly Gly Gly Gly
1               5

<210> SEQ ID NO 36
<211> LENGTH: 5
<212> TYPE: PRT
<213> ORGANISM: Artificial
<220> FEATURE:
<223> OTHER INFORMATION: Linker

<400> SEQUENCE: 36

Gly Gly Gly Gly Ser
1               5
```

<210> SEQ ID NO 37
<211> LENGTH: 5
<212> TYPE: PRT
<213> ORGANISM: Artificial
<220> FEATURE:
<223> OTHER INFORMATION: Linker

<400> SEQUENCE: 37

Ser Ser Ser Ser Gly
1               5

<210> SEQ ID NO 38
<211> LENGTH: 12
<212> TYPE: PRT
<213> ORGANISM: Artificial
<220> FEATURE:
<223> OTHER INFORMATION: Linker

<400> SEQUENCE: 38

Gly Lys Ser Ser Gly Ser Gly Ser Glu Ser Lys Ser
1               5                   10

<210> SEQ ID NO 39
<211> LENGTH: 19
<212> TYPE: PRT
<213> ORGANISM: Artificial
<220> FEATURE:
<223> OTHER INFORMATION: Linker

<400> SEQUENCE: 39

Gly Ser Thr Ser Gly Ser Gly Lys Ser Ser Glu Gly Ser Gly Ser
1               5                   10                  15

Thr Lys Gly

<210> SEQ ID NO 40
<211> LENGTH: 18
<212> TYPE: PRT
<213> ORGANISM: Artificial
<220> FEATURE:
<223> OTHER INFORMATION: Linker

<400> SEQUENCE: 40

Gly Ser Thr Ser Gly Ser Gly Lys Pro Gly Ser Gly Glu Gly Ser Thr
1               5                   10                  15

Lys Gly

<210> SEQ ID NO 41
<211> LENGTH: 14
<212> TYPE: PRT
<213> ORGANISM: Artificial
<220> FEATURE:
<223> OTHER INFORMATION: Linker

<400> SEQUENCE: 41

Glu Gly Lys Ser Ser Gly Ser Gly Ser Glu Ser Lys Glu Phe
1               5                   10

<210> SEQ ID NO 42
<211> LENGTH: 14
<212> TYPE: PRT
<213> ORGANISM: Artificial
<220> FEATURE:
<223> OTHER INFORMATION: Linker

<400> SEQUENCE: 42

Glu Gly Lys Ser Ser Gly Ser Gly Ser Glu Ser Lys Glu Phe
1               5                   10

<210> SEQ ID NO 43
<211> LENGTH: 4
<212> TYPE: PRT
<213> ORGANISM: Artificial
<220> FEATURE:
<223> OTHER INFORMATION: Linker

<400> SEQUENCE: 43

Ala Ala Pro Ala
1

<210> SEQ ID NO 44
<211> LENGTH: 252
<212> TYPE: PRT
<213> ORGANISM: Artificial
<220> FEATURE:
<223> OTHER INFORMATION: Human PD-L2 ectodomain-L-GCN4 trimerization
      domain
<220> FEATURE:
<221> NAME/KEY: MISC_FEATURE
<222> LOCATION: (220)..(221)
<223> OTHER INFORMATION: a bond (e.g., peptide bond) or a peptide linker

<400> SEQUENCE: 44

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Arg Met Lys Gln
210                 215                 220

Ile Glu Asp Lys Ile Glu Glu Ile Leu Ser Lys Ile Tyr His Ile Glu
225                 230                 235                 240

Asn Glu Ile Ala Arg Ile Lys Lys Leu Ile Gly Glu
                245                 250

```
<210> SEQ ID NO 45
<211> LENGTH: 249
<212> TYPE: PRT
<213> ORGANISM: Artificial
<220> FEATURE:
<223> OTHER INFORMATION: Human PD-L2 ectodomain-L-foldon trimerization
      domain
<220> FEATURE:
<221> NAME/KEY: MISC_FEATURE
<222> LOCATION: (220)..(221)
<223> OTHER INFORMATION: a bond (e.g., peptide bond) or a peptide linker

<400> SEQUENCE: 45
```

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Gly Ser Gly Tyr
    210                 215                 220

Ile Pro Glu Ala Pro Arg Asp Gly Gln Ala Tyr Val Arg Lys Asp Gly
225                 230                 235                 240

Glu Trp Val Leu Leu Ser Thr Phe Leu
                245

```
<210> SEQ ID NO 46
<211> LENGTH: 252
<212> TYPE: PRT
<213> ORGANISM: Artificial
<220> FEATURE:
<223> OTHER INFORMATION: Human PD-L2 ectodomain-L-GCN4 tetramerization
      domain
<220> FEATURE:
<221> NAME/KEY: MISC_FEATURE
<222> LOCATION: (220)..(221)
<223> OTHER INFORMATION: a bond (e.g., peptide bond) or a peptide linker

<400> SEQUENCE: 46
```

Met Ile Phe Leu Leu Leu Met Leu Ser Leu Glu Leu Gln Leu His Gln

```
            1               5                  10                 15
Ile Ala Ala Leu Phe Thr Val Thr Val Pro Lys Glu Leu Tyr Ile Ile
                    20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
     50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                    85                  90                  95

Glu Gly Gln Tyr Gln Cys Ile Ile Tyr Gly Val Ala Trp Asp Tyr
            100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
     130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Arg Met Lys Gln
     210                 215                 220

Ile Glu Asp Lys Leu Glu Glu Ile Leu Ser Lys Leu Tyr His Ile Glu
225                 230                 235                 240

Asn Glu Leu Ala Arg Ile Lys Lys Leu Leu Gly Glu
                245                 250

<210> SEQ ID NO 47
<211> LENGTH: 269
<212> TYPE: PRT
<213> ORGANISM: Artificial
<220> FEATURE:
<223> OTHER INFORMATION: Human PD-L2 ectodomain-L-tetrabrachion
      tetramerization domain
<220> FEATURE:
<221> NAME/KEY: MISC_FEATURE
<222> LOCATION: (220)..(221)
<223> OTHER INFORMATION: a bond (e.g., peptide bond) or a peptide linker

<400> SEQUENCE: 47

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                    20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
     50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                    85                  90                  95
```

```
Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Ile Ile Asn Glu
    210                 215                 220

Thr Ala Asp Asp Ile Val Tyr Arg Leu Thr Val Ile Ile Asp Asp Arg
225                 230                 235                 240

Tyr Glu Ser Leu Lys Asn Leu Ile Thr Leu Arg Ala Asp Arg Leu Met
                245                 250                 255

Ile Ile Asn Asp Asn Val Ser Thr Ile Leu Ala Ser Gly
            260                 265
```

<210> SEQ ID NO 48
<211> LENGTH: 264
<212> TYPE: PRT
<213> ORGANISM: Artificial
<220> FEATURE:
<223> OTHER INFORMATION: Human PD-L2 ectodomain-L-COMP pentamerization
      domain
<220> FEATURE:
<221> NAME/KEY: MISC_FEATURE
<222> LOCATION: (220)..(221)
<223> OTHER INFORMATION: a bond (e.g., peptide bond) or a peptide linker

<400> SEQUENCE: 48

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160
```

```
Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Leu Ala Pro Gln
            210                 215                 220

Met Leu Arg Glu Leu Gln Glu Thr Asn Ala Ala Leu Gln Asp Val Arg
225                 230                 235                 240

Glu Leu Leu Arg Gln Gln Val Lys Gln Ile Thr Phe Leu Lys Asn Thr
                245                 250                 255

Val Met Glu Cys Asp Ala Cys Gly
                260

<210> SEQ ID NO 49
<211> LENGTH: 273
<212> TYPE: PRT
<213> ORGANISM: Artificial
<220> FEATURE:
<223> OTHER INFORMATION: Human PD-L2 ectodomain-L- tryptophane zipper
      pentamerization domain
<220> FEATURE:
<221> NAME/KEY: MISC_FEATURE
<222> LOCATION: (220)..(221)
<223> OTHER INFORMATION: a bond (e.g., peptide bond) or a peptide linker

<400> SEQUENCE: 49

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
        130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Ser Ser Asn Ala
            210                 215                 220

Lys Trp Asp Gln Trp Ser Ser Asp Trp Gln Thr Trp Asn Ala Lys Trp
```

```
                225                 230                 235                 240
Asp Gln Trp Ser Asn Asp Trp Asn Ala Trp Arg Ser Asp Trp Gln Ala
                    245                 250                 255
Trp Lys Asp Asp Trp Ala Arg Trp Asn Gln Arg Trp Asp Asn Trp Ala
                    260                 265                 270
Thr

<210> SEQ ID NO 50
<211> LENGTH: 238
<212> TYPE: PRT
<213> ORGANISM: Artificial
<220> FEATURE:
<223> OTHER INFORMATION: Human PD-L2 ectodomain-L-?tp hexamerization
      domain
<220> FEATURE:
<221> NAME/KEY: MISC_FEATURE
<222> LOCATION: (220)..(221)
<223> OTHER INFORMATION: a bond (e.g., peptide bond) or a peptide linker

<400> SEQUENCE: 50

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
        130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Pro His Val
    210                 215                 220

Asn Val Ser Val Val Met Ala Glu Val Asp Gly Thr Cys Tyr
225                 230                 235

<210> SEQ ID NO 51
<211> LENGTH: 476
<212> TYPE: PRT
<213> ORGANISM: Artificial
<220> FEATURE:
<223> OTHER INFORMATION: Human PD-L2 ectodomain-L-Fc dimerization
      domain-L-foldon trimerization domain
<220> FEATURE:
```

<220> FEATURE:
<221> NAME/KEY: MISC_FEATURE
<222> LOCATION: (220)..(221)
<223> OTHER INFORMATION: a bond (e.g., peptide bond) or a peptide linker
<220> FEATURE:
<221> NAME/KEY: MISC_FEATURE
<222> LOCATION: (448)..(449)
<223> OTHER INFORMATION: a bond (e.g., peptide bond) or a peptide linker

<400> SEQUENCE: 51

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
                435                 440                 445

Ser Gly Tyr Ile Pro Glu Ala Pro Arg Asp Gly Gln Ala Tyr Val Arg
450                 455                 460

Lys Asp Gly Glu Trp Val Leu Leu Ser Thr Phe Leu
465                 470                 475

<210> SEQ ID NO 52
<211> LENGTH: 478
<212> TYPE: PRT
<213> ORGANISM: Artificial
<220> FEATURE:
<223> OTHER INFORMATION: Human PD-L2 ectodomain-L-Fc dimerization
      domain-L-GCN4 tetramerization domain
<220> FEATURE:
<221> NAME/KEY: MISC_FEATURE
<222> LOCATION: (220)..(221)
<223> OTHER INFORMATION: a bond (e.g., peptide bond) or a peptide linker
<220> FEATURE:
<221> NAME/KEY: MISC_FEATURE
<222> LOCATION: (448)..(449)
<223> OTHER INFORMATION: a bond (e.g., peptide bond) or a peptide linker

<400> SEQUENCE: 52

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
                115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
                180                 185                 190

Val Phe Trp Asn Thr His Val Arg Glu Leu Thr Leu Ala Ser Ile Asp
                195                 200                 205
```

Leu Gln Ser Gln Met Glu Pro Arg Thr His Pro Thr Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Met
        435                 440                 445

Lys Gln Ile Glu Asp Lys Leu Glu Glu Ile Leu Ser Lys Leu Tyr His
    450                 455                 460

Ile Glu Asn Glu Leu Ala Arg Ile Lys Lys Leu Leu Gly Glu
465                 470                 475

<210> SEQ ID NO 53
<211> LENGTH: 491
<212> TYPE: PRT
<213> ORGANISM: Artificial
<220> FEATURE:
<223> OTHER INFORMATION: Human PD-L2 ectodomain-L-Fc dimerization
      domain-L-COMP pentamerization domain
<220> FEATURE:
<221> NAME/KEY: MISC_FEATURE
<222> LOCATION: (220)..(221)
<223> OTHER INFORMATION: a bond (e.g., peptide bond) or a peptide linker
<220> FEATURE:
<221> NAME/KEY: MISC_FEATURE
<222> LOCATION: (448)..(449)
<223> OTHER INFORMATION: a bond (e.g., peptide bond) or a peptide linker

<400> SEQUENCE: 53

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Tyr Gly Val Ala Trp Asp Tyr
                100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Leu
        435                 440                 445

Ala Pro Gln Met Leu Arg Glu Leu Gln Glu Thr Asn Ala Ala Leu Gln
    450                 455                 460

Asp Val Arg Glu Leu Leu Arg Gln Gln Val Lys Gln Ile Thr Phe Leu

```
                465                 470                 475                 480
Lys Asn Thr Val Met Glu Cys Asp Ala Cys Gly
                    485                 490

<210> SEQ ID NO 54
<211> LENGTH: 465
<212> TYPE: PRT
<213> ORGANISM: Artificial
<220> FEATURE:
<223> OTHER INFORMATION: Human PD-L2 ectodomain-L-Fc dimerization
      domain-L-?tp hexamerization domain
<220> FEATURE:
<221> NAME/KEY: MISC_FEATURE
<222> LOCATION: (220)..(221)
<223> OTHER INFORMATION: a bond (e.g., peptide bond) or a peptide linker
<220> FEATURE:
<221> NAME/KEY: MISC_FEATURE
<222> LOCATION: (448)..(449)
<223> OTHER INFORMATION: a bond (e.g., peptide bond) or a peptide linker

<400> SEQUENCE: 54

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
```

```
                290               295               300
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Pro
        435                 440                 445

Thr His Val Asn Val Ser Val Val Met Ala Glu Val Asp Gly Thr Cys
    450                 455                 460

Tyr
465

<210> SEQ ID NO 55
<211> LENGTH: 1518
<212> TYPE: DNA
<213> ORGANISM: Homo sapiens

<400> SEQUENCE: 55
acgcggggtt tttcttctct tgaatatatc ttaacgccaa attttgagtg cttttttgt      60 tacccatcct catatgtccc agctagaaag aatcctgggt tggagctact gcatgttgat    120
tgttttgttt ttccttttgg ctgttcattt tggtggctac tataaggaaa tctaacacaa    180
acagcaactg ttttttgttg tttacttttg catcttact tgtggagctg tggcaagtcc     240
tcatatcaaa tacagaacat gatcttcctc ctgctaatgt tgagcctgga attgcagctt    300
caccagatag cagcttttatt cacagtgaca gtccctaagg aactgtacat aatagagcat   360
ggcagcaatg tgaccctgga atgcaacttt gacactggaa gtcatgtgaa ccttggagca    420
ataacagcca gtttgcaaaa ggtggaaaat gatacatccc cacaccgtga agagccact     480 ttgctggagg agcagctgcc cctagggaag gcctcgttcc acatacctca gtccaagtg     540 agggacgaag gacagtacca atgcataatc atctatgggg tcgcctggga ctacaagtac    600
ctgactctga aagtcaaagc ttcctacagg aaaataaaca ctcacatcct aaaggttcca    660
gaaacagatg aggtagagct cacctgccag gctacaggtt atcctctggc agaagtatcc    720
tggccaaacg tcagcgttcc tgccaacacc agccactcca ggaccctga aggcctctac     780 caggtcacca gtgttctgcg cctaaagcca ccccctggca gaaacttcag ctgtgtgttc    840
tggaatactc acgtgaggga acttactttg gccagcattg accttcaaag tcagatggaa    900
cccaggaccc atccaacttg gctgcttcac attttcatcc cctcctgcat cattgctttc    960 atttcatag ccacagtgat agccctaaga aaacaactct gtcaaaagct gtattcttca    1020
aaagacacaa caaaaagacc tgtcaccaca acaaagaggg aagtgaacag tgctatctga  1080
```

-continued

```
acctgtggtc ttgggagcca gggtgacctg atatgacatc taaagaagct tctggactct    1140
gaacaagaat tcggtggcct gcagagcttg ccatttgcac ttttcaaatg cctttggatg    1200
acccagcact ttaatctgaa acctgcaaca agactagcca cacctggcc atgaaacttg     1260 cccttcact gatctggact cacctctgga gcctatggct ttaagcaagc actactgcac     1320
tttacagaat taccccactg gatcctggac ccacagaatt ccttcaggat ccttcttgct    1380
gccagactga aagcaaaagg aattatttcc cctcaagttt tctaagtgat ttccaaaagc    1440
agaggtgtgt ggaaatttcc agtaacagaa acagatgggt tgcaatagag ttattttta    1500 tctatagctt cctctggg                                                  1518
```

<210> SEQ ID NO 56
<211> LENGTH: 290
<212> TYPE: PRT
<213> ORGANISM: Homo sapiens

<400> SEQUENCE: 56

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
```

-continued

290

<210> SEQ ID NO 57
<211> LENGTH: 873
<212> TYPE: DNA
<213> ORGANISM: Homo sapiens

<400> SEQUENCE: 57

| | | | | | |
|---|---|---|---|---|---|
| atgaggatat | ttgctgtctt | tatattcatg | acctactggc | atttgctgaa | cgcatttact | 60 |
| gtcacggttc | ccaaggacct | atatgtggta | gagtatggta | gcaatatgac | aattgaatgc | 120 |
| aaattcccag | tagaaaaaca | attagacctg | gctgcactaa | ttgtctattg | ggaaatggag | 180 |
| gataagaaca | ttattcaatt | tgtgcatgga | gaggaagacc | tgaaggttca | gcatagtagc | 240 |
| tacagacaga | gggcccggct | gttgaaggac | cagctctccc | tgggaaatgc | tgcacttcag | 300 |
| atcacagatg | tgaaattgca | ggatgcaggg | gtgtaccgct | gcatgatcag | ctatggtggt | 360 |
| gccgactaca | agcgaattac | tgtgaaagtc | aatgccccat | acaacaaaat | caaccaaaga | 420 |
| attttggttg | tggatccagt | cacctctgaa | catgaactga | catgtcaggc | tgagggctac | 480 |
| cccaaggccg | aagtcatctg | gacaagcagt | gaccatcaag | tcctgagtgg | taagaccacc | 540 |
| accaccaatt | ccaagagaga | ggagaagctt | ttcaatgtga | ccagcacact | gagaatcaac | 600 |
| acaacaacta | atgagatttt | ctactgcact | tttaggagat | tagatcctga | ggaaaaccat | 660 |
| acagctgaat | tggtcatccc | agaactacct | ctggcacatc | ctccaaatga | aggactcac | 720 |
| ttggtaattc | tgggagccat | cttattatgc | cttggtgtag | cactgacatt | catcttccgt | 780 |
| ttaagaaaag | ggagaatgat | ggatgtgaaa | aaatgtggca | tccaagatac | aaactcaaag | 840 |
| aagcaaagtg | atacacattt | ggaggagacg | taa | | | 873 |

<210> SEQ ID NO 58
<211> LENGTH: 475
<212> TYPE: PRT
<213> ORGANISM: Artificial
<220> FEATURE:
<223> OTHER INFORMATION: Dodecameric PD-L2

<400> SEQUENCE: 58

Met Leu Leu Leu Leu Pro Ile Leu Asn Leu Ser Gln Leu His Pro
1               5                   10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
        35                  40                  45

Cys Thr Glu Leu Glu Gly Ile Arg Ala Ser Leu Gln Lys Val Glu Asn
    50                  55                  60

Asp Thr Ser Leu Gln Ser Glu Arg Ala Thr Leu Leu Glu Glu Gln Leu
65                  70                  75                  80

Pro Leu Gly Lys Ala Leu Phe His Ile Pro Ser Val Gln Val Arg Asp
                85                  90                  95

Ser Gly Gln Tyr Arg Cys Leu Val Ile Cys Gly Ala Ala Trp Asp Tyr
            100                 105                 110

Lys Tyr Leu Thr Val Lys Val Lys Ala Ser Tyr Met Arg Ile Asp Thr
        115                 120                 125

Arg Ile Leu Glu Val Pro Gly Thr Gly Glu Val Gln Leu Thr Cys Gln
    130                 135                 140

Ala Arg Gly Tyr Pro Leu Ala Glu Val Ser Trp Gln Asn Val Ser Val
145                 150                 155                 160

-continued

```
Pro Ala Asn Thr Ser His Ile Arg Thr Pro Glu Gly Leu Tyr Gln Val
            165                 170                 175
Thr Ser Val Leu Arg Leu Lys Pro Gln Pro Ser Arg Asn Phe Ser Cys
            180                 185                 190
Met Phe Trp Asn Ala His Met Lys Glu Leu Thr Ser Ala Ile Ile Asp
            195                 200                 205
Pro Leu Ser Arg Met Glu Pro Lys Val Pro Arg Thr Trp Pro Leu His
            210                 215                 220
Val Phe Ile Pro Ala Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
            245                 250                 255
Pro Lys Asp Thr Leu Met Ile Ser Arg Thr Pro Glu Val Thr Cys Val
            260                 265                 270
Val Val Asp Val Ser His Glu Asp Pro Glu Val Lys Phe Asn Trp Tyr
            275                 280                 285
Val Asp Gly Val Glu Val His Asn Ala Lys Thr Lys Pro Arg Glu Glu
290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
            325                 330                 335
Ala Leu Pro Ala Pro Ile Glu Lys Thr Ile Ser Lys Ala Lys Gly Gln
            340                 345                 350
Pro Arg Glu Pro Gln Val Tyr Thr Leu Pro Pro Ser Arg Glu Glu Met
            355                 360                 365
Thr Lys Asn Gln Val Ser Leu Thr Cys Leu Val Lys Gly Phe Tyr Pro
            370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
            405                 410                 415
Tyr Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
            435                 440                 445
Lys Ser Leu Ser Leu Ser Pro Gly Lys Pro Thr His Val Asn Val Ser
450                 455                 460
Val Val Met Ala Glu Val Asp Gly Thr Cys Tyr
465                 470                 475
```

IMMUNE-MODULATING COMPOUNDS

SEQUENCE LISTING

The text of the computer readable sequence listing filed herewith, titled "37555-251_SEQUENCE_LISTING_ST25", created Aug. 28, 2019, having a file size of 89,000 bytes, is hereby incorporated by reference in its entirety.

FIELD OF THE INVENTION

This invention relates generally to compounds for use in modulating immune responses. More particularly, the present invention relates to oligomeric forms of PD-L2 for use in modulating Th1 immune responses. The compounds of the present invention find utility in a range of Th1-mediated disorders including pathogenic infections and hyperproliferative disorders.

BACKGROUND OF THE INVENTION

Programmed cell death protein 1 (PD-1) is recognized as an important player in immune regulation, through its actions as a brake on effector T cells and in reducing immune responses in the tissue microenvironment. PD-1 is expressed on activated T cells including immunosuppressive CD4+ T cells (Treg) and exhausted CD8+ T cells, but also on B cells, myeloid dendritic cells (MDCs), monocytes, thymocytes, and natural killer (NK) cells. This broad PD-1 expression suggests a wide implication of the PD-1 signaling pathway needed for effective immunity and maintenance of T cell homeostasis (Gianchecchi et al., *Autoimmun. Rev.* 12:1091-100, 2013).

Significantly, the PD-1 signaling pathway contributes to the maintenance of both central and peripheral tolerance in normal individuals. In the thymus, the interaction of PD-1 and its ligands suppresses positive selection thereby inhibiting the transformation of CD4− CD8− double negative cells to CD4+ CD8+ double positive T cells (Keir et al., *J. Immunol.* 175:7329-7379, 2005). PD-1 signaling is also responsible for inhibition of self-reactive and inflammatory effector T cells that escape negative selection to avoid collateral immune-mediated tissue damage (Keir et al., *J. Exp. Med.* 203:883-895, 2006).

PD-1 has two known ligands: protein death ligand 1 (PD-L1; Freeman et al., *J. Exp. Med.* 192:1027-34, 2000), also known as B7-H1 in humans (Dong et al., *Nat. Med.* 5:1365-9, 1999), and protein death ligand 2 (PD-L2; Latchman et al., *Nat. Immunol.* 2:261-8, 2001), also known as B7-DC (Tseng et al., *J. Exp. Med.* 193:839-46, 2001). The patterns of expression of PD-L1 and PD-L2 are quite distinct. PD-L1 is expressed constitutively by a wide variety of immune cells and non-immune cells and appears to be upregulated in most normal tissue cells in the presence of strong inflammatory signals (Matzinger et al., *Nat. Rev. Immunol.* 11:221-230, 2011; Muhlbauer et al., *J. Hepatol.* 45:520-528, 2006; Pinchuk et al., *Gastroenterol.* 135:1228-1237, 2008; Stanciu et al, *J. Infect. Dis.,* 193:404-412, 2006). By contrast, constitutive basal expression of PD-L2 is low compared to PD-L1, and although PD-L2 expression was initially thought to be restricted to antigen-presenting cells such as monocytes, macrophages and dendritic cells (DCs) (Latchman et al., *Nature Immunol.* 2:261-268, 2001; Yamazaki et al., *J. Immunol.* 169:5538-5545, 2002), several groups have recently shown that PD-L2 expression can be induced on a wide variety of other immune cells and non-immune cells depending on microenvironmental stimuli (Kinter et al., *J. Immunol.* 181:6738-6746, 2008; Zhong et al., *Eur. J. Immunol.* 37:2405-2410, 2007; Messal et al., *Mol. Immunol.* 48:2214-2219, 2011; Lesterhuis et al., *Mol. Immunol.* 49:1-3, 2011).

PD-1 and its ligands are aberrantly expressed by malignant cells and surrounding microenvironmental cells. Within the tumor microenvironment, PD-1 is highly expressed on a large proportion of tumor-infiltrating lymphocytes (TILs) from many different tumor types and suppresses local effector immune responses. TIL expression of PD-1 is associated with impaired effector function (cytokine production and cytotoxic efficacy against tumor cells) and/or poor outcome in several tumor types (Thompson et al., *Clin. Cancer Res.* 13:1757-1761, 2007; Zhang et al., *Mol. Immunol.* 7:389-395, 2010; Ahmadzadeh M et al., *Blood* 114:1537-1544, 2009; Shi et al., *Int. J. Cancer* 128:887-896, 2011), including renal cell carcinoma, metastatic melanoma, as well as stomach, breast, ovarian, pancreatic, and lung cancers. Similarly, PD-L2 has been observed to be upregulated in a subset of human tumors and has occasionally been linked to poor outcome (Rozali et al., *Clin. Dev. Immunol.* 2012:656340, 2012).

Given its potential role in cancer-associated immune suppression in the tumor microenvironment, targeting the PD-1/PD-ligand pathway has been proposed as an attractive treatment strategy. Several studies in this regard have investigated the therapeutic effect of blocking antibodies against the PD-1/PD-L1 pathway, demonstrating enhanced tumor control rates, (Curran et al., *Proc. Natl. Acad Sci. USA* 107:4275-4280, 2010; Iwai et al., *Proc. Natl. Acad Sci. USA* 99:12293-12297, 2002; Pilon-Thomas et al., *J. Immunol.* 184:3442-3449, 2010; Zhang et al., *Blood* 114:1545-1552). However, few studies have investigated blocking of PD-L2 as a defined treatment strategy. Although in a few studies PD-L2 blocking strategies were used, this was always in combination with the targeting of PD-L1 (Parekh et al., *J. Immunol.* 182:2816-1826, 2009; He et al., *J. Immunol.* 173:4919-4928, 2004), which did not permit deducing the true value of anti-PD-L2 strategies.

SUMMARY OF THE INVENTION

The present invention is predicated in part on the determination that PD-L2 expression on cells such as antigen-presenting cells (APCs), which interact with antigen-specific immune effector cells (IECs) including T lymphocytes, inversely correlates with the severity of Th1-related disorders and that PD-L2 is required to establish Th1 immunity. It has also been found that clustering of PD-L2 on the surface of such IEC-interacting cells can inhibit the binding of PD-L1 to PD-1 to thereby inhibit the immunosuppressive functions of PD-L1 on IECs. Surprisingly, the present inventors have also determined that PD-L2 oligomers with a degree of oligomerization of greater than 2 have a significantly higher affinity than dimeric PD-L2 for binding to PD-1 and that such 'higher order PD-L2 oligomers' can markedly reduce the suppressive effects of PD-L1 on IEC function, including CD4+ T cell function. These discoveries have been reduced to practice in novel agents and methods for modulating Th1 immunity, as described hereafter.

Accordingly, in one aspect, the present invention provides polypeptide complexes that are useful for stimulating or enhancing Th1 immunity, which complexes are generally represented by formula (I):

$$[P]_n \quad \text{(I)}$$

wherein:
P, independently for each occurrence, represents a proteinaceous molecule comprising, consisting or consisting essentially of a PD-L2 polypeptide; and
n represents an integer greater than 2.

Suitably, P lacks a tumor or tumor-associated neovascular targeting domain.

In some embodiments, the PD-L2 polypeptide comprises, consists or consists essentially of a soluble portion of PD-L2, illustrative examples of which include a PD-L2 ectodomain with or without a signal peptide. In specific embodiments, the proteinaceous molecule lacks one or both of a PD-L2 transmembrane domain and a PD-L2 cytoplasmic domain.

Suitably, n is ≥3, ≥4, ≥5, ≥6, ≥7 or ≥8. In illustrative examples of this type, n is ≤100, ≤50, ≤30 or ≤20. In specific embodiments, n is in the range from 3 to 20, suitably 4 to 16, more suitably 8 to 12.

The proteinaceous molecules may be chemically coupled together to form the polypeptide complex. Alternatively, individual proteinaceous molecules may further comprise at least one oligomerization domain that facilitates self-assembly of the proteinaceous molecules to form the polypeptide complex. In these embodiments, the at least one oligomerization domain is typically operably connected to the PD-L2 polypeptide to form a single chain, chimeric polypeptide. In embodiments in which the at least one oligomerization domain is operably connected to the PD-L2 polypeptide, the present invention provides in another aspect a proteinaceous molecule that comprises, consists or consists essentially of a PD-L2 polypeptide as broadly described above and elsewhere herein, operably connected to at least one oligomerization domain that facilitates self-assembly of the proteinaceous molecule to form an polypeptide complex according to formula (I). Oligomerization domains may be operably connected upstream (i.e., amino-terminal to) and/or downstream (i.e., carboxy-terminal to) of the PD-L2 polypeptide. For example, in embodiments in which at least one oligomerization domain is operably connected downstream of the PD-L2 polypeptide, the proteinaceous molecule may comprise, consist of consist essentially of a single polypeptide chain represented by formula (II):

$$PD\text{-}L2\text{-}L\text{-}OMD_A \quad (II)$$

wherein:
PD-L2 represents a PD-L2 polypeptide;
OMDA is an oligomerization domain that forms oligomers $(OMDA)_i$ of i subunits $OMD_A$, wherein i is ≥3, suitably 3, 4, 5, or 6; and
L is a bond or a peptide linker.

Alternatively, the proteinaceous molecule may comprise, consist of consist essentially of a single polypeptide chain represented by formula (III):

$$PD\text{-}L2\text{-}L\text{-}OMD_A\text{-}L\text{-}OMD_B \quad (III)$$

wherein:
$OMD_A$ is an oligomerization domain that forms oligomers $(OMD_A)_i$ of i subunits $OMD_A$, wherein i is ≥2, suitably 2, 3, 4, 5, or 6;
L, independently for each occurrence, represents a bond or a peptide linker; and
$OMD_B$ is an oligomerization domain that forms oligomers $(OMD_B)_j$ of j subunits $OMD_B$, wherein j is an integer greater than i, suitably i+1, i+2, i+3, i+4, i+5, or i+6;
In illustrative examples of this type, i is 2 and j is 4 or 6.
In embodiments in which at least one oligomerization domain is operably connected upstream of the PD-L2 polypeptide, the proteinaceous molecule may comprise, consist of consist essentially of a single polypeptide chain represented by formula (IV):

$$OMD_A\text{-}L\text{-}PD\text{-}L2 \quad (IV)$$

wherein:
$OMD_A$ is an oligomerization domain that forms oligomers $(OMD_A)_i$ of i subunits $OMD_A$, wherein i is ≥3, suitably 3, 4, 5, or 6;
L is a bond or a peptide linker; and
PD-L2 represents a PD-L2 polypeptide.

Alternatively, the proteinaceous molecule may comprise, consist of consist essentially of a single polypeptide chain represented by formula (V):

$$OMD_B\text{-}L\text{-}OMD_A\text{-}L\text{-}PD\text{-}L2 \quad (V)$$

wherein:
$OMD_B$ is an oligomerization domain that forms oligomers $(OMD_B)_j$ of j subunits $OMD_B$, wherein j is ≥2, suitably 2, 3, 4, 5, or 6;
L, independently for each occurrence, represents a bond or a peptide linker; and
$OMD_A$ is an oligomerization domain that forms oligomers $(OMD_A)_i$ of i subunits $OMD_A$, wherein i is an integer greater than j, suitably j+1, j+2, j+3, j+4, j+5, or j+6; and
PD-L2 represents a PD-L2 polypeptide.

In illustrative examples of this type, j is 2 and i is 4 or 6.

In some embodiments, an individual oligomerization domain (e.g., $OMD_A$ or $OMD_B$) assembles into a heterooligomer in the presence of a binding partner. The oligomerization domain and the binding partner may be members of a specific binding pair, illustrative examples of which include biotin-avidin, biotin-streptavidin, antigen-antibody, hapten-anti-hapten, ligand-receptor and receptor-co-receptor.

The present invention contemplates the use of any suitable oligomerization domain including, for example, dimerization domains (e.g., immunoglobulin Fc domains, leucine zippers, etc.), trimerization domains (e.g., the catalytic subunit of *Escherichia coli* aspartate transcarbamoylase (ATCase), the 'foldon' trimerizing sequence from the bacteriophage T4 fibritin, neck region peptide, human lung surfactant D protein, oligomerization coiled-coil adhesins, complementary heptad repeat regions of an enveloped virus class I fusion protein, etc.), tetramerization domains (e.g., coiled-coil domain of tetrabrachion), pentamerization domains (e.g., the pentamerization domain of the tryptophane zipper or cartilage oligomeric matrix protein (COMP), etc.) and hexamerization domains (e.g., the tailpiece from the C-terminus of the heavy chain of an IgA antibody).

In some embodiments, the at least one oligomerization domain is connected directly to the PD-L2 polypeptide. In other embodiments, the at least one oligomerization domain and the PD-L2 polypeptide are connected by a peptide linker, which generally consists of about 1 to about 100 amino acid residues (and all integer amino acid residues therebetween), usually of about 1 to about 30 amino acid residues (and all integer amino acid residues therebetween), and typically of about 1 to about 20 amino acid residues (and all integer amino acid residues therebetween). The linker peptide may comprise at least one moiety selected from a purification moiety that facilitates purification of the proteinaceous molecule, an immune-modulating moiety that modulates an immune response to the proteinaceous molecule, and a structural flexibility-conferring moiety.

The proteinaceous molecule can be produced synthetically or by recombinant means. In embodiments in which the proteinaceous molecule is produced recombinantly, the present invention provides in another aspect a nucleic acid construct that comprises a coding sequence for a proteinaceous molecule as broadly described above and elsewhere herein, operably linked to a regulatory element that is operable in a host cell.

In a related aspect, the present invention provides a host cell that contains the nucleic acid construct broadly described above and elsewhere herein. The host cell may be a prokaryotic or eukaryotic host cell.

In embodiments in which the proteinaceous molecules comprise at least oligomerization domain, the proteinaceous molecules can self-assemble under suitable conditions (e.g., in aqueous solution) to form the polypeptide complex according to formula (I). Accordingly, in another aspect, the present invention provides a method of producing a polypeptide complex, wherein the method comprises: combining proteinaceous molecules as broadly defined above and elsewhere herein under conditions (e.g., in aqueous solution) suitable for the formation of a polypeptide complex, whereby a polypeptide complex is produced that comprises an oligomer of n subunits proteinaceous molecule.

The present invention in another aspect provides an immune-modulating composition comprising a polypeptide complex as broadly described above and elsewhere herein, and a pharmaceutically acceptable carrier or adjuvant.

The polypeptide complex or composition of the present invention is useful for stimulating, eliciting or augmenting an immune response, including a Th1 immune response, in subjects or production animals. Accordingly, another aspect of the present invention provides a method of stimulating, eliciting or augmenting an immune response, including a Th1 immune response, in a subject, wherein the method comprises administering to the subject a polypeptide complex or composition, as broadly described above and elsewhere herein.

In a related aspect, the present invention provides methods for treating a Th1-related disease or disorder in a subject. These methods generally comprise administering to the subject an effective amount of a polypeptide complex or composition, as broadly described above and elsewhere herein.

In some embodiments, the polypeptide complex or composition of the present invention is administered to a subject when the subject is identified as having impaired Th1 immunity. The Th1 immune status of the subject may be assessed using any suitable means. In advantageous embodiments, the Th1 immune status of the subject is assessed by a method comprising: (1) determining a Th1 immune status biomarker profile of a sample obtained from the subject, wherein the Th1 immune status biomarker profile comprises a biomarker value for at least one Th1 immune status biomarker in the sample, wherein the at least one Th1 immune status biomarker comprises PD-L2, and optionally PD-L1, of cells that interact with IEC-interacting cells in the sample; and (2) determining the indicator using the biomarker value(s), wherein the indicator is at least partially indicative of the Th1 immune status of the subject. In specific embodiments, the IEC-interacting cell is an APC, which is suitably selected from the group consisting of a dendritic cell and a macrophage. In representative examples of this type, the APC is a CD11c-expressing dendritic cells. In other embodiments, the IEC-interacting cell is a tumor cell.

Suitably, the biomarker value(s) is(are) at least partially indicative of a concentration of the Th1 immune status biomarker in the sample obtained from the subject, and in some embodiments of this type the biomarker value includes the abundance of the Th1 immune status biomarker. In a representative example, an individual biomarker value includes the percentage of IEC-interacting cells that express the Th1 immune status biomarker on the cell surface (e.g., PD-L2$^+$ dendritic cells, PD-L2$^+$ tumor cells, etc.). In some embodiments of this type, the Th1 immune status biomarker is PD-L2 and the biomarker value is a measurement of PD-L2 clustering on the surface of an IEC-interacting such as an APC (e.g., dendritic cell) or a tumor cell.

When determining the Th1 immune status of a subject, in some embodiments the level of PD-L2 is reduced in the sample relative to a control level of PD-L2 that correlates with the presence of normal or unimpaired Th1 immunity, and the indicator is thereby determined to be at least partially indicative of impaired Th1 immunity.

In other embodiments, the level of PD-L2 in the sample is about the same as a control level of PD-L2 that correlates with the presence of normal or unimpaired Th1 immunity, and the indicator is therefore determined to be at least partially indicative of normal or unimpaired Th1 immunity. In still other embodiments, the level of PD-L2 in the sample is increased relative to a control level of PD-L2 that correlates with the presence of normal or unimpaired Th1 immunity, and the indicator is therefore determined to be at least partially indicative of elevated Th1 immunity. In representative examples of these embodiments, the subject is not administered the polypeptide complex or composition of the present invention.

The indicator used in assessing Th1 immune status is made more reliable and of greater diagnostic power when the at least one Th1 immune status biomarkers further comprises PD-L1. Accordingly, in some embodiments the biomarker values from a pair of Th1 immune status biomarkers are used to determine the indicator. For example, in some preferred embodiments, the biomarker pair is PD-L2 and PD-L1. When more than one Th1 immune status biomarker is used in the methods of the invention, the method suitably further comprises applying a combining function to the biomarker values. In this regard, illustrative examples of suitable combining functions are selected from the group comprising: an additive model; a linear model; a support vector machine; a neural network model; a random forest model; a regression model; a genetic algorithm; an annealing algorithm; a weighted sum; a nearest neighbor model; and a probabilistic model.

Preferably, the methods described above and elsewhere herein suitably comprise: (a) determining a biomarker value for a first Th1 immune status biomarker; (b) determining a corresponding biomarker value for a second Th1 immune status biomarker; (c) determining the indicator using the biomarker values recorded on the first and second Th1 immune status biomarkers, the indicator being indicative of a ratio of the biomarker values recorded on the first and second Th1 immune status biomarkers. In illustrative methods of this type, the first Th1 immune status biomarker is PD-L2, and the second Th1 immune status biomarker is PD-L1. By way of an example, in some embodiments the ratio of the first and second Th1 immune status biomarker values determined from the sample ("the sample Th1 immune status biomarker ratio") is reduced relative to a control PD-L2:PD-L1 biomarker value ratio that correlates with the presence of normal or unimpaired Th1 immunity, and the indicator is determined to be at least partially indicative of impaired Th1 immunity. For example, the sample biomarker value ratio is suitably no more than about 95%, 94%, 93%, 92%, 91%, 90%, 80%, 70%, 60%, 50%, 40%, 30%, 20%, or 10% (and every integer in between) of the control biomarker value ratio of (e.g., determined from a control sample obtained from a subject with a normal or unimpaired Th1 immune response).

Conversely, when the sample PD-L2:PD-L1 biomarker value ratio is increased relative to a control PD-L2:PD-L1 biomarker value ratio that correlates with the presence of normal or unimpaired Th1 immunity, the indicator is determined to be at least partially indicative of elevated Th1 immunity. In these instances, the sample PD-L2:PD-L1 biomarker value ratio is at least about 105%, 106%, 107%, 108%, 109%, 110%, 120%, 130%, 140% 150%, 160%, 170%, 180%, 190%, 200%, 250%, 300%, 400%, 500%, 600%, 700%, 800%, 900%, or 1000% (and every integer in between) of the control biomarker value ratio (e.g., determined from a control sample obtained from a subject with a normal or unimpaired Th1 immune response). In other embodiments, when the sample PD-L2:PD-L1 biomarker value ratio is about the same as a control PD-L2:PD-L1 biomarker value ratio that correlates with the presence of normal or unimpaired Th1 immunity, the indicator is determined to be at least partially indicative of normal or unimpaired Th1 immunity. In these instances, the sample PD-L2:PD-L1 biomarker value ratio is usually from about 96% to 104% (and all integer percentages in between) of the control biomarker value ratio (e.g., determined from a control sample obtained from a subject with a normal or unimpaired Th1 immune response). In representative examples of these embodiments, the subject is not administered the polypeptide complex or composition of the present invention.

Any known techniques for measuring protein biomarkers or nucleic acid biomarkers are suitable for use with the present invention. For example, the biomarkers can be measured using flow cytometry, immunoassays, mass spectrometry, sequencing platforms, array and hybridization platforms, or a combination thereof.

The inventors' findings enable methods of diagnosing diseases and/or conditions with an undesirable Th1 immune status (also referred to interchangeably herein as "Th1-related diseases" or "Th1-related disorders"), as well as for administering treatment regimens, including polypeptide complex or composition of the present invention, for treating such diseases. Accordingly, in another aspect, the present invention provides a method as described above and elsewhere herein, wherein the indicator is used to diagnose the presence or absence of a Th1-related disease or disorder. In some embodiments, the disease or disorder is associated with a reduced or suppressed Th1 immune status, and is diagnosed when the level of PD-L2 in the sample obtained from the subject is below a predetermined threshold. For example, the disease or disorder that is associated with a reduced or suppressed Th1 immune status could be a cancer, including metastatic cancer, or a pathogenic infection.

DETAILED DESCRIPTION OF THE INVENTION

1. Definitions

Figure 1:
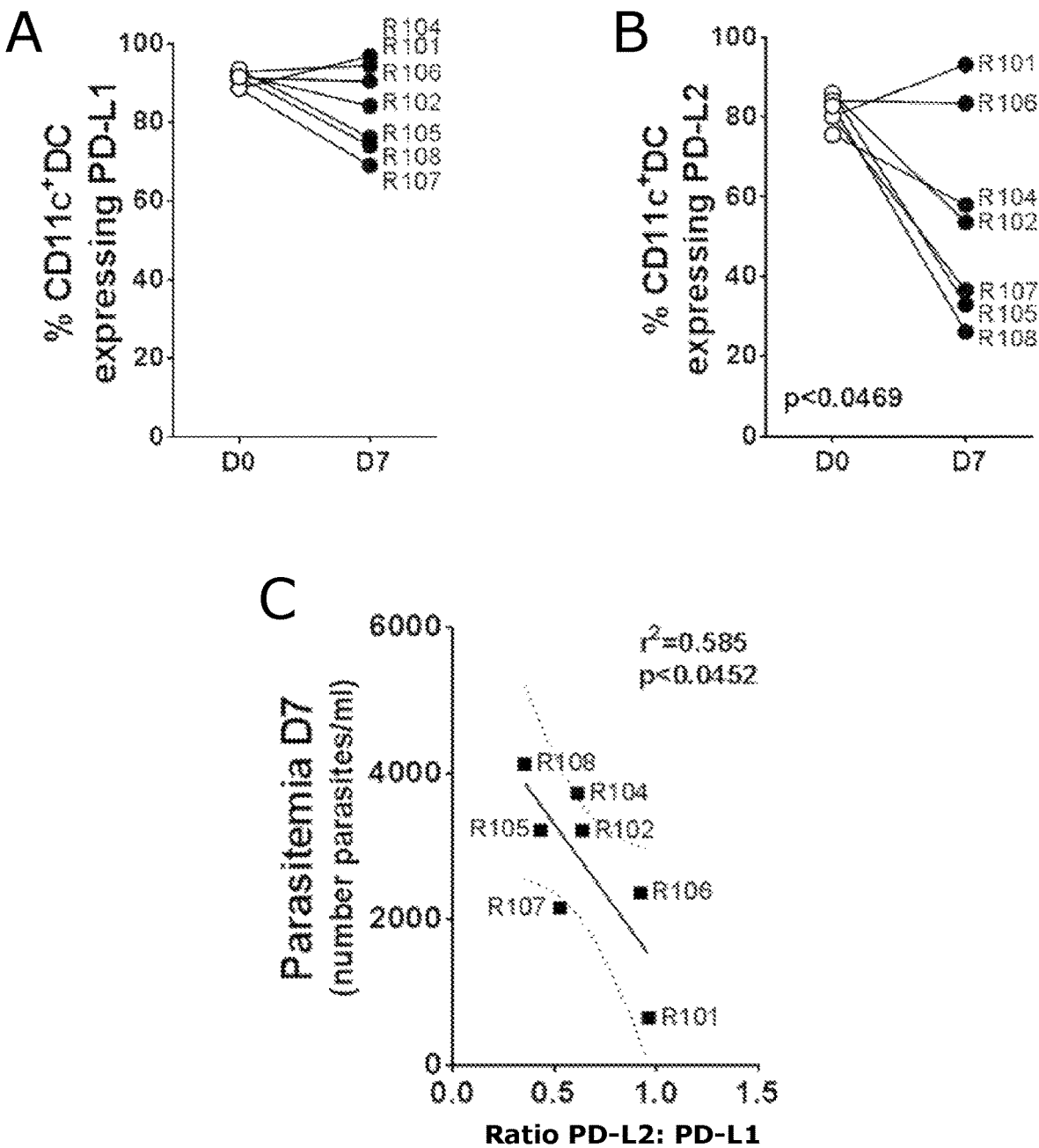
FIG. 1 is a graphical representation output from the FACS analysis characterizing biomarker expression on cell surface. PD-L2 expression on DCs inversely correlates with malaria parasitemia in humans. (A-C) Seven healthy human volunteers were inoculated with $P.$ $falciparum$ and blood examined for percentage of CD11c+DC expressing (A) PD-L1 and (B) PD-L2, before and seven days after infection. (C) Plot showing number of parasites per ml of blood versus ratio of % PD-L2: % PD-L1 DC. R101 to R108 represents each volunteer. The p value is testing the null hypothesis that the overall slope is zero.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, "and/or" refers to and encompasses any and all possible combinations of one or more of the associated listed items, as well as the lack of combinations when interpreted in the alternative (or).

Further, the terms "about" and "approximate", as used herein when referring to a measurable value such as an amount, dose, time, temperature, activity, level, number, frequency, percentage, dimension, size, amount, weight, position, length and the like, is meant to encompass variations of ±15%, ±10%, ±5%, ±1%, ±0.5%, or even ±0.1% of the specified amount, dose, time, temperature, activity, level, number, frequency, percentage, dimension, size, amount, weight, position, length and the like. In instances in which the terms "about" and "approximate" are used in connection with the location or position of regions within a reference polypeptide, these terms encompass variations of ±up to 20 amino acid residues, ±up to 15 amino acid residues, ±up to 10 amino acid residues, ±up to 5 amino acid residues, ±up to 4 amino acid residues, ±up to 3 amino acid residues, ±up to 2 amino acid residues, or even ±1 amino acid residue.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "adjuvant" as used herein refers to a compound that, when used in combination with a specific immunogen (e.g., a polypeptide complex of the present invention) in a composition, will augment the resultant immune response (e.g., a Th1 immune response) including intensification or broadening the specificity of either or both antibody and cellular immune responses.

The term "agent" or "modulatory agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells.

As used herein, the term "antigen" and its grammatically equivalents expressions (e.g., "antigenic") refer to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity. Representative antigen-binding molecules that are useful in the practice of the present invention include polyclonal and monoclonal antibodies as well as their fragments (such as Fab, Fab', F(ab')$_2$, Fv), single chain (scFv) and domain antibodies (including, for example, shark and camelid antibodies), and fusion proteins comprising an antibody, and any other modified configuration of the immunoglobulin molecule that comprises an antigen binding/recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called $\alpha$, $\delta$, $\epsilon$, $\gamma$, and $\mu$, respectively. The subunit structures and three-dimensional configurations of different classes of immunoglobulins are well known. Antigen-binding molecules also encompass dimeric antibodies, as well as multivalent forms of antibodies. In some embodiments, the antigen-binding molecules are chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., 1984, *Proc. Natl. Acad. Sci. USA* 81:6851-6855). Also contemplated, are humanized antibodies, which are generally produced by transferring complementarity determining regions (CDRs) from heavy and light variable chains of a non-human (e.g., rodent, preferably mouse) immunoglobulin into a human variable domain. Typical residues of human antibodies are then substituted in the framework regions of the non-human counterparts. The use of antibody components derived from humanized antibodies obviates potential problems associated with the immunogenicity of non-human constant regions. General techniques for cloning non-human, particularly murine, immunoglobulin variable domains are described, for example, by Orlandi et al. (1989, Proc. Natl. Acad. Sci. USA 86: 3833). Techniques for producing humanized monoclonal antibodies are described, for example, by Jones et al. (1986, *Nature* 321: 522), Carter et al. (1992, *Proc. Natl. Acad. Sci. USA* 89: 4285), Sandhu (1992, *Crit. Rev. Biotech.* 12: 437), Singer et al. (1993, *J. Immun.* 150: 2844), Sudhir (ed., Antibody Engineering Protocols, Humana Press, Inc. 1995), Kelley ("Engineering Therapeutic Antibodies," in Protein Engineering: Principles and Practice Cleland et al. (eds.), pages 399-434 (John Wiley & Sons, Inc. 1996), and by Queen et al., U.S. Pat. No. 5,693,762 (1997). Humanized antibodies include "primatized" antibodies in which the antigen-binding region of the antibody is derived from an antibody produced by immunizing macaque monkeys with the antigen of interest. Also contemplated as antigen-binding molecules are humanized antibodies.

The term "antigen presenting cells" (APCs) refers to a class of cells capable of presenting one or more antigens in the form of peptide-MHC complex recognizable by specific effector cells of the immune system (also referred to herein as "immune effector cells" or "IECs"), and thereby modulating (e.g., stimulating/enhancing or reducing/tolerizing/anergizing) an immune response to the antigen or antigens being presented. In specific embodiments of the present invention, the APCs are capable of activating IECs such as T lymphocytes, including CD8$^+$ and/or CD4$^+$ lymphocytes. Cells that have in vivo the potential to act as APC include, for example, not only professional APCs such as dendritic cells, macrophages, Langerhans cell, monocytes and B cells but also non-professional APCs illustrative examples of which include activated epithelial cells, fibroblasts, glial cells, pancreatic beta cells and vascular endothelial cells. Many types of cells are capable of presenting antigens on their cell surface for IEC, including T cell, recognition.

The term "biomarker" typically refers to a measurable characteristic that reflects the presence or nature (e.g., severity or status) of a physiological and/or pathophysiological state, including an indicator of risk of developing a particular physiological or pathophysiological state. For example, a biomarker may be present in a sample obtained from a subject before the onset of a physiological or pathophysiological state, including a symptom, thereof. Thus, the presence of the biomarker in a sample obtained from the subject is likely to be indicative of an increased risk that the subject will develop the physiological or pathophysiological state or symptom thereof. Alternatively, or in addition, the biomarker may be normally expressed in an individual, but its expression may change (i.e., it is increased (upregulated; over-expressed) or decreased (downregulated; under-expressed) before the onset of a physiological or pathophysiological state, including a symptom thereof. Thus, a change in the level of the biomarker is likely to be indicative of an increased risk that the subject will develop the physiological or pathophysiological state or symptom thereof. Alternatively, or in addition, a change in the level of a biomarker may reflect a change in a particular physiological or pathophysiological state, or symptom thereof, in a subject, thereby allowing the nature (e.g., severity) of the physiological or pathophysiological state, or symptom thereof, to be tracked over a period of time. This approach may be useful in, for example, monitoring a treatment regimen for the purpose of assessing its effectiveness (or otherwise) in a subject. As herein described, reference to the level of a biomarker includes the concentration of a biomarker, or the level of expression of a biomarker, or the activity of the biomarker, as will be described in more detail below.

The term "biomarker value" refers to a value measured or derived for at least one corresponding biomarker of a subject and which is typically at least partially indicative of an abundance or concentration of a biomarker in a sample taken from the subject. Thus, the biomarker values could be measured biomarker values, which are values of biomarkers measured for the subject, or alternatively could be derived biomarker values, which are values that have been derived from one or more measured biomarker values, for example by applying a function to the one or more measured biomarker values. Biomarker values can be of any appropriate form depending on the manner in which the values are determined. For example, the biomarker values could be determined using high-throughput technologies such as mass spectrometry, sequencing platforms, array and hybridization platforms, immunoassays, flow cytometry, or any combination of such technologies. In one preferred example, the biomarker values relate to a level of activity or abundance of a protein expression product or other measurable molecule, quantified using a technique such as flow cytometry or the like. In this case, the biomarker values can be in the form of a percentage value of cells expressing the biomarker within a sample, as will be appreciated by persons skilled in the art and as will be described in more detail below.

The term "biomarker profile" refers to one or a plurality of one or more types of biomarkers (e.g., a polypeptide molecule, a cDNA molecule, etc.), or an indication thereof, together with a feature, such as a measurable aspect (e.g., a biomarker value) of the biomarker(s). A biomarker profile may comprise a single biomarker whole level, abundance or amount correlates with the Th1 immune status of a subject (e.g., an enhanced Th1 immune status or a reduced Th1 immune status). Alternatively, a biomarker profile may comprise at least two such biomarkers or indications thereof, where the biomarkers can be in the same or different classes, such as, for example, a polypeptide and a nucleic acid. Thus, a biomarker profile may comprise at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 or more biomarkers or indications thereof. In some embodiments, a biomarker profile comprises a couple, several, tens, or hundreds of biomarkers or indications thereof. A biomarker profile can further comprise one or more controls or internal standards. In certain embodiments, the biomarker profile comprises at least one biomarker, or indication thereof, that serves as an internal standard. In other embodiments, a biomarker profile comprises an indication of one or more types of biomarkers. The term "indication" as used herein in this context merely refers to a situation where the biomarker profile contains symbols, data, abbreviations or other similar indicia for a biomarker, rather than the biomarker molecular entity itself. The term "biomarker profile" is also used herein to refer to a biomarker value or combination of at least two biomarker values, wherein individual biomarker values correspond to values of biomarkers that can be measured or derived from one or more subjects, which combination is characteristic of a Th1 immune status, discrete condition, stage of condition, subtype of condition or a prognosis for a discrete condition, stage of condition, subtype of condition. The term "profile biomarkers" is used to refer to a subset of the biomarkers that have been identified for use in a biomarker profile that can be used in performing a clinical assessment, such as to rule in or rule out a specific condition, different stages or severity of conditions, subtypes of different conditions or different prognoses. The number of profile biomarkers will vary, but is typically of the order of 10 or less.

The term "chimeric", when used in reference to a molecule, means that the molecule contains portions that are derived from, obtained or isolated from, or based upon two or more different origins or sources. Thus, a polypeptide is chimeric when it comprises two or more amino acid sequences of different origin and includes (1) polypeptide sequences that are not found together in nature (i.e., at least one of the amino acid sequences is heterologous with respect to at least one of its other amino acid sequences), or (2) amino acid sequences that are not naturally adjoined.

By "clustering," and grammatical equivalents used herein, is meant any reversible or irreversible association of more than two of the same Th1 immune status biomarkers (e.g., PD-L2). Clusters can be made up of 3, 4, 5, 6, 7, 8, 9, 10, 12, 20, etc. biomarkers. Clusters of two biomarkers are termed dimers. Clusters of three or more biomarkers are generally termed oligomers, with individual numbers of clusters having their own designation, for example, a cluster of three biomarkers is a trimer, a cluster of four biomarkers is a tetramer, a cluster of five biomarkers is a pentamer, a cluster of six biomarkers is a hexamer, a cluster of seven biomarkers is a heptamer, a cluster of eight biomarkers is an octamer, a cluster of nine biomarkers is a nonamer, a cluster of ten biomarkers is a decamer, a cluster of twelve biomarkers is a dodecamer, and a cluster of twenty biomarkers is a eicosamer.

By "coding sequence" is meant any nucleic acid sequence that contributes to the code for the polypeptide product of a gene or for the final mRNA product of a gene (e.g. the mRNA product of a gene following splicing). By contrast, the term "non-coding sequence" refers to any nucleic acid sequence that does not contribute to the code for the polypeptide product of a gene or for the final mRNA product of a gene.

The terms "coiled coil" or "coiled coil structure" are used interchangeably herein to refer to a structural motif in proteins, in which two or more α-helices (most often 2-7 α-helices) are coiled together like the strands of a rope (dimers and trimers are the most common types). Many coiled coil type proteins are involved in important biological functions such as the regulation of gene expression e.g., transcription factors. Coiled coils often, but not always, contain a repeated pattern, hpphppp or hppphpp, of hydrophobic (h) and polar (p) amino-acid residues, referred to as a heptad repeat (see herein below). Folding a sequence with this repeating pattern into an α-helical secondary structure causes the hydrophobic residues to be presented as a 'stripe' that coils gently around the helix in left-handed fashion, forming an amphipathic structure. The most favorable way for two such helices to arrange themselves in a water-filled environment of is to wrap the hydrophobic strands against each other sandwiched between the hydrophilic amino acids. It is thus the burial of hydrophobic surfaces, which provides the thermodynamic driving force for oligomerization of the α-helices. The packing in a coiled-coil interface is exceptionally tight. The α-helices may be parallel or anti-parallel, and usually adopt a left-handed super-coil. Although disfavored, a few right-handed coiled coils have also been observed in nature and in designed proteins. The terms "coiled coil" or "coiled coil structure" will be clear to the person skilled in the art based on the common general knowledge. Particular reference in this regard is made to review papers concerning coiled coil structures, such as for example, Cohen and Parry (1990. *Proteins* 7:1-15); Kohn and Hodges (1998. *Trends Biotechnol* 16:379-389); Schneider et al. (1998. *Fold Des* 3:R29-R40); Harbury et al. (1998. *Science* 282:1462-1467); Mason and Arndt (2004. *ChemBioChem* 5:170-176); Lupas and Gruber (2005. *Adv Protein Chem* 70:37-78); Woolfson (2005. *Adv Protein Chem* 70:79-112); Parry et al. 2008. *J Struct Biol* 163:258-269); and Mcfarlane et al. (2009. *Eur J Pharmacol* 625:101-107).

As used herein, a "companion diagnostic" refers to a diagnostic method and or reagent that is used to identify subjects susceptible to treatment with a particular treatment or to monitor treatment and/or to identify an effective dosage for a subject or sub-group or other group of subjects. For purposes herein, a companion diagnostic refers to reagents, such as a reagent for determining a biomarker value of a Th1 immune system biomarker (e.g., as described herein) in a sample. The companion diagnostic refers to the reagents and also to the test(s) that is/are performed with the reagent.

As used herein the term "complementary" and grammatically equivalent expressions thereof refer to the characteristic of two or more structural elements (e.g., peptide, polypeptide, nucleic acid, small molecule, or portions thereof etc.) of being able to hybridize, oligomerize (e.g., dimerize, trimerize, tetramerize, pentamerize, hexamerize, heptamerize, octamerize, nonamerize, decamerize, undecamerize, dodecamerize), interact or otherwise form a complex with each other. For example, "complementary regions of a polypeptide" are capable of coming together to form a complex.

As used herein, the term "complex" refers to an assemblage or aggregate of molecules (e.g., peptides, polypeptides, etc.) in direct and/or indirect contact with one another. In specific embodiments, "contact", or more particularly, "direct contact" means two or more molecules are close enough so that attractive noncovalent interactions, such as Van der Waal forces, hydrogen bonding, ionic and hydrophobic interactions, and the like, dominate the interaction of the molecules. In such embodiments, a complex of molecules (e.g., a peptide and polypeptide) is formed under conditions such that the complex is thermodynamically favored (e.g., compared to a non-aggregated, or non-complexed, state of its component molecules). The term "polypeptide complex" or "protein complex," as used herein, refers to a trimer, tetramer, pentamer, hexamer, heptamer, octamer, nonamer, decamer, undecamer, dodecamer, or higher order oligomer. In specific embodiments, the polypeptide complexes are formed by self-assembly of a chimeric polypeptide that comprises a PD-L2 polypeptide and at least one oligomerization domain.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the terms "conjugated", "linked", "fused" or "fusion" and their grammatical equivalents, in the context of joining together of two more elements or components or domains by whatever means including chemical conjugation or recombinant means (e.g., by genetic fusion) are used interchangeably. Methods of chemical conjugation (e.g., using heterobifunctional crosslinking agents) are known in the art. More specifically, as used herein, a PD-L2 polypeptide-oligomerization domain fusion or conjugate refers to the genetic or chemical conjugation of a PD-L2 polypeptide to at least one oligomerization domain. In specific embodiments, at least one oligomerization domain is fused indirectly to a PD-L2 polypeptide, via a peptide linker, such as a glycine-serine (gly-ser) linker. In other embodiments, at least one oligomerization domain is fused directly to a PD-L2 polypeptide.

A "conservative amino acid substitution" is one in which the amino acid residue is replaced with an amino acid residue having a similar side chain. Families of amino acid residues having similar side chains have been defined in the art, which can be generally sub-classified as follows:

TABLE 1

AMINO ACID SUB-CLASSIFICATION

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 2

EXEMPLARY AND PREFERRED AMINO ACID SUBSTITUTIONS

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |

TABLE 2-continued

EXEMPLARY AND PREFERRED
AMINO ACID SUBSTITUTIONS

| Original Residue | Exemplary Substitutions | Preferred Substitutions |
|---|---|---|
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be containing within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, 3$^{rd}$ edition Volumes 1, 2, and 3. J. F. Sambrook, D. W. Russell, and N. Irwin, Cold Spring Harbor Laboratory Press, 2000.

The term "correlating" refers to determining a relationship between one type of data with another or with a state (e.g., Th1 immune status).

By "corresponds to" or "corresponding to" is meant an amino acid sequence that displays substantial sequence similarity or identity to a reference amino acid sequence. In general the amino acid sequence will display at least about 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to at least a portion of the reference amino acid sequence.

The term "degree of oligomerization" refers to the number (n) of proteinaceous molecule units in a polypeptide complex according to formula (I).

As used herein, the terms "diagnosis," "diagnosing" and the like are used interchangeably herein to encompass determining the likelihood that a subject will develop a condition, or the existence or nature of a condition in a subject. These terms also encompass determining the severity of disease or episode of disease, as well as in the context of rational therapy, in which the diagnosis guides therapy, including initial selection of therapy, modification of therapy (e.g., adjustment of dose or dosage regimen), and the like.

By "likelihood" is meant a measure of whether a subject with particular measured or derived biomarker values actually has a condition (or not) based on a given mathematical model. An increased likelihood for example may be relative or absolute and may be expressed qualitatively or quantitatively. For instance, an increased likelihood may be determined simply by determining the subject's measured or derived biomarker values for at least two Th1 immune status biomarkers and placing the subject in an "increased likelihood" category, based upon previous population studies. The term "likelihood" is also used interchangeably herein with the term "probability". The term "risk" relates to the possibility or probability of a particular event occurring at some point in the future. "Risk stratification" refers to an arraying of known clinical risk factors to allow physicians to classify patients into a low, moderate, high or highest risk of developing a particular disease.

The term "domain", as used herein, refers to a part of a molecule or structure that shares common physicochemical features, such as, but not limited to, hydrophobic, polar, globular and helical domains or properties such as ligand-binding, membrane fusion, signal transduction, cell penetration, oligomerization and the like. Often, a domain has a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain. Domains may be co-extensive with regions or portions thereof; domains may also include distinct, non-contiguous regions of a molecule. Examples of protein domains include, but are not limited to, a cellular or extracellular localization domain (e.g., signal peptide; SP), an immunoglobulin (Ig) domain, an ectodomain, a transmembrane (TM) domain, and a cytoplasmic (C) domain.

As used herein, the terms "encode", "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode", "encoding" and the like include a RNA product resulting from transcription of a DNA molecule, a protein resulting from translation of a RNA molecule, a protein resulting from transcription of a DNA molecule to form a RNA product and the subsequent translation of the RNA product, or a protein resulting from transcription of a DNA molecule to provide a RNA product, processing of the RNA product to provide a processed RNA product (e.g., mRNA) and the subsequent translation of the processed RNA product.

An "ectodomain" is the domain of a cell membrane protein that extends into the extracellular space (i.e., the space outside the cell). Ectodomains are usually the parts of proteins that initiate contact with surfaces, which leads to signal transduction. The ectodomain of PD-L2 as defined herein thus refers to the part of the PD-L2 that extends into the extracellular space (the extracellular domain), but also includes shorter parts or fragments thereof that are responsible for the binding to a corresponding receptor, such as PD-1. The term "ectodomain of PD-L2 or a fragment thereof" thus refers to the extracellular domain of PD-L2 that forms the extracellular domain or to parts thereof that are still able to bind to the receptor (i.e., receptor binding domain).

By "effective amount," in the context of eliciting an immune response to a fusion protein of an enveloped virus, or complex of the fusion protein, or of treating or preventing a disease or condition, is meant the administration of an amount of agent to an individual in need thereof, either in a single dose or as part of a series, that is effective for that elicitation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The term "endogenous production" refers to expression of a nucleic acid in an organism and the associated production and/or secretion of an expression product of the nucleic acid in the organism. In specific embodiments, the organism is multicellular (e.g., a vertebrate animal, preferably a mammal, more preferably a primate such as a human) and the nucleic acid is expressed within cells or tissues of the multicellular organism.

The term "expression" with respect to a gene sequence refers to transcription of the gene to produce a RNA transcript (e.g., mRNA, antisense RNA, siRNA, shRNA, miRNA, etc.) and, as appropriate, translation of a resulting mRNA transcript to a protein. Thus, as will be clear from the context, expression of a coding sequence results from transcription and translation of the coding sequence. Conversely, expression of a non-coding sequence results from the transcription of the non-coding sequence.

As used herein, a "fusion" protein refers to two or more polypeptides coupled together which are not naturally found in a coupled arrangement.

As used herein, the term "gene" refers to a nucleic acid molecule capable of being used to produce mRNA, antisense RNA, siRNA, shRNA, miRNA, and the like, and in some embodiments, polypeptide. Genes may or may not be capable of being used to produce a functional protein. Genes can include both coding and non-coding regions (e.g., introns, regulatory elements including promoters, enhancers, termination sequences and 5' and 3' untranslated regions). A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule. Reference to a "gene" also includes within its scope reference to genes having a contiguous sequence, thus defining contiguous nucleic acid entities, as defined herein, or a non-contiguous sequence thus defining a non-contiguous nucleic acid entity as defined herein. In certain embodiments, the term "gene" includes within its scope the open reading frame encoding specific polypeptides, introns, and adjacent 5' and 3' non-coding nucleotide sequences involved in the regulation of expression. In this regard, the gene may further comprise control sequences such as promoters, enhancers, termination and/or polyadenylation signals that are naturally associated with a given gene, or heterologous control sequences. The gene sequences may be cDNA or genomic DNA or a fragment thereof. The gene may be introduced into an appropriate vector for extrachromosomal maintenance or for introduction into a host.

The term "heterologous" as used herein refers to any proteinaceous moiety whose sequence is chosen in such a way that the product of the fusion of this sequence with a PD-L2 polypeptide has a sequence different from a precursor or mature form of a wild-type PD-L2 polypeptide.

The term "host" refers to any organism, or cell thereof, whether eukaryotic or prokaryotic into which a construct of the invention can be introduced. In particular embodiments, the term "host" refers to eukaryotes, including unicellular eukaryotes such as yeast and fungi as well as multicellular eukaryotes such as animals non-limiting examples of which include invertebrate animals (e.g., insects, cnidarians, echinoderms, nematodes, etc.); eukaryotic parasites (e.g., malarial parasites, such as *Plasmodium falciparum*, helminths, etc.); vertebrate animals (e.g., fish, amphibian, reptile, bird, mammal); and mammals (e.g., rodents, primates such as humans and non-human primates). Thus, the term "host cell" suitably encompasses cells of such eukaryotes as well as cell lines derived from such eukaryotes. The term "host cell" also includes within its scope an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell As used herein, the term "immune effector cells" (IECs) refers to a population of leukocytes including lymphocytes that display effector moiety receptors, e.g., cytokine receptors, and/or Fc receptors on their surface through which they bind an effector moiety, e.g., a cytokine, and/or an Fc region of an antibody and contribute to the destruction of target cells, e.g., tumor cells. IECs may for example mediate cytotoxic or phagocytic effects. IECs cells include, but are not limited to, effector T cells such as $CD8^+$ cytotoxic T cells, $CD4^+$ helper T cells, γδ T cells, NK cells, NK-like T cells and lymphokine-activated killer (LAK) cells. The activity of IECs can be modulated through their interaction with APCs, including professional antigen-presenting cells such as macrophages, dendritic cells, Langerhans cell, B cells and monocytes.

As use herein, the term "immunogenic composition" or "immunogenic formulation" refers to a preparation which, when administered to a vertebrate, especially an animal such as a mammal, will induce an immune response, including a Th1 immune response.

The term "indicator" as used herein refers to a result or representation of a result, including any information, number, ratio, signal, sign, mark, or note by which a skilled artisan can estimate and/or determine a likelihood or risk of whether or not a subject is suffering from a given disease. In the case of the present invention, the "indicator" may optionally be used together with other clinical characteristics, to arrive at a determination of the Th1 immune status of the subject. That such an indicator is "determined" is not meant to imply that the indicator is 100% accurate. The skilled clinician may use the indicator together with other clinical indicia to arrive at a diagnosis.

By "linker" is meant a molecule or group of molecules (such as a monomer or polymer) that connects two molecules and often serves to place the two molecules in a desirable configuration. In specific embodiments, a "peptide linker" refers to an amino acid sequence that connects two proteins, polypeptides, peptides, domains, regions, or motifs and may provide a spacer function compatible with interaction of the two sub-binding (e.g., oligomerization) domains so that the resulting polypeptide retains a specific binding affinity to a target molecule or retains signaling activity (e.g., PD-L2 polypeptide). In certain embodiments, a linker is comprised of about two to about 35 amino acids, for instance, or about four to about 20 amino acids or about eight to about 15 amino acids or about 15 to about 25 amino acids.

As used herein, the term "moiety" refers to a portion of a molecule, which may be a functional group, a set of functional groups, and/or a specific group of atoms within a molecule, that is responsible for a characteristic chemical, biological, and/or medicinal property of the molecule.

By "obtained" is meant to come into possession. Samples so obtained include, for example, nucleic acid extracts or polypeptide extracts isolated or derived from a particular source. For instance, the extract may be isolated directly from a biological fluid or tissue of a subject.

An "oligomerization domain", as used herein, refers to a protein domain that preferentially interacts or associates with one or more other protein domains directly or via a bridging molecule, wherein the interaction of the other protein domains substantially contribute to or efficiently promote oligomerization (i.e., the formation of a dimer, trimer, tetramer, pentamer, hexamer, heptamer, octamer, nonamer, decamer, undecamer, dodecamer, or higher order oligomer, which may be a homooligomer or heterooligomer). Such 'complementary' oligomerization domains include dimerization domains (e.g., immunoglobulin Fc domains, leucine zippers, etc.), trimerization domains (e.g., the catalytic subunit of *Escherichia coli* aspartate transcarbamoylase (ATCase), the 'foldon' trimerizing sequence from the bacteriophage T4 fibritin, neck region peptide, human lung surfactant D protein, oligomerization coiled-coil adhesins, complementary heptad repeat regions of an enveloped virus class I fusion protein, etc.), tetramerization domains (e.g., coiled-coil domain of tetrabrachion), pentamerization domains (e.g., the pentamerization domain of the tryptophane zipper or cartilage oligomeric matrix protein (COMP), etc.) and hexamerization domains (e.g., the tail-piece from the C-terminus of the heavy chain of an IgA antibody), which, if desired, can be used in combination to form higher order oligomers such as heptamers, octamers, nonamers, decamers, undecamers, dodecamers, etc.

The term "operably connected" or "operably linked" as used herein refers to a juxtaposition wherein the components so described are in a relationship permitting them to function in their intended manner. For example, a regulatory sequence (e.g., a promoter) "operably linked" to a nucleotide sequence of interest (e.g., a coding and/or non-coding sequence) refers to positioning and/or orientation of the control sequence relative to the nucleotide sequence of interest to permit expression of that sequence under conditions compatible with the control sequence. The control sequences need not be contiguous with the nucleotide sequence of interest, so long as they function to direct its expression. Thus, for example, intervening non-coding sequences (e.g., untranslated, yet transcribed, sequences) can be present between a promoter and a coding sequence, and the promoter sequence can still be considered "operably linked" to the coding sequence. Likewise, "operably connecting" a PD-L2 polypeptide to at least one heterologous oligomerization domain encompasses positioning and/or orientation of the oligomerization domain(s) relative to the PD-L2 polypeptide to permit self-assembly of the PD-L2-oligomerization domain(s) chimeric polypeptide to form a polypeptide complex.

The terms "patient", "subject", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. A preferred subject is a human in need of eliciting an immune response to a fusion protein of an enveloped virus, or complex of the fusion protein. However, it will be understood that the aforementioned terms do not imply that symptoms are present.

As used interchangeably herein, "PD-L2 activity", "biological activity of PD-L2" or "functional activity of PD-L2", refers to an activity exerted by a PD-L2 polypeptide or nucleic acid molecule on a PD-L2-responsive cell or tissue, or on a PD-L2 polypeptide binding partner, as determined in vivo, or in vitro, according to standard techniques. In some embodiments, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In specific embodiments, a PD-L2 target molecule is selected from the PD-1 receptor and repulsive guidance molecule b (RGMb). Alternatively, a PD-L2 activity is an indirect activity, such as a cellular signaling activity mediated by interaction of the PD-L2 polypeptide with a natural binding partner, e.g., PD-1 or RGMb. The biological activities of PD-L2 are described herein. For example, the PD-L2 polypeptides of the present invention can have one or more of the following activities: 1) bind to and/or modulate the activity of the receptor PD-1 or other PD-L2 natural binding partners such as RGMb, 2) modulate intra- or intercellular signaling, 3) modulate activation of immune cells, e.g., T lymphocytes, and 4) modulate the immune response, including the Th1 immune response, of an organism, e.g., a mammal such as a human or other primate.

The terms "PD-L2 expression" and "PD-L1 expression" refers to the transcription and/or translation and/or activity of PD-L2 and PD-L1 respectively. Several methods can be utilized to determine the level of PD-L2 and PD-L1 expression, as described for example herein.

A "PD-L2 polypeptide" refers to a polypeptide having an amino acid sequence corresponding to a PD-L2 molecule. This term encompasses, without limitation, polypeptides having an amino acid sequence that shares at least 70% (and at least 71% to at least 99% and all integer percentages in between) sequence identity or similarity with the sequence set forth in any one of SEQ ID NOs: 1, 2, 3, 4, 5 or 6. It further encompasses natural allelic variation of PD-L2 polypeptides that may exist and occur from one organism to another. Also, degree and location of glycosylation or other post-translation modifications may vary depending on the chosen host and the nature of the hosts cellular environment. The term "PD-L2 polypeptide" is also intended to encompass PD-L2 polypeptides in their precursor form, as well as those that have been processed to yield their respective bioactive forms. It further encompasses PD-L2 polypeptides that have either been chemically modified relative to a reference or naturally-occurring PD-L2 polypeptide and/or contain one or more amino acid sequence alterations relative to a reference or naturally-occurring PD-L2 polypeptide and/or contain truncated amino acid sequences relative to a reference or naturally-occurring full-length or precursor PD-L2 polypeptide or domains thereof, including the PD-L2 signal peptide, IgV and IgC domains, ectodomain, transmembrane domain and intracytoplasmic domain. Alternatively, or in addition, PD-L2 polypeptides, including complexes thereof, may exhibit different properties relative to a reference or naturally-occurring PD-L2 polypeptide, including altered (e.g., increased) stability and altered (e.g., enhanced) biological activity such as but not limited to: 1) enhanced binding to and/or signaling of the receptor PD-1 or other PD-L2 natural binding partners such as RGMb, 2) enhanced intra- or intercellular signaling, 3) enhanced activation of immune cells, e.g., T lymphocytes, and 4) enhanced immune response, including a Th1 immune response, in a subject, e.g., a mammal such as a human or other primate. The term "PD-L2 polypeptide" also encompasses proteinaceous molecules with a slightly modified amino acid sequence, for instance, polypeptides having a modified N-terminal end including N-terminal amino acid deletions or additions, and/or polypeptides that have been chemically modified relative to a reference or naturally-occurring PD-L2 polypeptide. PD-L2 polypeptides also encompass proteinaceous molecules exhibiting substantially the same or better bioactivity than a reference or naturally-occurring PD-L2 polypeptide, or, alternatively, exhibiting substantially modified or reduced bioactivity relative to a reference or naturally-occurring PD-L2 polypeptide.

By "pharmaceutically acceptable carrier" is meant a solid or liquid filler, diluent or encapsulating substance that can be safely used in topical or systemic administration to an animal, preferably a mammal, including humans. Representative pharmaceutically acceptable carriers include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient(s), its use in the pharmaceutical compositions is contemplated.

The term "polynucleotide" or "nucleic acid" as used herein designates mRNA, RNA, cRNA, cDNA or DNA. The term typically refers to polymeric forms of nucleotides of at least 10 bases in length, either ribonucleotides or deoxynucleotides or a modified form of either type of nucleotide. The term includes single and double stranded forms of DNA.

"Polypeptide", "peptide", "protein" and "proteinaceous molecule" are used interchangeably herein to refer to molecules comprising or consisting of a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

"Regulatory elements", "regulatory sequences", control elements", "control sequences" and the like are used interchangeably herein to refer to nucleotide sequences located upstream (5' non-coding sequences), within, or downstream (3' non-coding sequences) of a coding sequence, and which influence the transcription, RNA processing or stability, or translation of the associated coding sequence, either directly or indirectly. Regulatory elements include enhancers, promoters, translation leader sequences, introns, Rep recognition element, intergenic regions and polyadenylation signal sequences. They include natural and synthetic sequences as well as sequences which may be a combination of synthetic and natural sequences.

The term "sample" as used herein includes any biological specimen that may be extracted, untreated, treated, diluted or concentrated from a subject. Samples may include, without limitation, biological fluids such as whole blood, serum, red blood cells, white blood cells, plasma, saliva, urine, stool (i.e., faeces), tears, sweat, sebum, nipple aspirate, ductal lavage, tumor exudates, synovial fluid, ascitic fluid, peritoneal fluid, amniotic fluid, cerebrospinal fluid, lymph, fine needle aspirate, amniotic fluid, any other bodily fluid, cell lysates, cellular secretion products, inflammation fluid, semen and vaginal secretions. Samples may include tissue samples and biopsies, tissue homogenates and the like.

Advantageous samples may include ones comprising any one or more biomarkers as taught herein in detectable quantities. Suitably, the sample is readily obtainable by minimally invasive methods, allowing the removal or isolation of the sample from the subject. In certain embodiments, the sample contains blood, especially peripheral blood, or a fraction or extract thereof. Typically, the sample comprises blood cells such as mature, immature or developing leukocytes, including lymphocytes, polymorphonuclear leukocytes, neutrophils, monocytes, reticulocytes, basophils, coelomocytes, hemocytes, eosinophils, megakaryocytes, macrophages, dendritic cells natural killer cells, or fraction of such cells (e.g., a nucleic acid or protein fraction). In specific embodiments, the sample comprises leukocytes including peripheral blood mononuclear cells (PBMC).

"Self-assembly" refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gin, Cys and Met) occurs in both sequences to yield the number of matched positions, dividing the number of matched positions by the total number of positions in the window of comparison (i.e., the window size), and multiplying the result by 100 to yield the percentage of sequence identity. The present invention contemplates the use in the methods and systems of the present invention of full-length IL-22 polypeptides as well as their biologically active fragments. Typically, biologically active fragments of a full-length IL-22 polypeptide may participate in an interaction, for example, an intra-molecular or an inter-molecular interaction.

"Similarity" refers to the percentage number of amino acids that are identical or constitute conservative substitutions as defined in Tables 1 and 2 supra. Similarity may be determined using sequence comparison programs such as GAP (Deveraux et al. 1984, Nucleic Acids Research 12: 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence," "comparison window", "sequence identity," "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

As used herein, the term "single-chain" is a single, linear and contiguous arrangement of covalently linked amino acids.

As used herein, the term "soluble" polypeptide such as soluble PD-L2 polypeptide refers to a non-naturally occurring polypeptide which is normally membrane-bound, and which now functions in a non-membrane bound state while retaining the ability to bind to molecules and is recognized by its membrane-bound counterpart, for example, PD-1.

A "Th1-related disease" or "Th1-related disorder" as used interchangeably herein refers to a disease that is associated with the development of a Th1 immune response. A "Th1 immune response" as used herein refers to the proliferation or increased differentiation of Th1 cells. A Th1-related disease or disorder is suitably identified by (1) levels of Th1 cells, Th1 cytokines and/or Th1 antibodies that exceed those normally found in a human, animal, or cell culture; (2) pathological findings associated with the disease or medical condition that can be mimicked experimentally in animals by administration of agents that upregulate proliferation or differentiation of Th1 cells; or (3) a pathology induced in experimental animal models of the disease or medical condition can be inhibited or abolished by treatment with agents that inhibit the proliferation or differentiation of Th1 cells. In most Th1-related diseases, at least two of the three conditions are met.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

By "vector" is meant a polynucleotide molecule, suitably a DNA molecule derived, for example, from a plasmid, bacteriophage, yeast or virus, into which a polynucleotide can be inserted or cloned. A vector may contain one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

The terms "wild-type", "native" and "naturally occurring" are used interchangeably herein to refer to a gene or gene product that has the characteristics of that gene or gene product when isolated from a naturally occurring source. A wild type, native or naturally occurring gene or gene product (e.g., a polypeptide) is that which is most frequently observed in a population and is thus arbitrarily designed the "normal" or "wild-type" form of the gene or gene product.

Each embodiment described herein is to be applied mutatis mutandis to each and every embodiment unless specifically stated otherwise.

2. Polypeptide Complexes

The present inventors have surprisingly discovered that PD-L2 expression on IEC-interacting cells such as APCs (e.g., dendritic cells) inversely correlates with the severity of Th1-related disorders and that PD-L2 is required to establish Th1 immunity. In other words, Th1 immunity is compromised if PD-L2 expression on APCs falls below a threshold that correlates with the presence of normal or unimpaired Th1 immunity. The present inventors have also discovered that clustering of PD-L2 on the surface of APCs can inhibit binding of PD-L1 to PD-1 to thereby inhibit the immunosuppressive functions of PD-L1 on antigen-specific IECs, such as antigen-specific T cells. This led the inventors to compare the effect of different oligomers of PD-L2 for blocking the binding of PD-L1 to PD1. Notably, it was found that a dimeric form of PD-L2 was not effective in blocking this binding. However, the present inventors also found that higher order PD-L2 oligomers, i.e., with degrees of oligomerization of 3 or more (e.g., 3, 4, 5, 6, 7, 8, 9, 10, 11, 12, etc.), have a significantly higher affinity than dimeric PD-L2 for binding to PD-1 and that such higher order PD-L2 oligomers can markedly reduce the suppressive effects of PD-L1 on IEC function, including CD4$^+$ T cell function. Accordingly, the present invention provides oligomers of PD-L2 with a degree of oligomerization of 3 or more (e.g., 3, 4, 5, 6, 7, 8, 9, 10, 11, 12, etc.) for use in modulating Th1 immunity and for treating Th1-related diseases, as described in more detail below.

Thus, the present invention provides polypeptide complexes that are useful for stimulating or enhancing Th1 immunity, which complexes are generally represented by formula (I):

$$[P]_n \quad (I)$$

wherein:

P, independently for each occurrence, represents a proteinaceous molecule comprising, consisting or consisting essentially of a PD-L2 polypeptide; and n represents an integer greater than 2.

2.1 PD-L2 Polypeptides

PD-L2 is a transmembrane protein and, in its monomeric form, comprises a signal peptide, IgV and IgC domains that make up the extracellular domain of the molecule (also referred to herein as "ectodomain"), with the IgV-like domain being responsible, in whole or in part, for PD-1 binding as well as other functions including signaling. PD-L2 also contains a short intracytoplasmic domain and a single transmembrane domain.

Non-limiting examples of PD-L2 proteins may be selected from the following PD-L2 orthologues:

Human PD-L2

[SEQ ID NO: 1]
MIFLLLMLSLELQLHQIAALFTVTVPKELYIIEHGSNVTLECNFDTGSH

VNLGAITASLQKVENDTSPHRERATLLEEQLPLGKASFHIPQVQVRDEG

QYQCIIIYGVAWDYKYLTLKVKASYRKINTHILKVPETDEVELTCQATG

YPLAEVSWPNVSVPANTSHSRTPEGLYQVTSVLRLKPPPGRNFSCVFWN

THVRELTLASIDLQSQMEPRTHPTWLLHIFIPFCIIAFIFIATVIALRK

QLCQKLYSSKDTTKRPVTTTKREVNSAI;

Chimpanzee PD-L2

[SEQ ID NO: 2]
MRWAKRSRYELRERDSMNHERWAKKAASPEVSDQIQNMIFLLLMLSLEL

QLHQIAALFTVTVPKELYIIEHGSNVTLECNFDTGSHVNLGAITASLQK

VENDTSPHCERATLLEEQLPLGKALFHIPQVQVRDEGQYQCIIIYGVAW

DYKYLTLKVKASYRKINTHILKVPETDEVELTCQATGYPLAEVSWPNVS

VPANTSHSRTPEGLYQVTSVLRLKPPPGRNFSCVFWNTHVRELTLASID

LQSQMEPRTHPTWLLHIFIPSCIIAFIFIATVIALRKQLCQKLYSSKDT

TKRPVTTTKREVNSAI;

Mouse PD-L2

[SEQ ID NO: 3]
MLLLLPILNLSLQLHPVAALFTVTAPKEVYTVDVGSSVSLECDFDRRECT

ELEGIRASLQKVENDTSLQSERATLLEEQLPLGKALFHIPSVQVRDSGQY

RCLVICGAAWDYKYLTVKVKASYMRIDTRILEVPGTGEVQLTCQARGYPL

AEVSWQNVSVPANTSHIRTPEGLYQVTSVLRLKPQPSRNFSCMFWNAHMK

ELTSAIIDPLSRMEPKVPRTWPLHVFIPACTIALIFLAIVIIQRKRI;

or a polypeptide having at least 70% (and at least 71% to 99% and all integer percentages in between) sequence similarity or identity to the sequence set forth in any one of SEQ ID NO: 1 to 3.

Useful PD-L2 polypeptides include soluble fragments, which are suitably fragments of PD-L2 that may be shed, secreted or otherwise extracted from the producing cells. In some embodiments, PD-L2 polypeptides include the entire ectodomain of PD-L2. The ectodomain of PD-L2 includes amino acids from about 20 to about amino acid 221 of mammalian PD-L2 or active fragments thereof. In other embodiments, PD-L2 polypeptides include the IgC and IgV domains of PD-L2. In still other embodiments, PD-L2 polypeptides include the IgV domain of PD-L2.

In specific embodiments, the PD-L2 polypeptide comprises, consists or consists essentially of a PD-L2 ectodomain, illustrative examples of which include:

Human PD-L2 Ectodomain Plus Signal Peptide

[SEQ ID NO: 4]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT;

Chimpanzee PD-L2 Ectodomain Plus Signal Peptide

[SEQ ID NO: 5]
MRWAKRSRYELRERDSMNHERWAKKAASPEVSDQIQNMIFLLLMLSLELQ

LHQIAALFTVTVPKELYIIEHGSNVTLECNFDTGSHVNLGAITASLQKVE

NDTSPHCERATLLEEQLPLGKALFHIPQVQVRDEGQYQCIIIYGVAWDYK

YLTLKVKASYRKINTHILKVPETDEVELTCQATGYPLAEVSWPNVSVPAN

TSHSRTPEGLYQVTSVLRLKPPPGRNFSCVFWNTHVRELTLASIDLQSQM

EPRTHPT;

Mouse PD-L2 Ectodomain Plus Signal Peptide

[SEQ ID NO: 6]
MLLLLPILNLSLQLHPVAALFTVTAPKEVYTVDVGSSVSLECDFDRRECT

ELEGIRASLQKVENDTSLQSERATLLEEQLPLGKALFHIPSVQVRDSGQY

RCLVICGAAWDYKYLTVKVKASYMRIDTRILEVPGTGEVQLTCQARGYPL

AEVSWQNVSVPANTSHIRTPEGLYQVTSVLRLKPQPSRNFSCMFWNAHMK

ELTSAIIDPLSRMEPKVPRT;

or

Human PD-L2 Ectodomain

[SEQ ID NO: 7]
LFTVTVPKELYIIEHGSNVTLECNFDTGSHVNLGAITASLQKVENDTSP

HRERATLLEEQLPLGKASFHIPQVQVRDEGQYQCIIIYGVAWDYKYLTL

KVKASYRKINTHILKVPETDEVELTCQATGYPLAEVSWPNVSVPANTSH

SRTPEGLYQVTSVLRLKPPPGRNFSCVFWNTHVRELTLASIDLQSQMEP

RTHPT;

Chimpanzee PD-L2 Ectodomain

[SEQ ID NO: 8]
LFTVTVPKELYIIEHGSNVTLECNFDTGSHVNLGAITASLQKVENDTSP

HCERATLLEEQLPLGKALFHIPQVQVRDEGQYQCIIIYGVAWDYKYLTL

KVKASYRKINTHILKVPETDEVELTCQATGYPLAEVSWPNVSVPANTSH

SRTPEGLYQVTSVLRLKPPPGRNFSCVFWNTHVRELTLASIDLQSQMEP

RTHPT;

Mouse PD-L2 Ectodomain

[SEQ ID NO: 9]
LFTVTAPKEVYTVDVGSSVSLECDFDRRECTELEGIRASLQKVENDTSL

QSERATLLEEQLPLGKALFHIPSVQVRDSGQYRCLVICGAAWDYKYLTV

KVKASYMRIDTRILEVPGTGEVQLTCQARGYPLAEVSWQNVSVPANTSH

IRTPEGLYQVTSVLRLKPQPSRNFSCMFWNAHMKELTSAIIDPLSRMEP

KVPRT;

or an ectodomain having at least 70% (and at least 71% to 99% and all integer percentages in between) sequence similarity or identity to the sequence set forth in any one of SEQ ID NO: 4 to 9.

In some embodiments, the PD-L2 polypeptide comprises at least a portion of a PD-L2 transmembrane domain.

Numerous other mammalian PD-L2 sequences, including primate sequences, are known in the art, as for example disclosed in the GenPept database or Onlamoon et al. (*Immunology* 124:277-293, 2008).

The proteinaceous molecules of the present invention may be oligomerized by any suitable means. For example, oligomers can be formed between proteinaceous molecules through chemical linkage, such as for example, by using heterobifunctional linkers, or through operable connection of oligomerization domains to the PD-L2 polypeptides of the proteinaceous molecules.

2.2 Heterobifunctional Linking Reagents

Linkage of a proteinaceous molecule to other proteinaceous molecules to create a polypeptide complex of the invention can be direct or indirect. For example, linkage of two or more proteinaceous molecules can be achieved by chemical linkage or facilitated by heterobifunctional linkers. Numerous heterobifunctional cross-linking reagents that are used to form covalent bonds between amino groups and thiol groups and to introduce thiol groups into proteins, are known to those of skill in this art (see, e.g., the PIERCE CATALOG, ImmunoTechnology Catalog & Handbook, 1992-1993, which describes the preparation of and use of such reagents and provides a commercial source for such reagents; see, also, e.g., Cumber et al. *Bioconjugate Chem.* 3:397-401, 1992; Thorpe et al. Cancer Res. 47:5924-5931, 1987; Gordon et al. *Proc. Natl. Acad Sci. USA* 84:308-312, 1987; Walden et al. *J. Mol. Cell Immunol.* 2:191-197, 1986; Carlsson et al. *Biochem. J.* 173: 723-737, 1978; Mahan et al. *Anal. Biochem.* 162:163-170, 1987; Wawrzynczak et al. *Br. J. Cancer* 66:361-366, 1992; Fattom et al. *Infection & Immun.* 60:584-589, 1992). These reagents can be used to form covalent bonds between a PD-L2 polypeptide and another PD-L2 polypeptide, and include, but are not limited to: N-succinimidyl-3-(2-pyridyldithio)propionate (SPDP; disulfide linker); sulfosuccinimidyl 6-[3-(2-pyridyldithio) propionamido]hexanoate (sulfo-LC-SPDP); succinimidyloxycarbonyl-α-methyl benzyl thiosulfate (SMBT, hindered disulfate linker); succinimidyl 6-[3-(2-pyridyldithio) propionamido]hexanoate (LC-SPDP); sulfosuccinimidyl 4-(N-maleimidomethyl)cyclohexane-1-carboxylate (sulfo-SMCC); succinimidyl 3-(2-pyridyldithio)butyrate (SPDB; hindered disulfide bond linker); sulfosuccinimidyl 2-(7-azido-4-methylcoumarin-3-acetamide)ethyl-1,3'-dithiopropionate (SAED); sulfo-succinimidyl 7-azido-4-methylcoumarin-3-acetate (SAMCA); sulfosuccinimidyl-6-[alpha-methyl-alpha-(2-pyridyldithio)toluamido]-hexanoate (sulfo-LC-SMPT); 1,4-di-[3'-(2'-pyridyldithio)propionamido] butane (DPDPB); 4-succinimidyloxycarbonyl-α-methyl-α-(2-pyridylthio)-toluene (SMPT, hindered disulfate linker); sulfosuccinimidyl-6-[α-methyl-α-(2-pyrimiyldi-thio)toluamido]-hexanoate (sulfo-LC-SMPT); m-maleimidobenzoyl-N-hydroxy-succinimide ester (MBS); m-maleimidobenzoyl-N-hydroxysulfo-succinimide ester (sulfo-MBS); N-succinimidyl(4-iodoacetyl)aminobenzoate (SIAB; thioether linker); sulfosuccinimidyl-(4-iodoacetyl)amino benzoate (sulfo-SIAB); succinimidyl-4-(p-maleimi-dophenyl)butyrate (SMPB); sulfosuccinimidyl-4-(p-maleimido-phenyl) buty-rate (sulfo-SMPB); azidobenzoyl hydrazide (ABH). These linkers, for example, can be used in combination with peptide linkers, such as those that increase flexibility or solubility or that provide for or eliminate steric hindrance. Any other linkers known to those of skill in the art for linking a polypeptide molecule to another molecule can be employed. General properties are such that the resulting molecule binds to PD-1 or to another target molecule (e.g., another cognate receptor).

2.3 Oligomerization Domains

Interaction of three or more PD-L2 polypeptides can be facilitated by their linkage, either directly or indirectly, to any moieties or other polypeptides that are themselves able to interact to form a stable structure. For example, separate PD-L2 polypeptide chains can be joined by oligomerization to form a proteinaceous molecule of the invention, whereby oligomerization of the polypeptides is mediated by an oligomerization domain. Typically, the oligomerization domain provides for the formation of a stable protein-protein interaction between at least 3, 4, 5, 6, 7, 8, 9, 10, 11, 12 or even more PD-L2 polypeptide-containing proteinaceous molecules. The oligomerization domain(s) of an individual PD-L2 polypeptide may be different to the oligomerization domain(s) of another PD-L2 polypeptide in a polypeptide complex of the invention, provided that the different oligomerization domains are 'complementary' such that they preferentially interact or associate with one another to permit oligomerization of the proteinaceous molecules (i.e., to form an oligomer such as a trimer, tetramer, pentamer, hexamer, heptamer, octamer, nonamer, decamer, undecamer, dodecamer, or higher order oligomer, which may be a homooligomer or heterooligomer).

Generally, an oligomerization domain includes any amino acid sequence capable of forming a stable protein-protein interaction. The oligomerization domains can interact via an immunoglobulin sequence (e.g. Fc domain; see e.g., International Patent Pub. Nos. WO 93/10151 and WO 2005/063816 US; U.S. Pub. No. 2006/0024298; U.S. Pat. No. 5,457,035), leucine zipper (e.g. from nuclear transforming proteins fos and jun or the proto-oncogene c-myc or from General Control of Nitrogen (GCN4)), a hydrophobic region, a hydrophilic region, or a free thiol which forms an intermolecular disulfide bond between the chimeric molecules of a homo- or heterooligomer. In addition, an oligomerization domain can include an amino acid sequence comprising a protuberance complementary to an amino acid sequence comprising a hole, such as is described, for example, in U.S. Pat. No. 5,731,168; International Patent Pub. Nos. WO 98/50431 and WO 2005/063816; Ridgway et al. (1996) Protein Engineering, 9:617-621. Such an oligomerization region can be engineered such that steric interactions not only promote stable interaction, but further promote the formation of heterodimers over homodimers from a mixture of chimeric monomers. Generally, protuberances are constructed by replacing small amino acid side chains from the interface of the first polypeptide with larger side chains (e.g., tyrosine or tryptophan). Compensatory cavities of identical or similar size to the protuberances are optionally created on the interface of the second polypeptide by replacing large amino acid side chains with smaller ones (e.g., alanine or threonine). Exemplary oligomerization domains are described below.

A PD-L2 polypeptide, such as for example any provided herein, can be joined anywhere, but typically via its N- or C-terminus, to the N- or C-terminus of an oligomerization module comprising at least one oligomerization domain to form a chimeric polypeptide. The linkage can be direct or indirect via a linker. Also, the chimeric polypeptide can be a fusion protein or can be formed by chemical linkage, such as through covalent or non-covalent interactions. For example, when preparing a chimeric polypeptide containing an oligomerization module comprising at least one oligomerization domain, nucleic acid encoding a PD-L2 polypeptide can be operably connected to nucleic acid encoding the oligomerization module, directly or indirectly or optionally via a linker peptide to form a nucleic acid construct. Typically, the construct encodes a chimeric polypeptide where the C-terminus of the PD-L2 polypeptide is joined to the N-terminus of the oligomerization module. In some instances, a construct can encode a chimeric polypeptide where the N-terminus of the PD-L2 polypeptide is joined to the C-terminus of an oligomerization domain.

For example, in embodiments in which at least one oligomerization domain is operably connected downstream of the PD-L2 polypeptide, the proteinaceous molecule may comprise, consist of consist essentially of a single polypeptide chain represented by formula (II):

$$\text{PD-L2-L-OMD}_A \tag{II}$$

wherein:

PD-L2 represents a PD-L2 polypeptide;

$OMD_A$ is an oligomerization domain that forms oligomers $(OMD_A)_i$ of i subunits $OMD_A$, wherein i is ≥3, suitably 3, 4, 5, or 6; and L is a bond or a peptide linker.

Alternatively, the proteinaceous molecule may comprise, consist of consist essentially of a single polypeptide chain represented by formula (III):

$$\text{PD-L2-L-OMD}_A\text{-L-OMD}_B \tag{III}$$

wherein:

$OMD_A$ is an oligomerization domain that forms oligomers $(OMD_A)_i$ of i subunits $OMD_A$, wherein i is ≥2, suitably 2, 3, 4, 5, or 6;

L, independently for each occurrence, represents a bond or a peptide linker; and $OMD_B$ is an oligomerization domain that forms oligomers $(OMD_B)_j$ of j subunits $OMD_B$, wherein j is an integer greater than i, suitably i+1, i+2, i+3, i+4, i+5, or i+6;

In embodiments in which at least one oligomerization domain is operably connected upstream of the PD-L2 polypeptide, the proteinaceous molecule may comprise, consist of consist essentially of a single polypeptide chain represented by formula (IV):

$$\text{OMD}_A\text{-L-PD-L2} \tag{IV}$$

wherein:
OMD$_A$ is an oligomerization domain that forms oligomers (OMD$_A$)$_i$ of i subunits OMD$_A$, wherein i is ≥3, suitably 3, 4, 5, or 6;
L is a bond or a peptide linker; and
PD-L2 represents a PD-L2 polypeptide.

Alternatively, the proteinaceous molecule may comprise, consist of consist essentially of a single polypeptide chain represented by formula (V):

OMD$_B$-L-OMD$_A$-L-PD-L2    (V)

wherein:
OMD$_B$ is an oligomerization domain that forms oligomers (OMD$_B$)$_j$ of j subunits OMD$_B$, wherein j is ≥2, suitably 2, 3, 4, 5, or 6;
L, independently for each occurrence, represents a bond or a peptide linker; and
OMD$_A$ is an oligomerization domain that forms oligomers (OMD$_A$)$_i$ of i subunits
OMD$_A$, wherein i is an integer greater than j, suitably j+1, j+2, j+3, j+4, j+5, or j+6; and PD-L2 represents a PD-L2 polypeptide.

Numerous oligomerization domains are known in the art, representative examples of which include:

2.3.1 Immunoglobulin Domain

Oligomerization domains include those comprising a free thiol moiety capable of reacting to form an intermolecular disulfide bond with an oligomerization domain of an additional amino acid sequence. For example, an oligomerization domain can include a portion of an immunoglobulin molecule, such as from IgG1, IgG2, IgG3, IgG4, IgA, IgD, IgM, or IgE. Generally, such a portion is an immunoglobulin constant region (Fc). Preparations of fusion proteins containing polypeptides fused to various portions of antibody-derived polypeptides (including the Fc domain) has been described, see e.g., Ashkenazi et al. *Proc. Natl. Acad. Sci USA* 88: 10535, 1991; Byrn et al. *Nature,* 344:667, 1990; and Hollenbaugh and Aruffo, (2002) "Construction of Immunoglobulin Fusion Proteins", in *Current Protocols in Immunology,* Ch. 10, pp. 10.19.1-10.19.11.

In some embodiments, an oligomerization domain comprises a full-length immunoglobulin polypeptide. Alternatively, the immunoglobulin polypeptide is less than full length, i.e. containing a heavy chain, light chain, Fab, Fab$_2$, Fv, or Fc. In one example, the PD-L2 polypeptide-immunoglobulin chimeric polypeptides are assembled as hetero- or homo-oligomers, and particularly as tetramers. Chains or basic units of varying structures can be utilized to assemble the hetero- and homo-oligomers. For example, a PD-L2 polypeptide can be fused to all or part of an immunoglobulin molecule, including all or part of C$_H$, C$_L$, V$_H$, or V$_L$ domain of an immunoglobulin molecule (see. e.g., U.S. Pat. No. 5,116,964). Chimeric PD-L2 polypeptide-immunoglobulin polypeptides can be readily produced and secreted by mammalian cells transformed with the appropriate nucleic acid molecule. The secreted forms include those where the PD-L2 polypeptide is present in heavy and light chain heterotetramers where the PD-L2 polypeptide is fused to one or more light or heavy chains, including heterotetramers where up to and including all four variable region analogues are substituted. In some examples, one or more than one nucleic acid fusion molecule can be transformed into host cells to produce an oligomer where the PD-L2 polypeptide portions of the oligomer are the same or different.

Fc Domain

Typically, the immunoglobulin portion of a PD-L2 polypeptide chimeric polypeptide includes the heavy chain of an immunoglobulin polypeptide, most usually the constant domains of the heavy chain. Exemplary sequences of heavy chain constant regions for human IgG sub-types are set forth selected from the following sequences:

```
                                              [SEQ ID NO: 10]
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK (IgG1);

[SEQ ID NO: 11]
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK (IgG2);

[SEQ ID NO: 12]
ASTKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVEL

KTPLGDTTHTCPRCPEPKSCDTPPPCPRCPEPKSCDTPPPCPRCPEPKSC

DTPPPCPRCPAPELLGGPSVFLFPPKPKDTLMISRTPEVTCVVVDVSHED

PEVQFKWYVDGVEVHNAKTKPREEQYNSTFRVVSVLTVLHQDWLNGKEYK

CKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQG

NIFSCSVMHEALHNRFTQKSLSLSPGK (IgG3);
and

[SEQ ID NO: 13]
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK (IgG4),
``` wherein the C$_{H1}$ domain corresponds to amino acids 1-98, the hinge region corresponds to amino acids 99-110, the C$_{H2}$ domain corresponds to amino acids 111-223, and the C$_{H3}$ domain corresponds to amino acids 224-330.

In one example, an immunoglobulin polypeptide chimeric protein can include the Fc region of an immunoglobulin polypeptide. Typically, such a fusion retains at least a functionally active hinge, C$_{H2}$ and C$_{H3}$ domains of the constant region of an immunoglobulin heavy chain. For example, a full-length Fc sequence of IgG1 includes amino acids 99-330 of the sequence set forth in SEQ ID NO: 10. An exemplary Fc sequence for human IgG1 is:

[SEQ ID NO: 14]
PKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSR

WQQGNVFSCSVMHEALHNHYTQKSLSLSPGK, which contains almost all of the hinge sequence, and the complete sequence for the $C_{H2}$ and $C_{H3}$ domain as set forth in SEQ ID NO: 10.

Alternatively, an Fc polypeptide for human IgG1 is selected from:

[SEQ ID NO: 15]
TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYP

SDIAVEWESNGQPENNYKTTPPVLDSDGPFFLYSKLTVDKSRWQQGNVFS

CSVMHEALHNHYTQKSLSLSPGK;
and

[SEQ ID NO: 16]
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

In addition to human IgG1 Fc, other Fc regions also can be included in the PD-L2 polypeptide-oligomerization module chimeric proteins provided herein. For example, where immune effector functions mediated by Fc/Fcγ receptor (Fc/FcγR) interactions are to be minimized, fusion with IgG isotypes that poorly recruit complement or immune effector cells, such as for example, the Fc of IgG2 or IgG4, is contemplated. Additionally, the Fc fusions can contain immunoglobulin sequences that are substantially encoded by immunoglobulin genes belonging to any of the antibody classes, including, but not limited to IgG (including human subclasses IgG1, IgG2, IgG3, or IgG4), IgA (including human subclasses IgA1 and IgA2), IgD, IgE, and IgM classes of antibodies. Further, linkers can be used to covalently link Fc to another polypeptide to generate a Fc chimera.

Modified Fc domains also are contemplated herein for use in chimeras with PD-L2 polypeptides. In some examples, the Fc region is modified such that it exhibits altered binding to an FcR so has to result altered (i.e., more or less) effector function than the effector function of an Fc region of a wild-type immunoglobulin heavy chain. Thus, a modified Fc domain can have altered affinity, including but not limited to, increased or low or no affinity for the Fc receptor. For example, the different IgG subclasses have different affinities for the FcγRs, with IgG1 and IgG3 typically binding substantially better to the receptors than IgG2 and IgG4.

Modified Fc domains are known to one of skill in the art and described in the literature, see e.g. U.S. Pat. No. 5,457,035; U.S. Patent Publication No. US 2006/0024298; and International Patent Publication No. WO 2005/063816 for exemplary modifications.

2.3.2 Coiled Coil Domains

One common structural motif involved in protein oligomerization is the coiled-coil domain and such domains can also be used as oligomerization domains for making PD-L2 polypeptide complexes. The coiled α-helix structural motif can itself form coils, and two, three, four or five α-helices can wrap around each other to form a left-handed super-helix known as the "coiled coil" though artificial right-handed super helices have been designed (Burkhard et al., *Trends Cell Biol* 11:82-88, 2001; Section 5.5.2 of Proteins by Creighton (ISBN 0-7167-2317-4); Yu *AdV Drug Deliv Rev* 54:1113-1129, 2002; Muller et al., *Methods Enzymol* 328:261-282, 2000; Beck & Brodsky J Struct Biol 122:17-29, 1998; Lupas *Trends Biochem Sci* 21:375-382, 1996; Adamson et al., Curr Opin Biotechnol 4:428-347, 1993). The simplicity of the coiled-coil domain has made it a popular choice for designing chimeric proteins with defined oligomerization states (Muller et al., *Methods Enzymol* 328:261-282, 2000).

In a coiled-coil structure the α-helices interact through hydrophobic residues that form an apolar stripe along one side of each helix, and there may also be stabilizing electrostatic interactions between side chains on either side of this stripe. Within the abcdefg heptad repeat of an α-helix, the apolar stripe is defined by hydrophobic side chains at residues a and d, with any electrostatic interactions being primarily at residues e and g. Position a is most frequently Leu, Ile or Ala and position d is usually Leu or Ala. Residues e and g are often Glu or Gin, with Arg and Lys also prominent at position g. Charged residues are common at positions b, c and f as these residues are in contact with solvent. There are exceptions to this general heptad pattern, however, and Pro residues are sometimes found within the heptad. Such exceptions usually have functional significance including, by way of example, destabilization of the oligomerization domain to allow refolding and rearrangement such as occurs in the F protein.

Hundreds of coiled-coil domain sequences are known in the art, and any suitable sequence can be used as an oligomerization domain with the invention, provided that it retains the ability to oligomerize with other coiled-coil domains and that it does not destroy or significantly impair the function of the other domains within the PD-L2 polypeptide. As an alternative to using a natural coiled-coil domain, artificial coiled-coil domains can be used (Chao et al., *J Chromatog B Biomed Sci Appl* 715:307-329, 1998; Arndt et al., *Structure* 10:1235-1248, 2002). Owing to the highly repetitive structure of a coiled-coil domain, the domain is particularly amenable to computer modeling as the backbone portions of each amino acid residue may be parameterized rather than treating each backbone portion of a residue as a unique unit with its own variables. Domain (b) may include a leucine zipper sequence or an alanine zipper sequence (Liu & Lu *J Biol Chem* 277:48708-48713, 2002).

Coiled coils have been shown to exist as dimers, trimers, tetramers and pentamers. They have been found in many types of proteins, including transcription factors such as, but not limited to fos, jun, c-myc, GCN4, viral fusion peptides, SNARE complexes and certain tRNA synthetases, among others. Very long coiled coils are found in proteins such as tropomyosin, intermediate filaments and spindle-pole-body components. Other examples are the thrombospondins and cartilage oligomeric matrix protein (COMP) in which three (thrombospondins 1 and 2) or five (thrombospondins 3, 4 and COMP) chains are connected. The molecules have a flower bouquet-like appearance, and the reason for their oligomeric structure is probably the multivalent interaction of the C-terminal domains with cellular receptors. The yeast transcriptional activator GCN4 is 1 of over 30 identified eukaryotic proteins containing the basic region leucine zipper (bZIP) DNA-binding motif Ellenberger et al. (Cell 71: 1223-1237, 1982). The bZIP dimer is a pair of continuous alpha helices that form a parallel coiled-coil over their carboxy-terminal 34 residues and gradually diverge toward their amino termini to pass through the major groove of the DNA binding site. Another example is CMP (matrilin-1) isolated from bovine tracheal cartilage as a homotrimer of subunits of Mr 52,000 (Paulsson and Heinegard *Biochem J.* 197: 367-375, 1981), where each subunit consists of a vWFA1 module, a single EGF domain, a vWFA2 module and a coiled coil domain spanning five heptads (Kiss et al. *J. Biol. Chem.* 264:8126-8134, 1989; Hauser and Paulsson *J. Biol. Chem.* 269: 25747-25753, 1994). Yet another example is Cartilage Oligomeric Matrix Protein (COMP). A non-collagenous glycoprotein, COMP, was first identified in cartilage (Hedbom, et al. *J. Biol. Chem.* 267:6132-6136, 1992). The protein is a 524 kDa homopentamer of five subunits which consists of an N-terminal heptad repeat region (cc) followed by four epidermal growth factor (EGF)-like domains (EF), seven calcium-binding domains (T3) and a C-terminal globular domain (TC). According to this domain organization, COMP belongs to the family of thrombospondins.

In specific embodiments, the coiled coil oligomerization domains are leucine zippers. The dimer formed by a leucine zipper domain is stabilized by the heptad repeat, designated (abcdefg)n (see e.g., McLachlan and Stewart, *J. Mol. Biol.* 98:293, 1978), in which residues a and d are generally hydrophobic residues, with d being a leucine, which lines up on the same face of a helix. Oppositely-charged residues commonly occur at positions g and e. Thus, in a parallel coiled coil formed from two helical leucine zipper domains, the "knobs" formed by the hydrophobic side chains of the first helix are packed into the "holes" formed between the side chains of the second helix.

Illustrative leucine zippers for use as oligomerization domains herein can be derived from either of two nuclear transforming proteins, fos and jun, that exhibit leucine zipper domains, or the product of the murine proto-oncogene, c-myc. The leucine zipper domain is necessary for biological activity (DNA binding) in these proteins. The products of the nuclear oncogenes fos and jun contain leucine zipper domains that preferentially form a heterodimer (O'Shea et al. *Science,* 245:646, 1989; Turner and Tijian *Science,* 243:1689, 1989). For example, the leucine zipper domains of the human transcription factors c-jun and c-fos have been shown to form stable heterodimers with a 1:1 stoichiometry (see e.g., Busch and Sassone-Corsi, *Trends Genetics,* 6:36-40, 1990; Gentz et al., *Science,* 243:1695-1699, 1989). Although jun-jun homodimers also have been shown to form, they are about 1000-fold less stable than jun-fos heterodimers.

Generally, the leucine zipper domain of either c-jun or c-fos is fused at the C-terminus of a PD-L2 polypeptide. Exemplary amino acid sequences of c-jun and c-fos leucine zippers include:

```
                                          [SEQ ID NO: 17]
    RIARLEEKVKTLKAQNSELASTANMLREQVAQLKQKVMN;
and

[SEQ ID NO: 18]
    LTDTLQAETDQLEDEKSALQTEIANLLKEKEKLEFILAA,
``` respectively.

In addition, the linkage of an PD-L2 polypeptide with a leucine zipper can be direct or can employ a flexible linker domain, such as for example a hinge region of IgG, or other polypeptide linkers of small amino acids such as glycine, serine, threonine, or alanine at various lengths and combinations, as described in more detail below. In some instances, separation of a leucine zipper from the C-terminus of an encoded polypeptide can be effected by fusion with a sequence encoding a protease cleavage site, such as for example, a thrombin cleavage site.

Another exemplary leucine zipper domain for use as an oligomerization domain is derived from a nuclear protein that functions as a transcriptional activator of a family of genes involved in the General Control of Nitrogen (GCN4) metabolism in *Saccharomyces cerevisiae*. The protein is able to dimerize and bind promoter sequences containing the recognition sequence for GCN4, thereby activating transcription in times of nitrogen deprivation. Such domains are known in the art (O'Shea et al., *Science* 243, 534-542, 1989; Harbury et al., *Science* 262, 1401-1407, 1993). An exemplary sequence of a GCN4 leucine zipper capable of forming a dimeric complex is suitable selected from:

```
                                          [SEQ ID NO: 19]
    RMKQLEDKVEELLSKNYHLENEVARLKKLVGE;
and

[SEQ ID NO: 20]
    MKQLEDKVEELLSKNYHLENEVARLKKLVGER.
```

Amino acid substitutions in the a and d residues of a synthetic peptide representing the GCN4 leucine zipper domain (i.e., amino acid substitutions in the sequence set forth as SEQ ID NO: 16) have been found to change the oligomerization properties of the leucine zipper domain. For example, when all residues at position a are changed to isoleucine, the leucine zipper still forms a parallel dimer. When, in addition to this change, all leucine residues at position d also are changed to isoleucine, the resultant peptide spontaneously forms a trimeric parallel coiled coil in solution. An exemplary sequence of such a GNC4 leucine zipper domain capable of forming a trimer is selected from:

```
                                          [SEQ ID NO: 21]
    RMKQIEDKIEEILSKIYHIENEIARIKKLIGE;
and

[SEQ ID NO: 22]
    MKQIEDKIEEIESKQKKIENEIARIKK.
```

Substituting all amino acids at position d with isoleucine and at position a with leucine results in a peptide that tetramerizes. A representative sequence of a leucine zipper domain of GCN4 capable of forming tetramers is suitably selected from:

```
                                               [SEQ ID NO: 23]
    RMKQIEDKLEEILSKLYHIENELARIKKLLGE;
    and

[SEQ ID NO: 24]
    MKQIEDKLEEILSKLYHIENELARIKKLLGE.
```

Peptides containing these substitutions are still referred to as leucine zipper domains since the mechanism of oligomer formation is believed to be the same as that for traditional leucine zipper domains such as the GCN4 described above and set forth in SEQ ID NO:16.

Alternative coiled-coil domains are those taken from bacterial transmembrane proteins, which form trimers. A suitable subset of transmembrane proteins is the adhesins (i.e., cell-surface proteins that mediate adhesion to other cells or to surfaces), and particularly non-fimbrial adhesins (e.g., in the oligomerization coiled-coil adhesins, or 'Oca', family). Specific sequences for use with the invention include those disclosed in reference 24 from *Yersinia enterocolitica* adhesin YadA, *Neisseria meningitidis* adhesin NadA, *Moraxella catarrhalis* surface protein UspA2, and other adhesins, such as the HadA adhesin from *Haemophilus influenzae* biogroup *aegyptius* etc. (see, SEQ ID NOs 28-31 and 42-58 of WO2006/011060). In addition, the eukaryotic heat-shock transcription factor has a coiled-coil trimerization domain that can be separately expressed and therefore used with the invention.

Another class of oligomerization domain that can be used with the invention is found in the left-handed triple helix known as the collagen helix (Section 5.5.3 of Proteins by Creighton (ISBN 0-7167-2317-4). These triple helix-forming sequences involve a basic tripeptide repeat sequence of $^1$Gly$^2$Xaa$^3$Xaa, where $^2$Xaa is often Pro, and $^3$Xaa is often 4-hydroxyproline. Although this motif is known as the "collagen" helix, it is found in many proteins beyond just collagen. The oligomerization domain may thus be a sequence comprising multiple repeats of the sequence motif $^1$Gly$^2$Xaa$^3$Xaa, which motif folds to form a helical structure that can oligomerize with corresponding helical structures in other polypeptide chains.

Collagen also provides another class of oligomerization domain. Zhang & Chen (*J Biol Chem* 274:22409-22413, 1999) describe a motif found in the non-collagenous domain 1 (NC1) of type X collagen, and this motif can be used for trimer and higher order oligomer formation without a triple helix. This trimeric association is highly thermostable without intermolecular disulfide bonds. The oligomerization domain may thus comprise an NC1 sequence.

The trimerization domain (foldon) of the bacteriophage T4 protein fibritin (Tao et al., *Structure* 5:789-798, 1997; Gu the et al. *J. Mol. Biol.* 337, 905-915, 2004), in particular the C-terminal 27 to 30 residues of foldon, or a derivative thereof, may also be used to oligomerize a PD-L2 polypeptide. This trimerization domain may have the sequence GYIPEAPRDGQAYVRKDGEWVLLSTFL [SEQ ID NO: 25] or GSGYIPEAPRDGQAYVRKDGEWVLLSTFL [SEQ ID NO: 26]. Small modifications of this domain are also envisaged. Such modifications may be the substitution of Asp 9 by Cys for the purpose of the formation of a disulfide bridge between adjacent domains. Other modifications of surface amino acids of this domain may include substitutions of residues for optimizing the interactions at the interface between adjacent oligomerization domains such as hydrophobic, hydrophilic or ionic interactions or covalent bonds like disulfide bridges. Yet other modifications of surface amino acids of this domain may include substitutions of amino acids (e.g. by cysteine or lysine) for the generation of attachment sites for functional groups.

In other embodiments, the tetramerization domain of the coiled-coil domain of tetrabrachion (Stetefeld et al., *Nature Structural Biology* 7(9):772-776, 2000) or a derivative thereof, is employed for oligomerizing a PD-L2 polypeptide. This tetramerization domain suitably comprises the sequence IINETADDIVYRLTVIIDDRYESLKNLITL-RADRLMIINDNVSTILASG [SEQ ID NO: 27]. The sequences of coiled coils are characterized by a heptad repeat of seven residues with a 3,4-hydrophobic repeat. The next periodicity that allows residues to assume quasi-equivalent positions after a small number of turns is three turns or 11 residues. Based on the presence of 11-residue repeats, the C-terminus of the surface layer glycoprotein tetrabrachion from the hyperthermophilic archae-bacterium *Staphylothermus marinus* forms a right-handed coiled coil structure. It forms a tetrameric α-helical coiled coil stalk 70 nm long that is anchored to the cell membrane at its C-terminal end.

The present invention also contemplates pentamerization domains for oligomerizing PD-L2 polypeptides. A non-limiting domain of this type is the pentamerization domain of COMP (Malashkevich et al., *Science* 274:761-765, 1996) or a derivative thereof. This pentamerization domain may comprise the sequence LAPQMLRELQET-NAALQDVRELLRQQVKQITFLKNTVMECDACG [SEQ ID NO: 28]. Shorter constructs of this sequence, e.g. lacking the C-terminal CDACG motif in which the cysteines form intermolecular disulfide bridges at the C-terminus of this pentamerization domain are also envisaged.

Alternatively, the pentamerization domain is of the tryptophane zipper (Liu J et al., *Proc Natl Acad Sci USA* 101:16156-16161, 2004) or a derivative thereof. A non-limiting pentamerization domain of this type comprises the sequence

```
                                               [SEQ ID NO: 29]
    SSNAKWDQWSSDWQTWNAKWDQWSNDWNAWRSDWQAWKDD WARWN
    QRWDNWAT.
```

Another useful oligomerization domain is C-terminus of the heavy chain of an IgA immunoglobulin, also known as an alpha tailpiece (atp), which forms hexamers. A representative hexamerizing atp sequence is 18 amino acids in length and is derived from a human IgA molecule. In one embodiment, an alpha tailpiece is PTHVNVSVVMAEVDGTCY [SEQ ID NO: 30]. However, if desired the peptide may be modified to remove the glycosylation site by changing 1 or 2 amino acids at residues 5-7 (NVS). For example, the asparagine (N) at position 5 can be changed to a glutamine (Q). Alternatively, the serine (S) at position 7 can be changed to an alanine (A). Additionally, a few of the amino acids residues of the IgA constant region may also be included, such as about four amino acids of the IgA constant region. Suitable IgA molecules, having an alpha tailpiece of use include, but are not limited to, human IgA1, human IgA2, rabbit IgA, and mouse IgA. This peptide is linked, either directly or indirectly to a constant domain of an immunoglobulin, such as a fragment including the $C_{H2}$ and $C_{H3}$ domains.

2.3.3 Protein-Protein Interaction Between Subunits

Alternative oligomerization domains for use in oligomerizing a PD-L2 polypeptide are ones where oligomerization is facilitated by protein-protein interactions between different subunit polypeptides. Such oligomerization domains for example are derived from the mechanism of cAMP-dependent protein kinase (PKA) with its anchoring domain (AD) of A kinase anchor proteins (AKAP). Thus, a heterooligomeric PD-L2 polypeptide can be generated by fusing (directly or indirectly) a PD-L2 polypeptide with a an R subunit sequence of PKA, an illustrative example of which is: SHIQIPPGLTELLQGYTVEVLRQQPPDLVE-FAVEYFTRLREARA [SEQ ID NO: 31]. This results in a homodimeric molecule, due to the spontaneous formation of a dimer effected by the R subunit. In tandem, another PD-L2 polypeptide fusion can be generated by fusing a another PD-L2 polypeptide to an AD sequence of AKAP, which comprises for example the sequence: QIEYLAKQIVD-NAIQQ [SEQ ID NO: 32]. Upon co-expression of a coding sequence for each of these chimeric polypeptides in host cells, the dimeric R subunit provides a docking site for binding to the AD sequence, resulting in a heterooligomeric molecule. This binding event can be further stabilized by covalent linkages, such as for example, disulfide bonds. In some examples, a flexible linker residue can be fused between the PD-L2 polypeptide and the oligomerization domain. In another example, fusion of a PD-L2 polypeptide can be to an R subunit containing a cysteine residue incorporated adjacent to the amino-terminal end of the R subunit to facilitate covalent linkage. Such a modified R subunit of PKA may comprise for example the sequence: CSHIQIPPGLTELLQGYTVEVLRQQPPDLVE-FAVEYFTRLREARA [SEQ ID NO: 33]. Similarly, fusion of a PD-L2 polypeptide can be to an AD subunit also containing incorporation of cysteine residues to both the amino- and carboxyl-terminal ends of AD. An representative sequence for such a modified AD subunit comprises the sequence: CGQIEYLAKQIVDNAIQQAGC [SEQ ID NO: 34].

Other oligomerization domains that can be used to oligomerize PD-L2 polypeptides, which facilitate the protein-protein interaction of two or more polypeptides that are separately generated and expressed as PD-L2 polypeptide fusions include, for example, the barnase-barstar module (see, e.g., Deyev et al., *Nat. Biotechnol.* 21:1486-1492, 2003); use of particular protein domains (see, e.g., Terskikh et al., *Proc Natl Acad Sci USA* 94: 1663-1668, 1997; and Muller et al., *FEBS Lett.* 422:259-264, 1998); use of particular peptide motifs (see, e.g., de Kruif et al., *J. Biol. Chem.* 271:7630-7634, 1996; and Muller et al., *FEBS Lett.* 432: 45-49, 1998); and the use of disulfide bridges for enhanced stability (de Kruif et al., *J. Biol. Chem.* 271:7630-7634, 1996; and Schmiedl et al., *Protein Eng.* 13:725-734, 2000), as well as specific binding pairs such as biotin-avidin, biotin-streptavidin, antigen-antibody, hapten-anti-hapten, ligand-receptor and receptor-co-receptor.

2.4 Linkers

The chimeric polypeptides of the present invention may comprise a linker that spaces the PD-L2 polypeptide from an oligomerization domain or that spaces two oligomerization domains. The linker generally includes any amino acid residue that cannot be unambiguously assigned to a heptad repeat sequence. Linkers are frequently used in the field of protein engineering to interconnect different functional units, e.g., in the creation of single-chain variable fragment (scFv) constructs derived from antibody variable light (VL) and variable heavy (VH) chains. They are generally conformationally flexible in solution, and are suitably and predominantly composed of polar amino acid residue types. Typical (frequently used) amino acids in flexible linkers are serine and glycine. Less preferably, flexible linkers may also include alanine, threonine and proline. Thus, an intervening linker of a chimeric polypeptide is preferably flexible in conformation to ensure relaxed (unhindered) association of a PD-L2 polypeptide and an oligomerization domain or of two oligomerization domains. Suitable linkers for use in the polypeptides envisaged herein will be clear to the skilled person, and may generally be any linker used in the art to link amino acid sequences, as long as the linkers are structurally flexible, in the sense that they do not affect a biological activity of the PD-L2 polypeptide or the oligomerizing properties of an oligomerization domain.

The skilled person will be able to determine the optimal linkers, optionally after performing a limited number of routine experiments. The intervening linker is suitably an amino acid sequence generally consisting of at least 1 amino acid residue and usually consisting of at least 2 amino acid residues, with a non-critical upper limit chosen for reasons of convenience being about 100 amino acid residues. In particular embodiments, the linker consists of about 1 to about 50 amino acid residues, or about 50 to about 100 amino acid residues, usually about 1 to about 40 amino acid residues, typically about 1 to about 30 amino acid residues. In particular, non-limiting embodiments, at least 50% of the amino acid residues of a linker sequence are selected from the group proline, glycine, and serine. In further non-limiting embodiments, at least 60%, such as at least 70%, such as for example 80% and more particularly 90% of the amino acid residues of a linker sequence are selected from the group proline, glycine, and serine. In other particular embodiments, the linker sequences essentially consist of polar amino acid residues; in such particular embodiments, at least 50%, such as at least 60%, such as for example 70% or 80% and more particularly 90% or up to 100% of the amino acid residues of a linker sequence are selected from the group consisting of glycine, serine, threonine, alanine, proline, histidine, asparagine, aspartic acid, glutamine, glutamic acid, lysine and arginine. In some embodiments, linker sequences may include GG, $[GGSG]_n$GG, $[GGGGS]_n$, $[SSSSG]_n$, $[SSSSG]_n$, $[AAPA]_n$, $[GGGKGGGG]_n$, $[GGGNGGGG]_n$, $[GGGCGGGG]_n$, wherein n is an integer from 1 to 10, suitably 1 to 5, more suitably 1 to 3.

In specific embodiments, exemplary linkers may be selected from: GGGGG [SEQ ID NO:35], GGGGS [SEQ ID NO:36], SSSSG [SEQ ID NO:37], GKSSGSGSESKS [SEQ ID NO:38], GSTSGSGKSSSEGSGSTKG [SEQ ID NO: 39], GSTSGSGKPGSGEGSTKG [SEQ ID NO: 40], EGKSSGSGSESKEF [SEQ ID NO: 41], GGST-SGSGKSSEGKG [SEQ ID NO: 42], AAPA [SEQ ID NO:43].

2.5 Other Moieties

The chimeric polypeptides of the present invention may further include purification moieties to facilitate purification of the PD-L2 polypeptide-oligomerization domain chimeras. Purification moieties typically comprise a stretch of amino acids that enables recovery of the chimeric polypeptide through affinity binding. Numerous purification moieties or 'tags' are known in the art, illustrative examples of which include biotin carboxyl carrier protein-tag (BCCP-tag), Myc-tag (c-myc-tag), Calmodulin-tag, FLAG-tag, HA-tag, His-tag (Hexahistidine-tag, His6, 6H), Maltose binding protein-tag (MBP-tag), Nus-tag, Cellulose binding domain-tag (CBD-tag), T7 peptide-tag (T7-tag), Ubiquitin-tag, Chitin-binding protein-tag (CBP-tag) Glutathione-S-transferase-tag (GST-tag), Green fluorescent protein-tag (GFP-tag), Polyglutamate-tag, Amyloid beta-tag, Thioredoxin-tag, S-tag, Softag 1, Softag 3, Staphylococcal protein A-tag (Protein A-tag), Streptococcal protein G-tag (Protein G-tag), Streptavidin-binding peptide-tag (SBP-tag), biotin-tag, streptavidin-tag and V5-tag.

In some embodiments, the PD-L2 polypeptide and/or oligomerization domain(s) includes an immune-silencing or suppressing moiety that inhibits elicitation or production of an immune response in a subject to any one or more of those constituents. The immune-silencing moiety can be a glycosylation site that is specifically recognized and glycosylated by a glycosylation enzyme, in particular a glycosyltransferase. Glycosylations can be N-linked or O-linked. N-linked refers to the attachment of the carbohydrate moiety to the side chain of an asparagine residue. The tripeptide sequences N—X—S and N—X-T, where X is any amino acid except P, are the recognition sequences for enzymatic attachment of the carbohydrate moiety to the asparagine side chain, and these sequences are commonly referred to as 'glycosylation sites'. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

3. Representative Chimeric Polypeptide Constructs

Exemplary chimeric polypeptides of the present invention are suitably represented by the formula (VI):

PD-L2-L-OMD$_X$ (VI)

wherein:

PD-L2 is selected from any one of SEQ ID NO: 1 to 9, or a polypeptide having at least 70% (and at least 71% to 99% and all integer percentages in between) sequence similarity or identity to the sequence set forth in any one of SEQ ID NO: 1 to 9;

-L- represents a bond (e.g., peptide bond) or a peptide linker selected from the group consisting of: [GGSG]$_n$, GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GSTSGSGKSSSEGSGSTKG [SEQ ID NO: 39], GSTSGSGKPGSGEGSTKG [SEQ ID NO: 40], EGKSSGSGSESKEF [SEQ ID NO: 41], GGSTSGSGKSSEGKG [SEQ ID NO: 42], and AAPA [SEQ ID NO:43]; and OMD$_X$ is selected from:
(a) a trimerization domain, which suitably comprises or consists of an amino acid sequence selected from any one of SEQ ID NO: 21, 22, 25 and 26, or a polypeptide having at least 70% (and at least 71% to 99% and all integer percentages in between) sequence similarity or identity to the sequence set forth in any one of SEQ ID NO: 21, 22, 25 and 26;
(b) a tetramerization domain, which suitably comprises or consists of an amino acid sequence selected from any one of SEQ ID NO: 23, 24 and 27, or a polypeptide having at least 70% (and at least 71% to 99% and all integer percentages in between) sequence similarity or identity to the sequence set forth in any one of SEQ ID NO: 23, 24 and 27;
(c) a pentamerization domain, which suitably comprises or consists of an amino acid sequence selected from SEQ ID NO: 28 or 29; and
(d) a hexamerization domain, which suitably comprises or consists of the amino acid sequence set forth in SEQ ID NO: 30.

In other embodiments, the chimeric polypeptides of the present invention are suitably represented by the formula (VII):

PD-L2-L-OMD$_Y$-L-OMD$_Z$ (VII)

wherein:

PD-L2 is selected from any one of SEQ ID NO: 1 to 9, or a polypeptide having at least 70% (and at least 71% to 99% and all integer percentages in between) sequence similarity or identity to the sequence set forth in any one of SEQ ID NO: 1 to 9;

-L-, independently for each occurrence, represents a bond (e.g., peptide bond) or a peptide linker selected from the group consisting of: [GGSG]$_n$GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GSTSGSGKSSSEGSGSTKG [SEQ ID NO: 39], GSTSGSGKPGSGEGSTKG [SEQ ID NO: 40], EGKSSGSGSESKEF [SEQ ID NO: 41], GGSTSGSGKSSEGKG [SEQ ID NO: 42], and AAPA [SEQ ID NO:43];

OMD$_Y$ is an oligomerization domain that forms oligomers (OMD$_Y$)$_i$ of i subunits OMD$_Y$, and is suitably selected from:
(a) a dimerization domain, which suitably comprises or consists of an amino acid sequence selected from any one of SEQ ID NO: 10, 11, 12, 13, 14, 15, 16, 17, 18, 19 and 20, or a polypeptide having at least 70% (and at least 71% to 99% and all integer percentages in between) sequence similarity or identity to the sequence set forth in any one of SEQ ID NO: 10, 11, 12, 13, 14, 15, 16, 17, 18, 19 and 20, or which comprises or consists of an oligomerizing domain that is a member of a specific binding pair that is suitably selected from R subunit sequence of PKA-AD sequence of AKAP (e.g., SEQ ID NO: 31 and 32 or SEQ ID NO: 33 and 34), biotin-avidin, biotin-streptavidin, antigen-antibody, hapten-anti-hapten, ligand-receptor and receptor-co-receptor;
(b) a trimerization domain, which suitably comprises or consists of an amino acid sequence selected from any one of SEQ ID NO: 21, 22, 25 and 26, or a polypeptide having at least 70% (and at least 71% to 99% and all integer percentages in between) sequence similarity or identity to the sequence set forth in any one of SEQ ID NO: 21, 22, 25 and 26;
(c) a tetramerization domain, which suitably comprises or consists of an amino acid sequence selected from any one of SEQ ID NO: 23, 24 and 27, or a polypeptide having at least 70% (and at least 71% to 99% and all integer percentages in between) sequence similarity or identity to the sequence set forth in any one of SEQ ID NO: 23, 24 and 27;
(d) a pentamerization domain, which suitably comprises or consists of an amino acid sequence selected from SEQ ID NO: 28 or 29; and
(e) a hexamerization domain, which suitably comprises or consists of the amino acid sequence set forth in SEQ ID NO: 30; and OMD$_Z$ is an oligomerization domain that forms oligomers (OMD$_Z$)$_j$ of j subunits OMD$_Z$, wherein j is an integer greater than i, suitably i+1, i+2, i+3, i+4, i+5, or i+6, and wherein OMD$_Z$ is suitably selected from:

(a) a trimerization domain, which suitably comprises or consists of an amino acid sequence selected from any one of SEQ ID NO: 21, 22, 25 and 26, or a polypeptide having at least 70% (and at least 71% to 99% and all integer percentages in between) sequence similarity or identity to the sequence set forth in any one of SEQ ID NO: 21, 22, 25 and 26;
(b) a tetramerization domain, which suitably comprises or consists of an amino acid sequence selected from any one of SEQ ID NO: 23, 24 and 27, or a polypeptide having at least 70% (and at least 71% to 99% and all integer percentages in between) sequence similarity or identity to the sequence set forth in any one of SEQ ID NO: 23, 24 and 27;
(c) a pentamerization domain, which suitably comprises or consists of an amino acid sequence selected from SEQ ID NO: 28 or 29; and
(d) a hexamerization domain, which suitably comprises or consists of the amino acid sequence set forth in SEQ ID NO: 30; and Non-limiting examples of chimeric polypeptides of the present invention are set out below:

3.1 Human PD-L2 Ectodomain-L-GCN4 Trimerization Domain

[SEQ ID NO: 44]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT-L-RMKQIEDKIEEILSKIYHIENEIARIK

KLIGE, wherein:
-L- represents a bond (e.g., peptide bond) or a peptide linker selected from the group consisting of: [GGSG]$_n$ GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GST-SGSGKSSSEGSGSTKG [SEQ ID NO: 39], GST-SGSGKPGSGEGSTKG [SEQ ID NO: 40], EGKSSGSGSESKEF [SEQ ID NO: 41], GGST-SGSGKSSEGKG [SEQ ID NO: 42], and AAPA [SEQ ID NO:43].

The GCN4 trimerization domain facilitates self-assembly of the chimeric polypeptide into trimers.

3.2 Human PD-L2 Ectodomain-L-Foldon Trimerization Domain

[SEQ ID NO: 45]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT-L-GSGYIPEAPRDGQAYVRKDGEWVLLST

FL, wherein:
-L- represents a bond (e.g., peptide bond) or a peptide linker selected from the group consisting of: [GGSG]$_n$ GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GST-SGSGKSSSEGSGSTKG [SEQ ID NO: 39], GST-SGSGKPGSGEGSTKG [SEQ ID NO: 40], EGKSSGSGSESKEF [SEQ ID NO: 41], GGST-SGSGKSSEGKG [SEQ ID NO: 42], and AAPA [SEQ ID NO:43].

The foldon trimerization domain facilitates self-assembly of the chimeric polypeptide into trimers.

3.3 Human PD-L2 Ectodomain-L-GCN4 Tetramerization Domain

[SEQ ID NO: 46]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT-L-RMKQIEDKLEEILSKLYHIENELARIK

KLLGE, wherein:
-L- represents a bond (e.g., peptide bond) or a peptide linker selected from the group consisting of: [GGSG]$_n$ GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GST-SGSGKSSSEGSGSTKG [SEQ ID NO: 39], GST-SGSGKPGSGEGSTKG [SEQ ID NO: 40], EGKSSGSGSESKEF [SEQ ID NO: 41], GGST-SGSGKSSEGKG [SEQ ID NO: 42], and AAPA [SEQ ID NO:43].

The GCN4 tetramerization domain facilitates self-assembly of the chimeric polypeptide into tetramers.

3.4 Human PD-L2 Ectodomain-L-Tetrabrachion Tetramerization Domain

[SEQ ID NO: 47]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT-L-IINETADDIVYRLTVIIDDRYESLKNL

ITLRADRLMIINDNVSTILASG, wherein:
-L- represents a bond (e.g., peptide bond) or a peptide linker selected from the group consisting of: [GGSG]$_n$ GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GST-SGSGKSSSEGSGSTKG [SEQ ID NO: 39], GST-SGSGKPGSGEGSTKG [SEQ ID NO: 40], EGKSSGSGSESKEF [SEQ ID NO: 41], GGST-SGSGKSSEGKG [SEQ ID NO: 42], and AAPA [SEQ ID NO:43].

The tetrabrachion tetramerization domain facilitates self-assembly of the chimeric polypeptide into tetramers.

3.5 Human PD-L2 Ectodomain-L-COMP Pentamerization Domain

[SEQ ID NO: 48]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT-L-LAPQMLRELQETNAALQDVRELLRQQV

KQITFLKNTVMECDACG, wherein:
-L- represents a bond (e.g., peptide bond) or a peptide linker selected from the group consisting of: [GGSG]$_n$ GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GST-SGSGKSSSEGSGSTKG [SEQ ID NO: 39], GST-SGSGKPGSGEGSTKG [SEQ ID NO: 40], EGKSSGSGSESKEF [SEQ ID NO: 41], GGST-SGSGKSSEGKG [SEQ ID NO: 42], and AAPA [SEQ ID NO:43].

The COMP pentamerization domain facilitates self-assembly of the chimeric polypeptide into pentamers.

3.6 Human PD-L2 Ectodomain-L-Tryptophane Zipper Pentamerization Domain

[SEQ ID NO: 49]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT-L-SSNAKWDQWSSDWQTWNAKWDQWSNDW

NAWRSDWQAWKDDWARWNQRWDNWAT, wherein:
-L- represents a bond (e.g., peptide bond) or a peptide linker selected from the group consisting of: [GGSG]$_n$ GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GST-SGSGKSSSEGSGSTKG [SEQ ID NO: 39], GST-SGSGKPGSGEGSTKG [SEQ ID NO: 40], EGKSSGSGSESKEF [SEQ ID NO: 41], GGST-SGSGKSSEGKG [SEQ ID NO: 42], and AAPA [SEQ ID NO:43].

The tryptophane zipper pentamerization domain facilitates self-assembly of the chimeric polypeptide into pentamers.

3.7 Human PD-L2 Ectodomain-L-atp Hexamerization Domain

[SEQ ID NO: 50]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT-L-PTHVNVSVVMAEVDGTCY, wherein:
-L- represents a bond (e.g., peptide bond) or a peptide linker selected from the group consisting of: [GGSG]$_n$ GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GST-SGSGKSSSEGSGSTKG [SEQ ID NO: 39], GST-SGSGKPGSGEGSTKG [SEQ ID NO: 40], EGKSSGSGSESKEF [SEQ ID NO: 41], GGST-SGSGKSSEGKG [SEQ ID NO: 42], and AAPA [SEQ ID NO:43].

The atp hexamerization domain facilitates self-assembly of the chimeric polypeptide into hexamers.

3.8 Human PD-L2 Ectodomain-L-Fc Dimerization Domain-L-Foldon Trimerization Domain

[SEQ ID NO: 51]
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPT-L-DKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

K-L-GSGYIPEAPRDGQAYVRKDGEWVLLSTF, wherein:
-L-, independently for each occurrence, represents a bond (e.g., peptide bond) or a peptide linker selected from the group consisting of: [GGSG]$_n$GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GSTSGSGKSSSEGSGSTKG [SEQ ID NO: 39], GSTSGSGKPGSGEGSTKG [SEQ ID NO: 40], EGKSSGSGSESKEF [SEQ ID NO: 41], GGSTSGSGKSSEGKG [SEQ ID NO: 42], and AAPA [SEQ ID NO:43].

The combination of the Fc dimerization domain and the foldon trimerization domain facilitates self-assembly of the chimeric polypeptide into hexamers.

3.9 Human PD-L2 Ectodomain-L-Fc Dimerization Domain-L-GCN4 Tetramerization Domain

[SEQ ID NO: 52]
MIFLLLMLSLELQLHQIAALFTVTVPKELYIIEHGSNVTLECNFDTGSHVN

LGAITASLQKVENDTSPHRERATLLEEQLPLGKASFHIPQVQVRDEGQYQC

IIIYGVAWDYKYLTLKVKASYRKINTHILKVPETDEVELTCQATGYPLAEV

SWPNVSVPANTSHSRTPEGLYQVTSVLRLKPPPGRNFSCVFWNTHVRELTL

ASIDLQSQMEPRTHPT-L-DKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFF

LYSKLTVDKSRWQQGNVFSCSVMHEALHNHYTQKSLSLSPGK-L-MKQIED

KLEEILSKLYHIENELARIKKLLGE, wherein:
-L-, independently for each occurrence, represents a bond (e.g., peptide bond) or a peptide linker selected from the group consisting of: [GGSG]$_n$GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GSTSGSGKSSSEGSGSTKG [SEQ ID NO: 39], GSTSGSGKPGSGEGSTKG [SEQ ID NO: 40], EGKSSGSGSESKEF [SEQ ID NO: 41], GGSTSGSGKSSEGKG [SEQ ID NO: 42], and AAPA [SEQ ID NO:43].

The combination of the Fc dimerization domain and the GCN4 tetramerization domain facilitates self-assembly of the chimeric polypeptide into octamers.

3.10 Human PD-L2 Ectodomain-L-Fc Dimerization Domain-L-COMP Pentamerization Domain

[SEQ ID NO: 53]
MIFLLLMLSLELQLHQIAALFTVTVPKELYIIEHGSNVTLECNFDTGSHVN

LGAITASLQKVENDTSPHRERATLLEEQLPLGKASFHIPQVQVRDEGQYQC

IIIYGVAWDYKYLTLKVKASYRKINTHILKVPETDEVELTCQATGYPLAEV

SWPNVSVPANTSHSRTPEGLYQVTSVLRLKPPPGRNFSCVFWNTHVRELTL

ASIDLQSQMEPRTHPT-L-DKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFF

LYSKLTVDKSRWQQGNVFSCSVMHEALHNHYTQKSLSLSPGK-L-LAPQML

RELQETNAALQDVRELLRQQVKQITFLKNTVMECDACG, wherein:
-L-, independently for each occurrence, represents a bond (e.g., peptide bond) or a peptide linker selected from the group consisting of: [GGSG]$_n$GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GSTSGSGKSSSEGSGSTKG [SEQ ID NO: 39], GSTSGSGKPGSGEGSTKG [SEQ ID NO: 40], EGKSSGSGSESKEF [SEQ ID NO: 41], GGSTSGSGKSSEGKG [SEQ ID NO: 42], and AAPA [SEQ ID NO:43].

The combination of the Fc dimerization domain and the COMP pentamerization domain facilitates self-assembly of the chimeric polypeptide into decamers.

3.11 Human PD-L2 Ectodomain-L-Fc Dimerization Domain-L-atp Hexamerization Domain

[SEQ ID NO: 54]
MIFLLLMLSLELQLHQIAALFTVTVPKELYIIEHGSNVTLECNFDTGSHVN

LGAITASLQKVENDTSPHRERATLLEEQLPLGKASFHIPQVQVRDEGQYQC

IIIYGVAWDYKYLTLKVKASYRKINTHILKVPETDEVELTCQATGYPLAEV

SWPNVSVPANTSHSRTPEGLYQVTSVLRLKPPPGRNFSCVFWNTHVRELTL

ASIDLQSQMEPRTHPT-L-DKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFF

LYSKLTVDKSRWQQGNVFSCSVMHEALHNHYTQKSLSLSPGK-L-PTHVNV

SVVMAEVDGTCY, wherein:
-L-, independently for each occurrence, represents a bond (e.g., peptide bond) or a peptide linker selected from the group consisting of: [GGSG]$_n$GG, [GGGGS]$_n$, [SSSSG]$_n$, [SSSSG]$_n$, [AAPA]$_n$, [GGGKGGGG]$_n$, [GGGNGGGG]$_n$, [GGGCGGGG]$_n$, wherein n is an integer from 1 to 10, suitably 1 to 5, more suitably 1 to 3, GG, GGGGG [SEQ ID NO:35], GGGGS [SEQ ID NO:36], SSSSG [SEQ ID NO:37], GKSSGSGSESKS [SEQ ID NO:38], GSTSGSGKSSSEGSGSTKG [SEQ ID NO: 39], GSTSGSGKPGSGEGSTKG [SEQ ID NO: 40], EGKSSGSGSESKEF [SEQ ID NO: 41], GGSTSGSGKSSEGKG [SEQ ID NO: 42], and AAPA [SEQ ID NO:43].

The combination of the Fc dimerization domain and the atp hexamerization domain facilitates self-assembly of the chimeric polypeptide into dodecamers.

4. Production of Chimeric Polypeptides

The PD-L2 polypeptide-oligomerization domain chimeras of the present invention may be prepared by chemical synthesis or recombinant means. Usually, the chimeric polypeptides are prepared by expression of a recombinant construct that encodes the chimeric polypeptide in suitable host cells, although any suitable methods can be used. Suitable host cells include, for example, insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster), avian cells (e.g., chicken, duck, and geese), bacteria (e.g., *Escherichia coli, Bacillus subtilis*, and *Streptococcus* spp.), yeast cells (e.g., *Saccharomyces cerevisiae, Candida albicans, Candida*

*maltosa, Hansenula polymorphs, Kluyveromyces fragilis, Kluyveromyces lactis, Pichia guillerimondii, Pichia pastoris, Schizosaccharomyces pombe* and *Yarrowia lipolytica*), Tetrahymena cells (e.g., Tetrahymena thermophile) or combinations thereof. Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in Vaccine 27:4975-4982 (2009) and WO2005/042728), EB66 cells, and the like.

Suitable insect cell expression systems, such as Baculovirus systems, are known to those of skill in the art and described in, e.g., Summers and Smith, Tex. Agricultural Experiment Station Bulletin No. 1555 (1987). Materials and methods for Baculovirus/insert cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, bacterial and mammalian cell expression systems are also known in the art and described in, e.g., Yeast Genetic Engineering (Barr et al., eds., 1989) Butterworths, London.

Recombinant constructs encoding the chimeric polypeptides of the present invention can be prepared in suitable vectors using conventional methods. A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable Baculovirus expression vector, such as pFastBac (Invitrogen), can be used to produce recombinant Baculovirus particles. The Baculovirus particles are amplified and used to infect insect cells to express recombinant protein. For expression in mammalian cells, a vector that will drive expression of the construct in the desired mammalian host cell (e.g., Chinese hamster ovary cells) is used.

The chimeric polypeptides can be purified using any suitable method. Suitable methods for purifying desired proteins including precipitation and various types of chromatography, such as hydrophobic interaction, ion exchange, affinity, chelating and size exclusion are well-known in the art. Suitable purification schemes can be created using two or more of these or other suitable methods. If desired, the chimeric polypeptides can include a purification moiety or "tag", that facilitates purification, as described in Section 3.5. Such tagged polypeptides can conveniently be purified, for example from conditioned media, by chelating chromatography or affinity chromatography.

5. Polypeptide Complexes Based on Chimeric Polypeptides

The chimeric polypeptides of the invention can self-assemble under suitable conditions to form polypeptide complexes. Accordingly, the present invention further encompasses a method of producing a polypeptide complex, wherein the method comprises: combining chimeric polypeptides of the present invention under conditions (e.g., in aqueous solution) suitable for the formation of a polypeptide complex, whereby a polypeptide complex is produced that comprises three or more chimeric polypeptides and is characterized by having at least one functional activity of PD-L2, as described for example herein. Generally the chimeric polypeptides self-assemble in a buffered aqueous solution (e.g., pH about 5 to about 9). If required, mild denaturing conditions can be used, such as, by including urea, small amounts of organic solvents or heat to mildly denature the chimeric polypeptides in order to facilitate refolding and self-assembly.

Any suitable preparation of chimeric polypeptides can be used in the method. For example, conditioned cell culture media that contains the desired chimeric polypeptide can be used in the method. However, it is preferable to use purified chimeric polypeptides in the method.

6. Compositions

The present invention further provides compositions, including pharmaceutical compositions, comprising a polypeptide complex or chimeric polypeptide, or a nucleic acid construct from which a chimeric polypeptide or complex is expressible, as broadly described above and elsewhere herein, and optionally a pharmaceutically acceptable carrier or adjuvant. Representative compositions may include a buffer, which is selected according to the desired use of the chimeric polypeptide or complex, and may also include other substances appropriate to the intended use. Where the intended use is to modulate an immune response, including a Th1 immune response, the composition is referred to as an "immune-modulating" or "immunomodulating" composition. Such compositions include preventative compositions (i.e., compositions administered for the purpose of preventing a Th1-related disease or disorder) and therapeutic compositions (i.e., compositions administered for the purpose of treating conditions a Th1-related disease or disorder). An immunomodulating composition of the present invention may therefore be administered to a recipient for prophylactic, ameliorative, palliative, or therapeutic purposes.

Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7.sup.th ed., Lippincott, Williams, & Wilkins; and Handbook of Pharmaceutical Excipients (2000) A. H. Kibbe et al., eds., 3.sup.rd ed. Amer. Pharmaceutical Assoc.

Pharmaceutical compositions of the present invention may be in a form suitable for administration by injection, in a formulation suitable for oral ingestion (such as, for example, capsules, tablets, caplets, elixirs), in the form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, subcutaneous, intramuscular or intravenous injection.

Supplementary active ingredients such as adjuvants or biological response modifiers can also be incorporated into pharmaceutical compositions of the present invention. Although adjuvant(s) may be included in pharmaceutical compositions of the present invention they need not necessarily comprise an adjuvant. In such cases, reactogenicity problems arising from the use of adjuvants may be avoided.

In general, adjuvant activity in the context of a pharmaceutical composition of the present invention includes, but is not limited to, an ability to enhance the immune response (quantitatively or qualitatively) induced by immunogenic components in the composition (e.g., a chimeric polypeptide or complex of the present invention). This may reduce the dose or level of the Immunomodulating components required to produce an immune response, including a Th1 immune response, and/or reduce the number or the frequency of immunizations required to produce the desired immune response.

Any suitable adjuvant may be included in a pharmaceutical composition of the present invention. For example, an aluminum-based adjuvant may be utilized. Suitable aluminum-based adjuvants include, but are not limited to, aluminum hydroxide, aluminum phosphate and combinations thereof. Other specific examples of aluminum-based adjuvants that may be utilized are described in European Patent No. 1216053 and U.S. Pat. No. 6,372,223. Other suitable adjuvants include Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; oil in water emulsions including those described in European Patent No. 0399843, U.S. Pat. No. 7,029,678 and PCT Publication No. WO 2007/006939; and/or additional cytokines, such as GM-CSF or interleukin-2, -7, or -12, granulocyte-macrophage colony-stimulating factor (GM-CSF), tumor necrosis factor (TNF) monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g., monophosphoryl lipid A and 3-Deacylated monophosphoryl lipid A), Flavivirus NS1 and muramyl dipeptide (MDP).

Pharmaceutical compositions of the present invention may be provided in a kit. The kit may comprise additional components to assist in performing the methods of the present invention such as, for example, administration device(s), buffer(s), and/or diluent(s). The kits may include containers for housing the various components and instructions for using the kit components in the methods of the present invention. Typically, the kits include instructions for using the immunomodulating compositions of the present invention, either by themselves or with a companion diagnostic, as for example described herein.

The polypeptide complexes of the present invention are useful for augmenting the immune response to an immune-modulating agent, including disease associated antigens (e.g., tumor antigens and antigens of pathogenic organisms) and antigen-binding molecules.

The present invention contemplates the use in the compositions of the invention of any antigen that corresponds to at least a portion of a target antigen of interest for stimulating an immune response to the target antigen. Such an antigen may be in soluble form (e.g., peptide, polypeptide or a nucleic acid molecule from which a peptide or polypeptide is expressible) or in the form of whole cells or attenuated pathogen preparations (e.g., attenuated virus or bacteria) or it may be presented by antigen-presenting cells as described in more detail below.

6.1 Antigens

Target antigens useful in the present invention can be any type of biological molecule including, for example, simple intermediary metabolites, sugars, lipids, and hormones as well as macromolecules such as complex carbohydrates, phospholipids, nucleic acids, polypeptides and peptides. Target antigens may be selected from endogenous antigens produced by a host or exogenous antigens that are foreign to the host. Suitable endogenous antigens include, but are not restricted to, cancer or tumour antigens. Non-limiting examples of cancer or tumour antigens include antigens from a cancer or tumour selected from ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumours, breast cancer, CNS tumours, carcinoid tumours, cervical cancer, childhood brain tumours, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-cell lymphoma, dermatofibrosarcoma-protuberans, desmoplastic-small-round-cell-tumour, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anaemia, fibrosarcoma, gall bladder cancer, gastric cancer, gastrointestinal cancers, gastrointestinal-carcinoid-tumour, genitourinary cancers, germ cell tumours, gestational-trophoblastic-disease, glioma, gynaecological cancers, haematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhans'-cell-histiocytosis, laryngeal cancer, leiomyosarcoma, leukaemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumours, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-Macroglobulinemia, Wilms' Tumour. In certain embodiments, the cancer or tumour relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP2IN2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{Pmel117}$ or a combination thereof. Other tumour-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papilloma virus proteins (squamous cell cancers of the cervix and oesophagus); NY-ESO-1 (testicular cancer); and HTLV-1 epitopes (T cell leukemia).

Foreign antigens are suitably selected from pathogenic organisms. Exemplary pathogenic organisms include, but are not limited to, viruses, bacteria, fungi parasites, algae and protozoa and amoebae. Illustrative examples of viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neuraminidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins EI and E2 and other rubella virus components; rotaviral antigens such as VP7sc and other rotaviral components. Illustrative examples of Cytomegaloviral antigens include, but are not limited to, antigens such as envelope glycoprotein B and other Cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremonium* spp., *Aspergillus* spp., Basidiobolus spp., *Bipolaris* spp., *Blastomyces dermatitidis, Candida* spp., *Cladophialophora carrionii, Coccidioides immitis, Conidiobolus* spp., *Cryptococcus* spp., *Curvularia* spp., *Epidermophyton* spp., *Exophiala jeanselmei, Exserohilum* spp., *Fonsecaea compacta, Fonsecaea pedrosoi, Fusarium oxysporum, Fusarium solani, Geotrichum candidum, Histoplasma capsulatum* var. *capsulatum, Histoplasma capsulatum* var. *duboisii, Hortaea werneckii, Lacazia loboi, Lasiodiplodia theobromae, Leptosphaeria senegalensis, Madurella grisea, Madurella mycetomatis, Malassezia furfur, Microsporum* spp., *Neotestudina rosatii, Onychocola canadensis, Paracoccidioides brasiliensis, Phialophora verrucosa, Piedraia hortae, Piedra iahortae, Pityriasis versicolor, Pseudallesheria boydii, Pyrenochaeta romeroi, Rhizopus arrhizus, Scopulariopsis brevicaulis, Scytalidium dimidiatum, Sporothrix schenckii, Trichophyton* spp., *Trichosporon* spp., *Zygomcete* fungi, *Absidia corymbifera, Rhizomucor pusillus* and *Rhizopus arrhizus*. Thus, illustrative fungal antigens that can be used in the compositions and methods of the present invention include, but are not limited to, *candida* fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *Coccidioides* fungal antigens such as spherule antigens and other *Coccidioides* fungal antigen components; and tinea fungal antigens such as trichophytin and other *Coccidioides* fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487), Other pathogenic bacteria include *Escherichia coli, Clostridium perfringens, Pseudomonas aeruginosa, Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components, pneumococcal bacterial antigens such as pneumolysin, pneumococcal capsular polysaccharides and other pneumococcal bacterial antigen components; *Haemophilus* influenza bacterial antigens such as capsular polysaccharides and other *Haemophilus* influenza bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: *Plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; *schistosoma* antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components.

The present invention also contemplates toxin components as antigens. Illustrative examples of toxins include, but are not restricted to, staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from *mycoplasma, mycobacterium*, and herpes viruses.

The antigen corresponding to at least a portion of the target antigen may be isolated from a natural source or may be prepared by recombinant techniques as known in the art. For example, peptide antigens can be eluted from the MHC and other presenting molecules of antigen-presenting cells obtained from a cell population or tissue for which a modified immune response is desired. The eluted peptides can be purified using standard protein purification techniques known in the art (Rawson et al., 2000, Cancer Res 60(16), 4493-4498. If desired, the purified peptides can be sequenced and synthetic versions of the peptides produced using standard protein synthesis techniques as for example described below. Alternatively, crude antigen preparations can be produced by isolating a sample of a cell population or tissue for which a modified immune response is desired, and either lysing the sample or subjecting the sample to conditions that will lead to the formation of apoptotic cells (e.g., irradiation with ultra violet or with γ rays, viral infection, cytokines or by depriving cells of nutrients in the cell culture medium, incubation with hydrogen peroxide, or with drugs such as dexamethasone, ceramide chemotherapeutics and anti-hormonal agents such as Lupron or Tamoxifen). The lysate or the apoptotic cells can then be used as a source of crude antigen for use in soluble form or for contact with antigen-presenting cells as described in more detail below.

In exemplary embodiments, the polypeptide complex or chimeric polypeptide of the present invention or a nucleic acid construct from which a chimeric polypeptide is expressible ("immune-modulating agent") is used for treatment of cancer. In some of these embodiments, the immune-modulating agent may be administered concurrently with at least one cancer therapy that inhibits the proliferation, survival or viability of tumor cells. The immune-modulating agent may be used therapeutically after the cancer therapy or may be used before the therapy is administered or together with the therapy. Accordingly, the present invention contemplates combination therapies, which employ an immune-modulating agent of the invention and concurrent administration of an cancer therapy, non-limiting examples of which include radiotherapy, surgery, chemotherapy, hormone ablation therapy, pro-apoptosis therapy and immunotherapy.

6.2 Radiotherapy

Radiotherapies include radiation and waves that induce DNA damage for example, γ-irradiation, X-rays, UV irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Non-limiting examples of radiotherapies include conformal external beam radiotherapy (50-100 Grey given as fractions over 4-8 weeks), either single shot or fractionated, high dose rate brachytherapy, permanent interstitial brachytherapy, systemic radio-isotopes (e.g., Strontium 89). In some embodiments the radiotherapy may be administered in combination with a radiosensitizing agent. Illustrative examples of radiosensitizing agents include but are not limited to efaproxiral, etanidazole, fluosol, misonidazole, nimorazole, temoporfin and tirapazamine.

6.3 Chemotherapy

Chemotherapeutic agents may be selected from any one or more of the following categories:

(i) antiproliferative/antineoplastic drugs and combinations thereof, as used in medical oncology, such as alkylating agents (e.g., cis-platin, carboplatin, cyclophosphamide, nitrogen mustard, melphalan, chlorambucil, busulphan and nitrosoureas); antimetabolites (e.g., antifolates such as fluoropyridines like 5-fluorouracil and tegafur, raltitrexed, methotrexate, cytosine arabinoside and hydroxyurea; anti-tumor antibiotics (e.g., anthracyclines like adriamycin, bleomycin, doxorubicin, daunomycin, epirubicin, idarubicin, mitomycin-C, dactinomycin and mithramycin); antimitotic agents (e.g., *Vinca* alkaloids like vincristine, vinblastine, vindesine and vinorelbine and taxoids like paclitaxel and docetaxel; and topoisomerase inhibitors (e.g., epipodophyllotoxins like etoposide and teniposide, amsacrine, topotecan and camptothecin);

(ii) cytostatic agents such as antiestrogens (e.g., tamoxifen, toremifene, raloxifene, droloxifene and idoxifene), estrogen receptor down regulators (e.g., fulvestrant), antiandrogens (for example bicalutamide, flutamide, nilutamide and cyproterone acetate), UH antagonists or LHRH agonists (e.g., goserelin, leuprorelin and buserelin), progestogens (for example megestrol acetate), aromatase inhibitors (e.g., as anastrozole, letrozole, vorozole and exemestane) and inhibitors of 5a-reductase such as finasteride;

(iii) agents which inhibit cancer cell invasion (e.g., metalloproteinase inhibitors like marimastat and inhibitors of urokinase plasminogen activator receptor function);

(iv) inhibitors of growth factor function, for example such inhibitors include growth factor antibodies, growth factor receptor antibodies (e.g., the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example other inhibitors of the epidermal growth factor family (e.g., other EGFR family tyrosine kinase inhibitors such as N-(3-chloro-4-fluorophenyl)-7-methoxy-6-(3-morpholinopropoxy)quinazolin-4-amine (Gefitinib, AZD1839), N-(3-ethynylphenyl)-6,7-bis(2-methoxyethoxy)quinazolin-4-amine (Erlotinib, OSI-774) and 6-acrylamido-N-(3-chloro-4-fluorophenyl)-7-(3-morpholinopropoxy)quinazoli-n-4-amine (CI 1033)), for example inhibitors of the platelet-derived growth factor family and for example inhibitors of the hepatocyte growth factor family;

(v) anti-angiogenic agents such as those which inhibit the effects of vascular endothelial growth factor, (e.g., the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense; and (viii) gene therapy approaches, including for example approaches to replace aberrant genes such as aberrant p53 or aberrant GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

6.4 Immunotherapy

Immunotherapy approaches, include for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies. These approaches generally rely on the use of immune effector cells and molecules to target and destroy cancer cells. The immune effector may be, for example, an antigen-binding molecule such as an antibody specific for a marker on the surface of a tumor cell. The antigen-binding molecule alone may serve as an effector of therapy or it may recruit other cells to actually facilitate cell killing. The antigen-binding molecule also may be conjugated to a drug or toxin (chemotherapeutic, radionuclide, ricin A chain, cholera toxin, pertussis toxin, etc.) and serve merely as a targeting agent. Alternatively, the immune effector may be a lymphocyte carrying a surface molecule that interacts, either directly or indirectly, with a malignant cell target. Various immune effector cells include cytotoxic T cells and NK cells.

In some of these embodiments, the cell surface antigen targeted by the antigen-binding molecule is suitably a tumor-associated antigen, illustrative examples of which include Her2/neu, EGFR, Epcam, VEGFR, FGFR, MUC-I, CA 125, CEA, MAGE, CD20, CD19, CD40, CD33, A3, antigen specific to A33 antibodies, BrE3 antigen, CD1, CD1a, CD5, CD8, CD14, CD15, CD16, CD21, CD22, CD23, CD30, CD33, CD37, CD38, CD40, CD45, CD46, CD52, CD54, CD74, CD79a, CD126, CD138, CD154, B7, Ia, Ii, HMI.24, HLA-DR (e.g., HLA-DR10), NCA95, NCA90, HCG and sub-units, CEA (CEACAM5), CEACAM-6, CSAp, EGP-I, EGP-2, Ba 733, KC4 antigen, KS-I antigen, KS1-4, Le-Y, MUC2, MUC3, MUC4, PIGF, ED-B fibronectin, NCA 66a-d, PAM-4 antigen, PSA, PSMA, RS5, SIOO, TAG-72, TIOI, TAG TRAIL-RI, TRAIL-R2, p53, tenascin, insulin growth factor-1 (IGF-I), Tn antigen etc.

6.5 Other Therapies

Examples of other cancer therapies include phototherapy, cryotherapy, toxin therapy or pro-apoptosis therapy. One of skill in the art would know that this list is not exhaustive of the types of treatment modalities available for cancer and other hyperplastic lesions.

It is well known that chemotherapy and radiation therapy target rapidly dividing cells and/or disrupt the cell cycle or cell division. These treatments are offered as part of the treating several forms of cancer, aiming either at slowing their progression or reversing the symptoms of disease by means of a curative treatment. However, these cancer treatments may lead to an immunocompromised state and ensuing pathogenic infections and thus the present invention also extends to combination therapies, which employ both a polypeptide complex, a cancer therapy and an anti-infective agent that is effective against an infection that develops or that has an increased risk of developing from an immunocompromised condition resulting from the cancer therapy. The anti-infective drug is suitably selected from antimicrobials, which include without limitation compounds that kill or inhibit the growth of microorganisms such as viruses, bacteria, yeast, fungi, protozoa, etc. and thus include antibiotics, amebicides, antifungals, antiprotozoals, antimalarials, antituberculotics and antivirals. Anti-infective drugs also include within their scope anthelmintics and nematocides. Illustrative antibiotics include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperozolid), glycopeptides, aminoglycosides (e.g., amikacin, arbekacin, butirosin, dibekacin, fortimicins, gentamicin, kanamycin, meomycin, netilmicin, ribostamycin, sisomicin, spectinomycin, streptomycin, tobramycin), p-lactams (e.g., imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol.

Illustrative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine.

Non-limiting examples of amebicides or antiprotozoals include atovaquone, chloroquine hydrochloride, chloroquine phosphate, metronidazole, metronidazole hydrochloride, and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine, and streptomycin sulfate.

In other embodiments in which the Th1-related disease is a pathogenic infection, the polypeptide complex of the present invention is concurrently administered with an anti-infective, as described for example supra.

As noted above, the present invention encompasses co-administration of an immune-modulating agent of the present invention in concert with an additional or ancillary agent. It will be understood that, in embodiments comprising administration of the immune-modulating agent with one or more other agents, the dosages of the actives in the combination may on their own comprise an effective amount and the additional agent(s) may further augment the therapeutic or prophylactic benefit to the patient. Alternatively, the immune-modulating agent and the additional agent(s) may together comprise an effective amount for preventing or treating the Th1-related disease or disorder. It will also be understood that effective amounts may be defined in the context of particular treatment regimens, including, e.g., timing and number of administrations, modes of administrations, formulations, etc. In some embodiments, the immune-modulating agent and optionally a cancer therapy are administered on a routine schedule. Alternatively, the cancer therapy may be administered as symptoms arise. A "routine schedule" as used herein, refers to a predetermined designated period of time. The routine schedule may encompass periods of time which are identical or which differ in length, as long as the schedule is predetermined. For instance, the routine schedule may involve administration of the polypeptide complex on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve concurrent administration of the polypeptide complex and the cancer therapy on a daily basis for the first week, followed by a monthly basis for several months, and then every three months after that. Any particular combination would be covered by the routine schedule as long as it is determined ahead of time that the appropriate schedule involves administration on a certain day.

6.6 Dosages and Routes of Administration

The composition is administered in an "effective amount" that is, an amount effective to achieve an intended purpose in a subject. The dose of active compound(s) administered to a patient should be sufficient to achieve a beneficial response in the subject over time such as a reduction in at least one symptom associated with a Th1-associated disease or disorder. The quantity or dose frequency of the pharmaceutically active compounds(s) to be administered may depend on the subject to be treated inclusive of the age, sex, weight and general health condition thereof. In this regard, precise amounts of the active compound(s) for administration will depend on the judgment of the practitioner. One skilled in the art would be able, by routine experimentation, to determine an effective, non-toxic amount of an immune-modulating agent described herein to include in a pharmaceutical composition of the present invention for the desired therapeutic outcome.

In general, a pharmaceutical composition of the present invention can be administered in a manner compatible with the route of administration and physical characteristics of the recipient (including health status) and in such a way that it elicits the desired effect(s) (i.e. therapeutically effective, immunogenic and/or protective). For example, the appropriate dosage of a pharmaceutical composition of the present invention may depend on a variety of factors including, but not limited to, a subject's physical characteristics (e.g., age, weight, sex), whether the compound is being used as single agent or adjuvant therapy, the type of MHC restriction of the patient, the progression (i.e., pathological state) of a virus infection, and other factors that may be recognized by one skilled in the art. Various general considerations that may be considered when determining an appropriate dosage of a pharmaceutical composition of the present invention are described, for example, in Gennaro (2000) "Remington: The Science and Practice of Pharmacy", 20th edition, Lippincott, Williams, & Wilkins; and Gilman et al., (Eds), (1990), "Goodman And Gilman's: The Pharmacological Bases of Therapeutics", Pergamon Press.

In some embodiments, an "effective amount" of a subject immune-modulating agent, is an amount sufficient to achieve a desired prophylactic or therapeutic effect, e.g., to reduce a symptom associated with a Th1-related disease or disorder. In these embodiments, an effective amount reduces a symptom associated with Th1-related disease or disorder in an individual by at least about 10%, at least about 20%, at least about 30%, at least about 40%, at least about 50%, at least about 60%, at least about 70%, at least about 80%, or at least about 90%, or more, when compared to the symptom in an individual not treated with the immune-modulating agent. Symptoms of various Th1-related disease or disorders, as well as methods for measuring such symptoms, are known in the art. For example, methods for measuring tumor burden, grade of tumor, the number of pathogenic organisms in an individual, etc. are standard in the art.

In some embodiments, an "effective amount" of a subject immune-modulating agent is an amount that is effective in a selected route of administration to elicit an immune response, including a Th1 immune response. Methods for measuring an immune response, including a Th1 immune response, are known to persons of ordinary skill in the art. Exemplary methods include solid-phase heterogeneous assays (e.g., enzyme-linked immunosorbent assay), solution phase assays (e.g., electrochemiluminescence assay), amplified luminescent proximity homogeneous assays, flow cytometry, intracellular cytokine staining, functional T-cell assays, functional B-cell assays, functional monocyte-macrophage assays, dendritic and reticular endothelial cell assays, measurement of NK cell responses, IFN-γ production by immune cells, quantification of virus RNA/DNA in tissues or biological fluids (e.g., quantification of viral RNA or DNA in serum or other fluid or tissue/organ), oxidative burst assays, cytotoxic-specific cell lysis assays, pentamer binding assays, and phagocytosis and apoptosis evaluation.

A pharmaceutical composition of the present invention can be administered to a recipient by standard routes, including, but not limited to, parenteral (e.g., intravenous).

A pharmaceutical composition of the present invention may be administered to a recipient in isolation or in conjunction with additional therapeutic agent(s). In embodiments where a pharmaceutical composition is concurrently administered with therapeutic agent(s), the administration may be simultaneous or sequential (i.e., pharmaceutical composition administration followed by administration of the agent(s) or vice versa).

Typically, in treatment applications, the treatment may be for the duration of the disease state or condition. Further, it will be apparent to one of ordinary skill in the art that the optimal quantity and spacing of individual dosages will be determined by the nature and extent of the disease state or condition being treated, the form, route and site of administration, and the nature of the particular individual being treated. Optimum conditions can be determined using conventional techniques.

In many instances (e.g., preventative applications), it may be desirable to have several or multiple administrations of a pharmaceutical composition of the present invention. For example, a pharmaceutical composition may be administered 1, 2, 3, 4, 5, 6, 7, 8, 9, 10, or more times. The administrations may be from about one to about twelve week intervals, and in certain embodiments from about one to about four week intervals. Periodic re-administration may be desirable in the case of recurrent exposure to a particular pathogen or other disease-associated component targeted by a pharmaceutical composition of the present invention.

It will also be apparent to one of ordinary skill in the art that the optimal course of administration can be ascertained using conventional course of treatment determination tests.

Where two or more entities are administered to a subject "in conjunction" or "concurrently" they may be administered in a single composition at the same time, or in separate compositions at the same time, or in separate compositions separated in time.

Certain embodiments of the present invention involve the administration of pharmaceutical compositions in multiple separate doses. Accordingly, the methods for the prevention and treatment of a Th1-related disease or disorder herein encompass the administration of multiple separated doses to a subject, for example, over a defined period of time. Accordingly, the methods for the prevention and treatment of infection disclosed herein include administering a priming dose of a pharmaceutical composition of the present invention. The priming dose may be followed by a booster dose. The booster may be for the purpose of re-vaccination. In various embodiments, the pharmaceutical composition or vaccine is administered at least once, twice, three times or more.

7. Methods of Treatment

The immune-modulating agents of the present invention are useful for treating a disease that is associated with a reduced or impaired Th1 immune response. For example, the Th1-related disease may be an infection with a virus, bacteria, fungi, or parasite. Viruses include, but are not limited to, Retroviridae human immunodeficiency viruses, such as HIV-1 (also referred to as HTLV-III, LAV or HTLV-III/LAV, or HIV-III); and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis, including Norwalk and related viruses); Togaviridae (e.g., equine encephalitis viruses, rubella viruses); Fiaviridae (e.g., dengue viruses, encephalitis viruses, yellow fever viruses); Coronoviridae (e.g., coronaviruses); Rhabdoviradae (e.g., vesicular stornatitis viruses, rabies viruses); Filoviridae (e.g., ebola viruses); Paramyxoviridae (e.g., parainfluenza viruses, mumps virus, measles virus, respiratory syncytial virus, metaneumovirus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Heriesviridae (herpes simplex virus (HSV) 1 and 2, varicella zoster virus, cytomegalovirus (CMV), herpes virus); Poxyiridae (variola viruses, VACV, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); and astroviruses.

In some embodiments, the pathogenic infection is a bacterial pathogen. Bacteria from which are known to be pathogenic in a subject include, but are not limited to, pathogenic *Pasteurella* species (e.g., *Pasteurella multocida*), *Staphylococci* species (e.g., *Staphylococcus aureus*), *Streptococcus* species (e.g., *Streptococcus pyogenes* (Group A *Streptococcus*), *Streptococcus agalactiae* (Group B *Streptococcus*), *Streptococcus* (*viridans* group), *Streptococcus faecalis*, *Streptococcus bovis*, *Streptococcus* (anaerobic sps.), *Streptococcus pneumoniae*), *Neisseria* species (e.g., *Neisseria gonorrhoeae*, *Neisseria meningitidis*), *Escherichia* species (e.g., enterotoxigenic *E. coli* (ETEC), enteropathogenic *E. coli* (EPEC), enterohemorrhagic *E. coli* (EHEC), and enteroinvasive *E. coli* (EIEC)), *Bordetella* species, *Campylobacter* species, *Legionella* species (e.g., *Legionella pneumophila*), *Pseudomonas* species, *Shigella* species, *Vibrio* species, *Yersinia* species, *Salmonella* species, *Haemophilus* species (e.g., *Haemophilus influenzae*), *Brucella* species, *Francisella* species, *Bacterioides* species, *Clostridia* species (e.g., *Clostridium difficile*, *Clostridium perfringens*, *Clostridium tetani*), Mycobacteria species (e.g., *M. tuberculosis*, *M. avium*, *M. intracellulare*, *M. kansaii*, *M. gordonae*), *Helicobacter pyloris*, *Borelia burgdorferi*, *Listeria monocytogenes*, *Chlamydia trachomatis*, *Enterococcus* species, *Bacillus anthracis*, *Corynebacterium diphtheriae*, *Erysipelothrix rhusiopathiae*, *Enterobacter aerogenes*, *Klebsiella pneumoniae*, *Fusobacterium nucleatum*, *Streptobacillus moniliformis*, *Treponema pallidium*, *Treponema pertenue*, *Leptospira*, *Rickettsia*, and *Actinomyces israeli*.

In other embodiments of the invention, the pathogenic infection is a eukaryotic pathogen, such as pathogenic fungi and parasites. Fungi that are known to be pathogenic at least to some extent include, but are not limited to, *Cryptococcus neoformans*, *Histoplasma capsulatum*, *Coccidioides immitis*, *Blastomyces dermatitidis*, *Candida albicans*, *Candida glabrata*, *Aspergillus fumigata*, *Aspergillus flavus*, and *Sporothrix schenckii*.

Other eukaryotic pathogens from which the heterologous antigen can be derived include, but are not limited to, pathogenic protozoa, helminths, *Plasmodium*, such as *Plasmodium falciparum*, *Plasmodium malariae*, *Plasmodium ovale*, and *Plasmodium vivax*; *Toxoplasma gondii*; *Trypanosoma brucei*, *Trypanosoma cruzi*; *Schistosoma haematobium*, *Schistosoma mansoni*, *Schistosoma japonicum*; *Leishmania donovani*; *Giardia intestinalis*; *Cryptosporidium parvum*; and the like.

Other diseases that may be associated with a reduced or impaired Th1 immune response also include any malignant or pre-malignant condition, proliferative or hyper-proliferative condition or any disease arising or deriving from or associated with a functional or other disturbance or abnormality in the proliferative capacity or behaviour of any cells or tissues of the body. Non-limiting cancers that could be treated with the polypeptide complexes and compositions of the present invention include breast cancer, colon cancer, lung cancer and prostate cancer, cancers of the blood and lymphatic systems (including Hodgkin's disease, leukemias, lymphomas, multiple myeloma, and Waldenstrom's disease), skin cancers (including malignant melanoma), cancers of the digestive tract (including head and neck cancers, esophageal cancer, stomach cancer, cancer of the pancreas, liver cancer, colon and rectal cancer, anal cancer), cancers of the genital and urinary systems (including kidney cancer, bladder cancer, testis cancer, prostate cancer), cancers in women (including breast cancer, ovarian cancer, gynecological cancers and choriocarcinoma) as well as in brain, bone carcinoid, nasopharyngeal, retroperitoneal, thyroid and soft tissue tumours.

8. Th1 Immune Status Biomarkers and their Use

The present invention is also based in part on the determination that PD-L2 expression on IEC-interacting cells, including APCs such as dendritic cells, inversely correlates with the severity of Th1-related diseases and that PD-L2 is required to establish Th1 immunity. Accordingly, the present inventors have determined that PD-L2 is a reliable indicator of an upregulated and/or enhanced Th1 immune response in a subject. They have also discovered other biomarkers that are modulated during a Th1 immune response. Inclusion of these additional biomarkers increases the diagnostic power and reliability of the diagnostic and prognostic assays taught herein. Based on these determinations, it is proposed that PD-L2, optionally in combination with other Th1 immune status biomarkers, is indicative of the Th1 immune status of a subject, and has utility for tracking Th1 immune status development in subjects suffering from Th1-related diseases.

As such, the present invention also provides methods, apparatus, compositions and kits for identifying the Th1 immune status of a subject, or for providing a prognosis for subjects with a Th1-related disease, as a companion diagnostic for the polypeptide complexes and chimeric polypeptides of the present invention.

8.1 Th1 Immune Status Biomarkers

The present inventors have determined that certain surface markers are present on IEC-interacting cells, including APCs such as dendritic cells, that are specifically expressed in humans and mice during a Th1 immune response. The results presented herein provide clear evidence that a unique biologically-relevant biomarker profile predicts the Th1 immune status of a subject with a remarkable degree of accuracy. Overall, these findings provide compelling evidence that the IEC-interacting cell surface biomarkers disclosed herein, and particularly PD-L2, can function as biomarkers for determining Th1 immune status and may potentially serve as a useful diagnostic for triaging treatment decisions for subjects suffering with a disease associated with an undesirable Th1 immune status. In this regard, it is proposed that the methods, apparatus, compositions and kits disclosed herein that are based on these biomarkers may serve in the point-of-care diagnostics that allow for rapid and inexpensive determination of a Th1 immune status, which may result in significant cost savings to the medical system as subjects with an undesirable Th1 immune response can be exposed to therapeutic agents that are suitable for enhancing or depleting the Th1 immune response in the subject as necessary.

Using the methods described herein, a number of biomarkers have been identified that are particularly useful for determining the Th1 immune status of a subject. These biomarkers are referred to herein as "Th1 immune status biomarkers". As used herein, the term "Th1 immune status biomarker" refers to a biomarker of the subject, generally a biomarker of the subject's immune system, which is altered, or whose level of expression is altered, as part of a Th1 immune response. The Th1 immune status biomarkers are suitably expression products of genes (also referred to interchangeably herein as "Th1 immune response biomarker genes"), including polynucleotide and polypeptide expression products. As used herein, polynucleotide expression products of Th1 immune status biomarker genes are referred to herein as "Th1 immune status biomarker polynucleotides." Polypeptide expression products of the Th immune response biomarker genes are referred to herein as "Th1 immune status biomarker polypeptides".

The at least one Th1 immune status biomarker of the present invention suitably comprises PD-L2. The native human PD-L2 amino acid sequence is set forth in SEQ ID NO: 1, and is encoded by the nucleic acid sequence:

[SEQ ID NO: 55]
ACGCGGGGTTTTCTTCTCTTGAATATATCTTAACGCCAAATTTTGAGTGC

TTTTTTTGTTACCCATCCTCATATGTCCCAGCTAGAAAGAATCCTGGGTTG

GAGCTACTGCATGTTGATTGTTTTGTTTTTCCTTTTGGCTGTTCATTTTGG

TGGCTACTATAAGGAAATCTAACACAAACAGCAACTGTTTTTTGTTGTTTA

CTTTTGCATCTTTACTTGTGGAGCTGTGGCAAGTCCTCATATCAAATACAG

AACATGATCTTCCTCCTGCTAATGTTGAGCCTGGAATTGCAGCTTCACCAG

ATAGCAGCTTTATTCACAGTGACAGTCCCTAAGGAACTGTACATAATAGAG

CATGGCAGCAATGTGACCCTGGAATGCAACTTTGACACTGGAAGTCATGTG

AACCTTGGAGCAATAACAGCCAGTTTGCAAAAGGTGGAAAATGATACATCC

CCACACCGTGAAAGAGCCACTTTGCTGGAGGAGCAGCTGCCCCTAGGGAAG

GCCTCGTTCCACATACCTCAAGTCCAAGTGAGGGACGAAGGACAGTACCAA

TGCATAATCATCTATGGGGTCGCCTGGGACTACAAGTACCTGACTCTGAAA

GTCAAAGCTTCCTACAGGAAAATAAACACTCACATCCTAAAGGTTCCAGAA

ACAGATGAGGTAGAGCTCACCTGCCAGGCTACAGGTTATCCTCTGGCAGAA

GTATCCTGGCCAAACGTCAGCGTTCCTGCCAACACCAGCCACTCCAGGACC

CCTGAAGGCCTCTACCAGGTCACCAGTGTTCTGCGCCTAAAGCCACCCCCT

GGCAGAAACTTCAGCTGTGTGTTCTGGAATACTCACGTGAGGGAACTTACT

TTGGCCAGCATTGACCTTCAAAGTCAGATGGAACCCAGGACCCATCCAACT

TGGCTGCTTCACATTTTCATCCCCTCCTGCATCATTGCTTTCATTTTCATA

GCCACAGTGATAGCCCTAAGAAAACAACTCTGTCAAAAGCTGTATTCTTCA

AAAGACACAACAAAAAGACCTGTCACCACAACAAAGAGGGAAGTGAACAGT

GCTATCTGAACCTGTGGTCTTGGGAGCCAGGGTGACCTGATATGACATCTA

AAGAAGCTTCTGGACTCTGAACAAGAATTCGGTGGCCTGCAGAGCTTGCCA

TTTGCACTTTTCAAATGCCTTTGGATGACCCAGCACTTTAATCTGAAACCT

GCAACAAGACTAGCCAACACCTGGCCATGAAACTTGCCCCTTCACTGATCT

GGACTCACCTCTGGAGCCTATGGCTTTAAGCAAGCACTACTGCACTTTACA

GAATTACCCCACTGGATCCTGGACCCACAGAATTCCTTCAGGATCCTTCTT

GCTGCCAGACTGAAAGCAAAAGGAATTATTTCCCCTCAAGTTTTCTAAGTG

ATTTCCAAAAGCAGAGGTGTGTGGAAATTTCCAGTAACAGAAACAGATGGG

TTGCAATAGAGTTATTTTTTATCTATAGCTTCCTCTGGG

Another Th1 immune status biomarker that can optionally be used in the methods of the invention is PD-L1. The native human PD-L1 amino acid sequence is:

[SEQ ID NO: 56]
MRIFAVFIFMTYWHLLNAFTVTVPKDLYVVEYGSNMTIECKFPVEKQLDLA

ALIVYWEMEDKNIIQFVHGEEDLKVQHSSYRQRARLLKDQLSLGNAALQIT

DVKLQDAGVYRCMISYGGADYKRITVKVNAPYNKINQRILVVDPVTSEHEL

TCQAEGYPKAEVIVVTSSDHQVLSGKTTTTNSKREEKLFNVTSTLRINTTT

NEIFYCTFRRLDPEENHTAELVIPELPLAHPPNERTHLVILGAILLCLGVA

LTFIFRLRKGRMMDVKKCGIQDTNSKKQSDTHLEET, and is encoded by the nucleic acid sequence:

[SEQ ID NO: 57]
ATGAGGATATTTGCTGTCTTTATATTCATGACCTACTGGCATTTGCTGAAC

GCATTTACTGTCACGGTTCCCAAGGACCTATATGTGGTAGAGTATGGTAGC

AATATGACAATTGAATGCAAATTCCCAGTAGAAAAACAATTAGACCTGGCT

GCACTAATTGTCTATTGGGAAATGGAGGATAAGAACATTATTCAATTTGTG

CATGGAGAGGAAGACCTGAAGGTTCAGCATAGTAGCTACAGACAGAGGGCC

CGGCTGTTAAGGACCAGCTCTCCCTGGGAAATGCTGCACTTCAGATCACA

GATGTGAAATTGCAGGATGCAGGGGTGTACCGCTGCATGATCAGCTATGGT

GGTGCCGACTACAAGCGAATTACTGTGAAAGTCAATGCCCCATACAACAAA

ATCAACCAAAGAATTTTGGTTGTGGATCCAGTCACCTCTGAACATGAACTG

ACATGTCAGGCTGAGGGCTACCCCAAGGCCGAAGTCATCGTGGACAAGCAGT

GACCATCAAGTCCTGAGTGGTAAGACCACCACCACCAATTCCAAGAGAGAG

GAGAAGCTTTTCAATGTGACCAGCACACTGAGAATCAACACAACAACTAAT

GAGATTTTCTACTGCACTTTTAGGAGATTAGATCCTGAGGAAAACCATACA

GCTGAATTGGTCATCCCAGAACTACCTCTGGCACATCCTCCAAATGAAAGG

ACTCACTTGGTAATTCTGGGAGCCATCTTATTATGCCTTGGTGTAGCACTG

-continued

```
ACATTCATCTTCCGTTTAAGAAAAGGGAGAATGATGGATGTGAAAAAATGT

GGCATCCAAGATACAAACTCAAAGAAGCAAAGTGATACACATTTGGAGGAG

ACGTAA.
```

Of the above Th1 immune status biomarkers, the PD-L2 polypeptide has been found to have strong diagnostic performance on its own for detecting Th1 immune status (as measured, for example, using FACS analysis by measuring percentage of PD-L2$^+$ IEC-interacting cells such as APCs). Thus, in specific embodiments the PD-L2 biomarker may be used either by itself or in combination with other Th1 immune status biomarkers for the determination of the indicator. Suitably, in these embodiments, a biomarker value is measured or derived for the PD-L2 biomarker and optionally anther Th1 immune status biomarker(s) (e.g., PD-L1) to determine the indicator.

The present inventors have also determined that other Th1 immune status biomarkers have strong diagnostic performance when used in combination with the PD-L2 biomarker. In advantageous embodiments, pairs of Th1 immune status biomarkers have been identified that can be used to determine the indicator. Accordingly, in representative examples of this type, and as described in detail below, an indicator is determined that correlates to a ratio of Th1 immune status biomarkers, which can be used in determining the Th1 immune status of a subject.

Thus, specific protein products are disclosed herein as Th1 immune response biomarkers that provide a means for determining the Th1 immune status of a subject. Evaluation of these Th1 immune status biomarkers through analysis of their levels in a subject, or in a sample obtained from a subject, provides a measured or derived biomarker value for determining an indicator that can be used for assessing the Th1 immune status in a subject.

8.2 Sample Preparation

Generally, a sample is processed prior to Th1 immune status biomarker detection or quantification. For example, proteins and/or nucleic acids may be extracted, isolated, and/or purified from a sample prior to analysis. Various protein, DNA, and/or mRNA extraction and purification techniques are well known to those skilled in the art. Processing may include centrifugation, ultracentrifugation, ethanol precipitation, filtration, fractionation, resuspension, dilution, concentration, etc. In some embodiments, the methods taught above and elsewhere herein provide analysis (e.g., quantification of protein biomarkers) from raw sample (e.g., biological fluid such as blood, serum, etc.) without or with limited processing.

Furthermore, a sample can be processed prior to Th1 immune status biomarker detection or quantification in order to purify or enrich the sample for a particular fraction or cell type of interest. For example, the sample can be enriched for IEC-interacting cells such as APCs or tumor cells, or a particular subset of APCs (e.g., dendritic cells, macrophages, monocytes, B cells, or a combination thereof). In preferred embodiments, the sample is enriched for IEC-interacting cells such as APCs (e.g., dendritic cells, including CD11c$^+$ dendritic cells) and tumor cells prior to Th1 immune status biomarker detection or quantification. Methods for enriching biological samples for a particular cell type are well known in the art. For example, dendritic cells may be isolated by differential gradient separation using, for example, Ficoll-Hypaque or sucrose gradient solutions for cell separations, followed by ammonium chloride or hypotonic lysis of remaining contaminating erythrocytes ("Cell Biology: A Laboratory Handbook", Volumes I-III Cellis, J. E., ed. (1994); "Current Protocols in Immunology" Volumes I-III Coligan J. E., ed. (1994); Stites et al. (eds)).

Sample preparation methods may comprise steps of homogenizing a sample in a suitable buffer, removal of contaminants and/or assay inhibitors, adding a Th1 immune status biomarker capture reagent (e.g., a magnetic bead which is linked to a moiety that can specifically bind to a target Th1 immune status biomarker), incubated under conditions that promote the association of the target biomarker with the capture reagent to produce a target biomarker: capture reagent complex, and incubating the target biomarker: capture complex under target biomarker-release conditions. In some embodiments, multiple Th1 immune status biomarkers are isolated in each round of isolation by adding multiple Th1 immune status biomarkers capture reagents (e.g., specific to the desired biomarkers) to the solution. For example, in an illustrative embodiment in which the biomarker is a nucleic acid, multiple Th1 immune status biomarker capture reagents, each comprising an oligonucleotide specific for a different target Th1 immune status biomarker can be added to the sample for isolation of multiple Th1 immune status biomarkers. It is contemplated that the methods encompass multiple experimental designs that vary both in the number of capture steps and in the number of target Th1 immune status biomarkers captured in each capture step. In some embodiments, capture reagents are molecules, moieties, substances, or compositions that preferentially (e.g., specifically and selectively) interact with a particular biomarker sought to be isolated, purified, detected, and/or quantified. Any capture reagent having desired binding affinity and/or specificity to the particular Th1 immune status biomarker can be used in the present technology. For example, the capture reagent can be a macromolecule such as a peptide, a protein (e.g., an antibody or receptor), an oligonucleotide, a nucleic acid, (e.g., nucleic acids capable of hybridizing with the Th1 immune status biomarkers), vitamins, oligosaccharides, carbohydrates, lipids, or small molecules, or a complex thereof. As illustrative and non-limiting examples, an avidin target capture reagent may be used to isolate and purify targets comprising a biotin moiety, an antibody may be used to isolate and purify targets comprising the appropriate antigen or epitope, and an oligonucleotide may be used to isolate and purify a complementary oligonucleotide.

Any nucleic acids, including single-stranded and double-stranded nucleic acids, that are capable of binding, or specifically binding, to a target Th1 immune status biomarker can be used as the capture reagent. Examples of such nucleic acids include DNA, RNA, aptamers, peptide nucleic acids, and other modifications to the sugar, phosphate, or nucleoside base. Thus, there are many strategies for capturing a target and accordingly many types of capture reagents are known to those in the art.

In addition, Th1 immune status biomarker capture reagents may comprise a functionality to localize, concentrate, aggregate, etc. the capture reagent and thus provide a way to isolate and purify the target Th1 immune status biomarker when captured (e.g., bound, hybridized, etc.) to the capture reagent (e.g., when a target:capture reagent complex is formed). For example, in some embodiments the portion of the capture reagent that interacts with the Th1 immune status biomarker (e.g., an polypeptide) is linked to a solid support (e.g., a bead, surface, resin, column, and the like) that allows manipulation by the user on a macroscopic scale. Often, the solid support allows the use of a mechanical means to isolate and purify the target:capture reagent complex from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target Th1 immune status biomarker) from the heterogeneous solution.

8.3 Evaluation of Th1 Immune Status Biomarker Polypeptide

In order to obtain the biomarker value, the Th1 immune status biomarkers may be quantified or detected using any suitable technique that is known in the art. In specific embodiments, the Th1 immune status biomarkers are quantified using reagents that determine the level, abundance or amount of individual Th1 immune status biomarkers. Non-limiting reagents of this type include reagents for use in protein-based and nucleic acid-based assays.

Th1 immune status biomarker expression may be evaluated at the level of protein expression, either by demonstration of the presence of the protein, or by one or more known functional properties of the biomarker. For example, anti-PD-L2 antibodies for use in PD-L2-specific protein detection are described in U.S. Pat. No. 7,709,214; U.S. patent application Ser. No. 2009/296,392; and European Pat. No. 1537878, which are incorporated by reference herein in their entirety. The antibodies bind both native and denatured PD-L2 protein and may be detected by several well-known assays in the art, including enzyme linked immunosorbent assays (ELISA), radioimmunoassays (RIA), light emission immunoassays, Western blot analysis, immunofluorescence assays, immunohistochemistry and fluorescence activated cell sorting (FACS) analysis.

ELISA and RIA follow similar principles for detection of specific antigens. By way of an illustrative example, PD-L2 can be measured using RIA by way of a PD-L2-specific antibody that is radioactively labeled, typically with $^{125}$I. In ELISA assays a PD-L2-specific antibody is chemically linked to an enzyme. PD-L2-specific capturing antibody is immobilized onto a solid support. Unlabeled specimens, e.g., protein extracts from biological samples are then incubated with the immobilized antibody under conditions where non-specific binding is blocked, and unbound antibody and/or protein removed by washing. Bound PD-L2 is detected by a second PD-L2 specific labeled antibody. Antibody binding is measured directly in RIA by measuring radioactivity, while in ELISA binding is detected by a reaction converting a colourless substrate into a coloured reaction product, as a function of linked-enzyme activity. Changes can thus readily be detected by spectrophotometry (Janeway C. A. et al. (1997). "Immunobiology" 3.sup.rd Edition, Current Biology Ltd., Garland Publishing Inc.; "Cell Biology: A Laboratory Handbook", Volumes I-III Cellis, J. E., ed. (1994); "Current Protocols in Immunology" Volumes I-III Coligan J. E., ed. (1994); Stites et al. (eds)). Both assays therefore provide a means of quantification of PD-L2 protein content in a biological sample.

Protein biomarker expression may also be detected via light emission immunoassays. Much like ELISA and RIA, in light emission immunoassays the biological sample/protein extract to be tested is immobilized on a solid support, and probed with a specific label, labeled anti-PD-L2 antibody. The label, in turn, is luminescent, and emits light upon binding, as an indication of specific recognition. Luminescent labels include substances that emit light upon activation by electromagnetic radiation, electro chemical excitation, or chemical activation and may include fluorescent and phosphorescent substances, scintillators, and chemiluminescent substances. The label can be a part of a catalytic reaction system such as enzymes, enzyme fragments, enzyme substrates, enzyme inhibitors, coenzymes, or catalysts; part of a chromogen system such as fluorophores, dyes, chemiluminescers, luminescers, or sensitizers; a dispersible particle that can be non-magnetic or magnetic, a solid support, a liposome, a ligand, a receptor, a hapten radioactive isotope, and so forth (U.S. Pat. Nos. 6,410,696, 4,652,533 and European Patent Application No. 0,345,776), and provide an additional, highly sensitive method for detection of PD-L2 protein expression.

Western blot analysis is another means of assessing Th1 immune status biomarker polypeptide content in a biological sample. Protein extracts from biological samples of IEC-interacting cells such as APCs (e.g., dendritic cells) or tumor cells, are solubilized in a denaturing ionizing environment, and aliquots are applied to polyacrylamide gel matrixes. Proteins separate based on molecular size properties as they migrate toward the anode. Antigens are then transferred to nitrocellulose, PVDF or nylon membranes, followed by membrane blocking to minimize non-specific binding. Membranes are probed with antibodies directly coupled to a detectable moiety, or are subsequently probed with a secondary antibody containing the detectable moiety. Typically the enzymes horseradish peroxidase or alkaline phosphatase are coupled to the antibodies, and chromogenic or luminescent substrates are used to visualize activity (Harlow E. et al., (1998) Immunoblotting. In Antibodies: A Laboratory Manual, pp. 471-510 CSH Laboratory, cold Spring Harbor, N.Y. and Bronstein I. Et al. (1992) Biotechniques 12: 748-753).

Unlike RIA, ELISA, light emission immunoassays and immunoblotting, which quantify protein biomarker content in whole samples, immunofluorescence/immunocytochemistry may be used to detect proteins in a cell-specific manner, though quantification is compromised.

As described above, IEC-interacting cells such as APCs (e.g., dendritic cells) or tumor cells may be isolated or enriched by methods known in the art. Isolation or enrichment of IEC-interacting cells refers to a process wherein the percentage of IEC-interacting cells is increased (relative to the percentage in the sample before the enrichment procedure). Purification is one example of enrichment. In certain embodiments, the increase in the number of IEC-interacting cells such as APCs (e.g., dendritic cells) or tumor cells, as a percentage of cells in the enriched sample, relative to the sample prior to the enrichment procedure, is at least 25-, 50-, 75-, 100-, 150-, 200-, 250-, 300-, 350-fold, and suitably is 100-200 fold. In specific embodiments, antibodies to surface markers on IEC-interacting cells may be attached to a solid support to allow for separation. Procedures for separation may include magnetic separation, using antibody magnetic beads (e.g., Miltenyi™ beads), affinity chromatography, "panning" with antibody attached to a solid matrix or any other convenient technique such as Laser Capture Microdissection. In specific embodiments, the IEC-interacting cells are dendritic cells that are suitably enriched using an antibody that is specific for CD11c, which antibody is conjugated to a magnetic bead, and a magnetic cell separation device to separate out the CD11c$^+$ cells. Other techniques providing particularly accurate separation include FACS. Once cells are deposited on slides, they may be fixed, and probed with labeled antigen-binding molecule such as a labeled antibody for detection of Th1 immune status biomarker in a cell specific fashion.

Antibodies specific for a Th1 immune status biomarker, for example, anti-PD-L2 antibodies, may be directly conjugated to fluorescent markers, including fluorescein, FITC, rhodamine, Texas Red, Cy3, Cy5, Cy7, and other fluorescent markers, and viewed in a fluorescent microscope, equipped with the appropriate filters. Antibodies may also be conjugated to enzymes, which upon addition of an appropriate substrate commence a reaction providing a coloured precipitate over cells with detected PD-L2 protein. Slides may then be viewed by standard light microscopy. Alternatively, primary antibodies specific for PD-L2 may be further bound to secondary antibodies conjugated to the detectable moieties. Cell surface expression can be thus assessed, and the addition of cell permeabilization solutions, such as Triton-X and saponin may be applied to facilitate reagent penetration within cell cytoplasms ("Cell Biology: A Laboratory Handbook", Volumes 1-111 Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980)).

Immunohistochemistry is quite similar to immunofluorescence or immunocytochemistry, in principle, however tissue specimens are probed with PD-L2 antibody, for example, as opposed to cell suspensions. Biopsy specimens are fixed and processed and optionally embedded in paraffin, sectioned if needed, providing cell or tissue slides subsequently probed with heparanase specific antibodies. Alternatively, frozen tissue may be sectioned on a cryostat, with subsequent antibody probing, obviating fixation-induced antigen masking. Antibodies, as in immunofluorescence or immunocytochemistry, are coupled to a detectable moiety, either fluorescent, or enzyme-linked, and are used to probe tissue sections by methods described for immunofluorescence, and are subsequently visualized by fluorescent or confocal microscopy, depending upon the detection method employed. Visualization of a reaction product precipitate may be viewed by standard light microscopy, if an enzymatic detectable moiety was utilized, following development of the reaction product ("Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980)).

In specific embodiments, FACS analysis is used to assess Th1 immune status biomarker expression (e.g., PD-L2, and optionally PD-L1, expression). A general description of FACS apparatus and methods in provided in U.S. Pat. Nos. 4,172,227; 4,347,935; 4,661,913; 4,667,830; 5,093,234; 5,094,940; and 5,144,224. Cells are introduced into the FACS machine and are delivered via tubing into the FACS cell, which they pass through as single cells. A laser beam is directed at the FACS cell, and forward laser scatter is collected by a photodiode, side laser scatter is directed to a PMT tube via a lens, directed to PMT1. Specific filters direct fluorescence from the side scatter to other PMT tubes for multivariate analysis. Side laser scatter is a reflection of cell size and granularity, and may be used to identify cell populations in mixed samples. Cells labeled with fluorescent anti-PD-L2 antibody may be detected by laser excitation and collection via PMT tubes, which can be identified for cell type via size and granularity, or via incorporation of additional cell surface markers for identification, as for example disclosed above. Typically, FACS analysis is used for determination of cell surface expression of a particular protein (e.g., PD-L2, and optionally PD-L1, expression), and hence specific antibodies may be utilized for probing detection of cell surface biomarker expression in antigen-presenting cell populations (e.g., PD-L2, and optionally PD-L1, expression on the surface of dendritic cells). Specific antigen-presenting cell subtypes (e.g., CD11c$^+$ dendritic cells) expressing surface PD-L2 protein and optionally PD-L1 may be ascertained by size and granularity characteristics, or alternatively by co-staining with additional cell surface marker proteins.

In specific embodiments, protein-capture arrays that permit simultaneous detection and/or quantification of a large number of proteins are employed. For example, low-density protein arrays on filter membranes, such as the universal protein array system (Ge, 2000 *Nucleic Acids Res.* 28(2):e3) allow imaging of arrayed antigens using standard ELISA techniques and a scanning charge-coupled device (CCD) detector. Immune-sensor arrays have also been developed that enable the simultaneous detection of clinical analytes. It is now possible using protein arrays, to profile protein expression in bodily fluids, such as in sera of healthy or diseased subjects, as well as in subjects pre- and post-drug treatment.

Exemplary protein capture arrays include arrays comprising spatially addressed antigen-binding molecules, commonly referred to as antibody arrays, which can facilitate extensive parallel analysis of numerous proteins defining a proteome or subproteome. Antibody arrays have been shown to have the required properties of specificity and acceptable background, and some are available commercially (e.g., BD Biosciences, Clontech, Bio-Rad and Sigma). Various methods for the preparation of antibody arrays have been reported (see, e.g., Lopez et al., 2003 J. Chromatogram. B 787:19-27; Cahill, 2000 *Trends in Biotechnology* 7:47-51; U.S. Pat. App. Pub. 2002/0055186; U.S. Pat. App. Pub. 2003/0003599; PCT publication WO 03/062444; PCT publication WO 03/077851; PCT publication WO 02/59601; PCT publication WO 02/39120; PCT publication WO 01/79849; PCT publication WO 99/39210). The antigen-binding molecules of such arrays may recognize at least a subset of proteins expressed by a cell or population of cells, illustrative examples of which include growth factor receptors, hormone receptors, neurotransmitter receptors, catecholamine receptors, amino acid derivative receptors, cytokine receptors, extracellular matrix receptors, antibodies, lectins, cytokines, serpins, proteases, kinases, phosphatases, ras-like GTPases, hydrolases, steroid hormone receptors, transcription factors, heat-shock transcription factors, DNA-binding proteins, zinc-finger proteins, leucine-zipper proteins, homeodomain proteins, intracellular signal transduction modulators and effectors, apoptosis-related factors, DNA synthesis factors, DNA repair factors, DNA recombination factors and cell-surface antigens.

Individual spatially distinct protein-capture agents are typically attached to a support surface, which is generally planar or contoured. Common physical supports include glass slides, silicon, microwells, nitrocellulose or PVDF membranes, and magnetic and other microbeads.

Particles in suspension can also be used as the basis of arrays, providing they are coded for identification; systems include color coding for microbeads (e.g., available from Luminex, Bio-Rad and Nanomics Biosystems) and semiconductor nanocrystals (e.g., QDots™, available from Quantum Dots), and barcoding for beads (UltraPlex™, available from Smartbeads) and multimetal microrods (Nanobarcodes™ particles, available from Surromed).

Beads can also be assembled into planar arrays on semiconductor chips (e.g., available from LEAPS technology and BioArray Solutions). Where particles are used, individual protein-capture agents are typically attached to an individual particle to provide the spatial definition or separation of the array. The particles may then be assayed separately, but in parallel, in a compartmentalized way, for example in the wells of a microtiter plate or in separate test tubes.

In operation, a protein sample, which is optionally fragmented to form peptide fragments (see, e.g., U.S. Pat. App. Pub. 2002/0055186), is delivered to a protein-capture array under conditions suitable for protein or peptide binding, and the array is washed to remove unbound or non-specifically bound components of the sample from the array. Next, the presence or amount of protein or peptide bound to each feature of the array is detected using a suitable detection system. The amount of protein bound to a feature of the array may be determined relative to the amount of a second protein bound to a second feature of the array. In certain embodiments, the amount of the second protein in the sample is already known or known to be invariant.

In specific embodiments, the Th1 immune status biomarker is a target polypeptide whose level is measured using at least one antigen-binding molecule that is immune-interactive with the target polypeptide. In these embodiments, the measured level of the target polypeptide is normalized to the level of a reference polypeptide. Suitably, the antigen-binding molecule is immobilized on a solid or semi-solid support. In illustrative examples of this type, the antigen-binding molecule forms part of a spatial array of antigen-binding molecule. In some embodiments, the level of antigen-binding molecule that is bound to the target polypeptide is measured by immunoassay (e.g., using an ELISA).

Demonstration of the absence or presence of biomarker activity within a sample is an additional means of distinguishing IEC-interacting expressing a specific Th1 immune status biomarker versus non-expressing cell populations.

8.4 Evaluation of PD-L2 Biomarker Clustering

The present inventors have also determined that clustering of PD-L2 on the cell surface of IEC-interacting cells is indicative of a normal or elevated Th1 immune response. Thus, in some embodiments the biomarker value of the Th1 immune status biomarker is indicative of the level or abundance of PD-L2, as determined by analyzing the PD-L2 clustering on the cell surface of an IEC-interacting cells such as APCs (e.g., dendritic cells) or tumor cells.

There are a number of widely available assays to detect clustering of PD-L2 on the cell surface of an antigen-presenting cell (e.g., a dendritic cell). For example, PD-L2 ligands and/or PD-L2-specific antibodies can be labeled, and these labels detected to visualize clustering of PD-L2. In one example of this type of assay, a dendritic cell or tumor cell comprising the PD-L2 is contacted with a PD-L2-specific antibody, and a fluorescently labeled secondary antibody that binds to the PD-L2-specific antibody. Using confocal scanning laser microscopy, fluorescence emitted from the secondary antibody can be detected to identify the location of the PD-L2. (Van Steensel, et al., 1995. *J Cell Sci* 108: 3003-3011). In another example, a cell comprising PD-L2 on the cell surface is contacted with a labeled ligand of the cell surface PD-L2 and cell surface PD-L2 clustering analyzed by super resolution microscopy, as described for example by Kaufmann et al. (2011. *J Microsc.* 242(1):46-54), Huber et al. (2011. *PLoS One.* 7(9):e44776), Wang et al. (2014. *Biochim Biophys Acta.* 1838(4):1191-1198), and Sams et al. (2014. *J Biomed Opt.* 19(1):011021).

Alternatively, cell surface PD-L2 clustering is analyzed by in situ proximity assay as described for example by Bellucci et al. (2014. *Methods Mol Biol.* 1174:397-405), Barros et al. (2014. *Breast Cancer Res Treat.* 144(2):273-85) and Pacchiana et al. (2014. *Histochem Cell Biol.* 142(5): 593-60).

In other embodiments, FRET and FRAP microscopy can be employed to analyze PD-L2 clustering, as described for example by Wallrabe et al. (2003. *Biophys J.* 85(1):559-571), Wallrabe et al. (2003. *J Biomed Opt.* 8(3):339-346) and de Heus et al. (2013. *Methods Cell Biol.* 117:305-321).

Other methods of analyzing PD-L2 clustering include: image correlation spectroscopy as described for example by Petersen et al. (1998. *Faraday Discuss.* (111):289-305), Kozer et al. (2013. *Mol Biosyst.* 9(7):1849-1863), and Ciccotosto et al. (2013. *Biophys J.* 104(5):1056-1064); electric field analysis, as described for example by Giugni et al. (1987. *J Cell Biol.* 104(5):1291-1297), and Zhang et al. (2011. *PLoS One.* 6(10):e26805), electron microscopy, as described for example by Plowman et al. (2005. *Proc Natl Acad Sci USA.* 102(43):15500-15505), and D'Amico et al. (2008. *Micron.* 39(1):1-6); electron cryotomography, as described for example by Gold et al. (2014. *Nat Commun.* 5:4129); nanoparticle (NP) immunolabeling in combination with plasmon coupling microscopy (PCM), as described for example by Wang et al. (2012. *Nano Lett.* 12(6):3231-3237) and Rong et al. (2012. *PLoS One.* 7(3):e34175); enzyme-mediated activation of radical source (EMARS) analysis, as described for example by Miyagawa-Yamaguchi et al. (2014. *PLoS One.* 9(3):e93054) and Kotani et al. (2008. *Proc Natl Acad Sci USA.* 105(21):7405-7409); and quantum dots analysis, as described for example by Li et al. (2010. *Biophys J.* 98(11):2554-2563).

Numerous ligands with specificity for PD-L2 are known, which can be used for clustering analysis. Many of these are also useful as therapeutic agents in accordance with the present invention. For example, any suitable antibody that binds a PD-L2 polypeptide is contemplated for use in the practice of the present invention. Non-limiting examples of such antibodies are listed above.

In specific embodiments, the antibody comprises an Fc region of an immunoglobulin. Alternatively, or in addition, the antibody is a multivalent (e.g., bivalent) antibody.

Any PD-L2 ligand is suitable for use in these embodiments of the invention, including the following classes of ligand: protein, small organic molecule, carbohydrates (including polysaccharides), polynucleotide, lipids, etc. Representative examples of such ligands include PD-1 polypeptides, galectin-9 polypeptides, and repulsive guidance molecule b (RGMb).

8.5 Evaluation of Th1 Immune Status Biomarker Nucleic Acids

In some embodiments, biomarker expression is monitored by determining biomarker nucleic acid transcript levels in IEC-interacting cells such as APCs (e.g., dendritic cells) or tumor cells. RNA may be extracted from biological samples via a number of standard techniques (see *Current Protocols in Molecular Biology*" Volumes I-III Ausubel, R. M., ed. (1994); Ausubel et al., "*Current Protocols in Molecular Biology*", John Wiley and Sons, Baltimore, Md. (1989)). Guanidium-based methods for cell lysis enabling RNA isolation, with subsequent cesium chloride step gradients for separation of the RNA from other cellular macromolecules, followed by RNA precipitation and resuspension, is an older, less commonly employed method of RNA isolation (Glisin, Ve. et al., (1973) *Biochemistry* 13: 2633). Alternatively, RNA may be isolated in a single step procedure (U.S. Pat.

No. 4,843,155, and Puissant, C. And Houdebine L. M. (1990) *Biotechniques* 8: 148-149). Single step procedures include the use of Guanidium isothiocyanate for RNA extraction, and subsequent phenol/chloroform/isoamyl alcohol extractions facilitating the separation of total RNA from other cellular proteins and DNA. Commercially available single-step formulations based on the above-cited principles may be employed, including, for example, the use of the TRIZOL reagent (Life Technologies, Gaithersburg, Md.).

Th1 immune status biomarker RNA/gene expression can be monitored via a number of other standard techniques, illustrative examples of which include Northern blot and dot blot analysis, primer extension, RNase protection, RT-PCR, in-situ hybridization and chip hybridization.

Specific Th1 immune status biomarker RNA sequences can be readily detected by hybridization of labeled probes to blotted RNA preparations extracted as above. In Northern blot analysis, fractionated RNA is subjected to denaturing agarose gel electrophoresis, which prevents RNA from assuming secondary structures that might inhibit size based separation. RNA is then transferred by capillary transfer to a nylon or nitrocellulose membrane support and may be probed with a labeled oligonucleotide probe complementary to the biomarker sequence (Alwine, et al. (1977). *Proc. Natl. Acad. Sci. USA* 74: 5350-5354 and Current Protocols in Molecular Biology" Volumes I-III Ausubel, R. M., ed. (1994); Ausubel et al., "Current Protocols in Molecular Biology", John Wiley and Sons, Baltimore, Md. (1989)).

Alternatively, unfractionated RNA may be immobilized on a nylon or nitrocellulose membrane, and similarly probed for biomarker-specific expression, by Slot/Dot blot analysis. RNA slot/dot blots can be prepared by hand, or alternatively constructed using a manifold apparatus, which facilitates comparing hybridization signals by densitometry scanning (Chomczynski P. (1992) *Anal. Biochem.* 201: 134-139).

Primer extension is another means whereby quantification of the RNA may be accomplished. Primer extension provides an additional benefit in mapping the 5' terminus of a particular RNA, by extending a primer using the enzyme reverse transcriptase. In this case, the primer is an oligonucleotide (or restriction fragment) complementary to a portion of the biomarker mRNA. The primer is end-labeled, and is allowed to hybridize to template biomarker mRNA. Once hybridized, the primer is extended by addition of reverse transcriptase, and incorporation of unlabeled deoxynucleotides to for a single-stranded DNA complementary to template biomarker mRNA. DNA is then analysed on a sequencing gel, with the length of extended primer serving to map the 5' position of the mRNA, and the yield of extended product reflecting the abundance of RNA in the sample (Jones et al., (1985) *Cell* 42: 559-572 and Mierendorf R. C. And Pfeffer, D. (1987). *Methods Enzymol.* 152: 563-566).

RNase protection assays provide a highly sensitive means of quantifying biomarker RNA, even in low abundance. In protection assays, sequence-specific hybridization of ribonucleotide probes complementary to biomarker RNA, with high specific activity are generated, and hybridized to sample RNA. Hybridization reactions are then treated with ribonuclease to remove free probe, leaving intact fragments of annealed probe hybridized to homologous biomarker sequences in sample RNA. Fragments are then analysed by electrophoresis on a sequencing gel, when appropriately-sized probe fragments are visualized (Zinn K. et al., (1983) *Cell* 34: 865-879 and Melton S. A., et al., (1984). *Nucl. Acids Res.* 12: 7035-7056).

RT-PCR is another means by which biomarker expression may be analysed. RT-PCR employs the use of reverse transcriptase to prepare cDNA from RNA samples, using deoxynucleotide primers complementary to the biomarker mRNA. Once the cDNA is generated, it is amplified through the polymerase chain reaction, by the addition of deoxynucleotides and a DNA polymerase that functions at high temperatures. Through repetitive cycles of primer annealing, incorporation of deoxynucleotides facilitating cDNA extension, followed by strand denaturation, amplification of the desired sequence occurs, yielding an appropriately sized fragment that may be detected by agarose gel electrophoresis. Optimal reverse transcription, hybridization, and amplification conditions will vary depending upon the sequence composition and length(s) of the primers and target(s) employed, and the experimental method selected by the practitioner. Various guidelines may be used to select appropriate primer sequences and hybridization conditions (see, e.g., Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y.).

In-situ hybridization provides may be used for detecting and localizing cell/tissue specific biomarker RNA expression. Labeled anti-sense RNA probes are hybridized to mRNAs in cells singly, or in processed tissue slices, which are immobilized on microscope glass slides (In Situ Hybridization: Medical Applications (eds. G. R. Coulton and J. de Belleroche), Kluwer Academic Publishers, Boston (1992); In Situ Hybridization: In Neurobiology; Advances in Methodology (eds. J. H. Eberwine, K. L. Valentino, and J. D. Barchas), Oxford University Press Inc., England (1994); and In Situ Hybridization: A Practical Approach (ed. D. G. Wilkinson), Oxford University Press Inc., England (1992)). Numerous non-isotopic systems have been developed to visualize labeled DNA probes including; a) fluorescence-based direct detection methods, b) the use of digoxigenin- and biotin-labeled DNA probes coupled with fluorescence detection methods, and c) the use of digoxigenin- and biotin-labeled DNA probes coupled with antibody-enzyme detection methods. When fluorescence-labeled anti-sense RNA probes are hybridized to cellular RNA, the hybridized probes can be viewed directly using a fluorescence microscope. Direct fluorochrome-labelling of the nucleic acid probes eliminate the need for multi-layer detection procedures (e.g., antibody-based-systems), which allows fast processing and also reduces non-specific background signals, hence providing a versatile and highly sensitive means of identifying biomarker gene expression.

Chip hybridization utilizes biomarker specific oligonucleotides attached to a solid substrate, which may consist of a particulate solid phase such as nylon filters, glass slides or silicon chips (Schena et al. (1995) *Science* 270:467-470) designed as a microarray. Microarrays are known in the art and consist of a surface to which probes that correspond in sequence to gene products (such as cDNAs) can be specifically hybridized or bound at a known position for the detection of biomarker gene expression.

Quantification of the hybridization complexes is well known in the art and may be achieved by any one of several approaches. These approaches are generally based on the detection of a label or marker, such as any radioactive, fluorescent, biological or enzymatic tags or labels of standard use in the art. A label can be applied to either the oligonucleotide probes or the RNA derived from the biological sample.

In general, mRNA quantification is suitably effected alongside a calibration curve so as to enable accurate mRNA determination. Furthermore, quantifying transcript(s) originating from a biological sample is preferably effected by comparison to a normal sample, which sample is characterized by normal expression pattern of the examined transcript(s).

8.6 Deriving Biomarker Values

Biomarker values can be measured biomarker values, which are values of biomarkers directly measured for the subject, or alternatively could be "derived" biomarker values, which are values that have been derived from one or more measured biomarker values, for example by applying a function to the one or more measured biomarker values. As used herein, biomarkers to which a function has been applied are referred to as "derived biomarkers."

The biomarker values may be determined in any one of a number of ways that are well known in the art. For example, a comprehensive description of biomarker value determination can be found in Intl. Pat. Pub. No. WO 2015/117204, which is incorporated herein by reference in its entirety. In one example, the process of determining biomarker values can include measuring the biomarker values, for example by performing tests on the subject or on sample(s) obtained from the subject.

More typically, however, the step of determining the biomarker values includes having an electronic processing device receive or otherwise obtain biomarker values that have been previously measured or derived. This could include for example, retrieving the biomarker values from a data store such as a remote database, obtaining biomarker values that have been manually input, using an input device, or the like. Suitably, the indicator may be determined using a combination of a plurality of biomarker values, the indicator being at least partially indicative of Th1 immune status. Assuming the method is performed using an electronic processing device, an indication of the indicator is optionally displayed or otherwise provided to the user.

In some embodiments, biomarker values are combined, for example by adding, multiplying, subtracting, or dividing biomarker values to determine an indicator value. This step is performed so that multiple biomarker values can be combined into a single indicator value, providing a more useful and straightforward mechanism for allowing the indicator to be interpreted and hence used in determining the Th1 immune status of the subject.

It will be understood that in this context, the biomarkers used within the above-described method can define a biomarker profile for Th1 immune status, which includes a minimal number of biomarkers (e.g., at least one biomarker), whilst maintaining sufficient performance to allow the biomarker profile to be used in making a clinically relevant determination. Minimizing the number of biomarkers used minimizes the costs associated with performing diagnostic or prognostic tests and in the case of polypeptide biomarkers, allows the test to be performed utilizing relatively straightforward techniques such as fluorescence-activated cell sorting (FACS) and immunohistochemistry, and allowing the test to be performed rapidly in a clinical environment. In this regard, the indication provided by the methods described herein could be a graphical or alphanumeric representation of an indicator value. Alternatively however, the indication could be the result of a comparison of the indicator value to predefined thresholds or ranges, or alternatively could be an indication of the Th1 immune status.

Furthermore, producing a single indicator value allows the results of the test to be easily interpreted by a clinician or other medical practitioner, so that test can be used for reliable diagnosis in a clinical environment.

Solely by way of an illustration, the indicator-determining methods suitably include determining at least one biomarker value, wherein the biomarker value is a value measured or derived for at least one Th1 immune status biomarker of the subject and is at least partially indicative of a concentration or abundance of the Th1 immune status biomarker in a sample taken from the subject, and wherein the at least one Th1 immune status biomarker comprises PD-L2 of IEC-interacting cells including APCs (e.g., dendritic cells) and tumor cells. Suitably, the Th1 immune status biomarker profile further comprises PD-L1 of IEC-interacting cells such as APCs (e.g., dendritic cells) or tumor cells as a Th1 immune status biomarker. The biomarker values are typically used to determine an indicator for use in determining the Th1 immune status of a subject. In some embodiments, the indicator is indicative of a ratio of concentrations of a pair of Th1 immune status biomarkers (e.g., PD-L2 and PD-L1). Thus, if the biomarker values denote the concentrations of the Th immune status biomarker, then the derived biomarker value will typically (although not exclusively) be based on a ratio of the biomarker values.

The derived biomarker value is then used to determine the indicator, either by using the derived biomarker value as an indicator value, or by performing additional processing, such as comparing the derived biomarker value to a reference or the like, as generally known in the art and as described in more detail below.

The derived biomarker values could be combined using a combining function such as an additive model; a linear model; a support vector machine; a neural network model; a random forest model; a regression model; a genetic algorithm; an annealing algorithm; a weighted sum; a nearest neighbor model; and a probabilistic model. In some embodiments, biomarker values are measured or derived for PD-L2 and for PD-L1, and the indicator is determined by combining the biomarker values. In some embodiments, the indicator is compared to an indicator reference, with a Th1 immune status being determined in accordance with results of the comparison. The indicator reference may be derived from indicators determined for a number of individuals in a reference population. The reference population typically includes individuals having different characteristics, such as a plurality of individuals of different sexes; and/or ethnicities, with different groups being defined based on different characteristics, with the subject's indicator being compared to indicator references derived from individuals with similar characteristics. The reference population can also include a plurality of healthy individuals, a plurality of individuals known to have an enhanced Th1 immune status, a plurality of individuals known to have a reduced or deficient Th1 immune status, a plurality of individuals showing clinical signs of a cancer, suitably metastatic cancer, or a plurality of individuals showing clinical signs of a pathogenic infection (e.g., malaria).

In specific embodiments, the indicator-determining methods of the present invention are performed using at least one electronic processing device, such as a suitably programmed computer system or the like. In this case, the electronic processing device typically obtains at least one measured biomarker values, either by receiving this from a measuring or other quantifying device, or by retrieving these from a database or the like. The processing device then determines the indicator by any suitable means, for example, by calculating a value that is indicative of a ratio of concentrations of a first Th1 immune status biomarker and a second Th1 immune status biomarker.

The processing device can then generate a representation of the indicator, for example by generating a sign or alphanumeric indication of the indicator, a graphical indication of a comparison of the indicator to one or more indicator references or an alphanumeric indication of the Th1 immune status of the subject.

The indicator-determining methods of the present invention typically include obtaining a sample from a subject, who typically has at least one clinical sign of a Th1-related disease (for example, a pathogenic infection or cancer), wherein the sample includes one or more Th1 immune status biomarkers (e.g., PD-L2 and optionally PD-L1) and quantifying or otherwise assessing at least one (e.g., 1, 2, 3, 4, 5, 6, 7, 8, 9, 10 or more) of the Th1 immune status biomarkers within the sample to determine biomarker values. This can be achieved using any suitable technique, and will depend on the nature of the Th1 immune status biomarkers. Suitably, an individual measured or derived Th1 immune status biomarker value corresponds to the level, abundance or amount of a respective Th1 immune status biomarker or to a function that is applied to that level or amount. For example, if the indicator in some embodiments of the indicator-determining method of the present invention, which uses a plurality of Th1 immune status biomarkers, is based on a ratio of concentrations of a polypeptide, this process would typically include quantifying the polypeptide by any means known in the art, including immunofluorescence, or by a functional assay.

In some embodiments, the Th1 immune status of a subject is established by determining one or more Th1 immune status biomarker values, wherein an individual Th1 immune status biomarker value is indicative of a value measured or derived for a Th1 immune status biomarker in a subject or in a sample obtained from the subject. These biomarkers are referred to herein as "sample Th1 immune status biomarkers." In accordance with the present invention, a sample Th1 immune status biomarker corresponds to a reference Th1 immune status biomarker (also referred to herein as a "corresponding Th1 immune status biomarker"). By "corresponding Th1 immune status biomarker" is meant a Th1 immune status biomarker that is structurally and/or functionally similar to a reference Th1 immune status biomarker as set forth for example in SEQ ID NO:1 (PD-L2) and SEQ ID NO: 56 (PD-L1). Representative corresponding Th1 immune status biomarkers include expression products of allelic variants (same locus), homologues (different locus), and orthologues (different organism) of reference Th1 immune response biomarker genes. Nucleic acid variants of reference Th1 immune status biomarker genes and encoded Th1 immune status biomarker polypeptides can contain nucleotide substitutions, deletions, inversions and/or insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference Th1 immune status polypeptide.

Corresponding Th1 immune status biomarkers include amino acid sequences that display substantial sequence similarity or identity to the amino acid sequence of a reference Th1 immune status biomarker polypeptide. In general, an amino acid sequence that corresponds to a reference amino acid sequence will display at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98 or 99% sequence similarity or identity to a reference amino acid sequence selected from any one of SEQ ID NO: 1 to 9.

In some embodiments, calculations of sequence similarity or sequence identity between sequences are performed as follows:

To determine the percentage identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 30%, usually at least 40%, more usually at least 50%, 60%, and even more usually at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e., conservative substitution) at the corresponding position in the second sequence, then the molecules are similar at that position.

The percentage identity between the two sequences is a function of the number of identical amino acid residues shared by the sequences at individual positions, taking into account the number of gaps, and the length of each gap, which need to be introduced for optimal alignment of the two sequences. By contrast, the percentage similarity between the two sequences is a function of the number of identical and similar amino acid residues shared by the sequences at individual positions, taking into account the number of gaps, and the length of each gap, which need to be introduced for optimal alignment of the two sequences.

The comparison of sequences and determination of percentage identity or percentage similarity between sequences can be accomplished using a mathematical algorithm. In certain embodiments, the percentage identity or similarity between amino acid sequences is determined using the Needleman and Wunsch, (1970, *J. Mol. Biol.* 48: 444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In specific embodiments, the percent identity between nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. An non-limiting set of parameters (and the one that should be used unless otherwise specified) includes a Blossum 62 scoring matrix with a gap penalty of 12, a gap extend penalty of 4, and a frameshift gap penalty of 5.

In some embodiments, the percentage identity or similarity between amino acid or nucleotide sequences can be determined using the algorithm of E. Meyers and W. Miller (1989, *Cabios*, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J Mol Biol.*, 215: 403-10). BLAST nucleotide searches can be performed with the NBLAST program, score=100, wordlength=12 to obtain nucleotide sequences homologous to 53010 nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res*, 25: 3389-3402). When utilizing BLAST and Gapped BLAST programs, the default parameters of the respective programs (e.g., XBLAST and NBLAST) can be used.

Corresponding Th1 immune status biomarker polynucleotides also include nucleic acid sequences that hybridize to reference Th immune status biomarker polynucleotides, or to their complements, under stringency conditions described below. As used herein, the term "hybridizes under low stringency, medium stringency, high stringency, or very high stringency conditions" describes conditions for hybridization and washing. "Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. One embodiment of low stringency conditions includes hybridization in 6×sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a corresponding Th1 immune status biomarker polynucleotide is one that hybridizes to a disclosed nucleotide sequence (e.g., SEQ ID NO: 3 or SEQ ID NO: 4) under very high stringency conditions. One embodiment of very high stringency conditions includes hybridizing 0.5 M sodium phosphate, 7% SDS at 65° C., followed by one or more washes at 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

9. Kits

All the essential reagents required for detecting and quantifying the Th1 immune status biomarkers of the invention may be assembled together in a kit. In some embodiments, the kit comprises a reagent that permits quantification of at least one Th1 immune status biomarker. In some embodiments the kit comprises: (i) a reagent that allows quantification (e.g., determining the abundance or level) of a first Th1 immune status biomarker; and (ii) a reagent that allows quantification (e.g., determining the abundance or level) of a second Th1 immune status biomarker. In some embodiments, the kit further comprises (iii) an optional reagent that allows quantification (e.g., determining the abundance or level) of a third Th1 immune status biomarker; and (iv) an optional reagent that allows quantification (e.g., determining the abundance or level) of a fourth Th1 immune status biomarker. Suitably, the Th1 immune status biomarker is one or both of PD-L2 and PD-L1.

In the context of the present invention, "kit" is understood to mean a product containing the different reagents necessary for carrying out the methods of the invention packed so as to allow their transport and storage. Materials suitable for packing the components of the kit include crystal, plastic (polyethylene, polypropylene, polycarbonate and the like), bottles, vials, paper, envelopes and the like. Additionally, the kits of the invention can contain instructions for the simultaneous, sequential or separate use of the different components contained in the kit. The instructions can be in the form of printed material or in the form of an electronic support capable of storing instructions such that they can be read by a subject, such as electronic storage media (magnetic disks, tapes and the like), optical media (CD-ROM, DVD) and the like. Alternatively or in addition, the media can contain internet addresses that provide the instructions.

Reagents that allow quantification of a Th1 immune status biomarker include compounds or materials, or sets of compounds or materials, which allow quantification of the Th1 immune status biomarker. In specific embodiments, the compounds, materials or sets of compounds or materials permit determining the level or abundance of a polypeptide (i.e., a PD-L2 polypeptide).

The kits may also optionally include appropriate reagents for detection of labels, positive and negative controls, washing solutions, blotting membranes, microtiter plates, dilution buffers and the like. For example, a protein-based detection kit may include (i) a Th1 immune status biomarker polypeptide (for example, PD-L2 polypeptide and optionally a PD-L1 polypeptide, which may be used as a positive control), (ii) an antibody that binds specifically to a Th1 immune status biomarker polypeptide. Alternatively, a nucleic acid-based detection kit may include (i) a Th1 immune status biomarker polynucleotide (for example, a PD-L2 polynucleotide and optionally a PD-L1 polynucleotide, which may be used as a positive control), (ii) a primer or probe that specifically hybridizes to a Th1 immune status biomarker polynucleotide. Also included may be enzymes suitable for amplifying nucleic acids including various polymerases (reverse transcriptase, Taq, Sequenase™, DNA ligase etc. depending on the nucleic acid amplification technique employed), deoxynucleotides and buffers to provide the necessary reaction mixture for amplification. Such kits also generally will comprise, in suitable means, distinct containers for each individual reagent and enzyme as well as for each primer or probe.

In specific embodiments, the kits further include an immune-modulating agent as broadly described above and elsewhere herein.

The kit can also feature various devices (e.g., one or more) and reagents (e.g., one or more) for performing one of the assays described herein; and/or printed instructions for using the kit to quantify the expression of a Th1 immune status biomarker gene.

The reagents described herein, which may be optionally associated with detectable labels, can be presented in the format of a microfluidics card, a chip or chamber, a microarray or a kit adapted for use with the assays described in the examples or below, e.g., RT-PCR or Q PCR techniques described herein.

10. Diagnostic Methods

The indicator can also be used for determining a likelihood of the subject having a disease that is associated with an undesirable Th1 immune response status. In this case, this would typically be achieved by comparing the indicator to at least one indicator reference, the indicator reference being indicative of the disease, and determining the likelihood in accordance with the results of the comparison. Non-limiting examples of Th1-related diseases that are useful for diagnosis and treatment in accordance with the present invention include infectious diseases (particularly viral infections), and proliferative disorders (e.g. a metastatic cancer), as described for example herein.

In embodiments of this type, the at least one indicator reference is a distribution of indicators determined for a reference population. For example, if a subject presents with clinical symptoms of a pathogenic infection (e.g., hepatitis viruses, fungal infections such as *aspergillus*, human immunodeficiency virus (HIV), malaria, typhoid, cholera, herpes viruses, *chlamydia*, and HPV), then a reference group consisting of individuals with the same or a similar disease will be used to compare the indicator of the subject.

In some embodiments, a determination of the likelihood of a subject having the disease is made using more than one reference group of individuals. For example, a first reference group consisting of individuals previously diagnosed and known to have the disease of interest, and second reference group consisting of individuals diagnosed as having a healthy condition.

In other embodiments, the Th1-related disease is a proliferative or hyperproliferative condition including any malignant or pre-malignant condition or any disease arising or deriving from or associated with a functional or other disturbance or abnormality in the proliferative capacity or behaviour of any cells or tissues of the body. Thus, the methods described herein could be used to diagnose a cancer, including assessing the likelihood whether a cancer is a metastatic cancer.

In order that the invention may be readily understood and put into practical effect, particular preferred embodiments will now be described by way of the following non-limiting examples.

EXAMPLES

Example 1

Pd-L2 Expression of DCs Inversely Correlates with Malaria Severity in Humans

To determine if PD-L1 and PD-L2 influenced malarial immunity, seven malaria-naive, healthy human volunteers were infected with 1800 *P. falciparum* infected red blood cells (pRBC) and their blood examined before and seven days after challenge. The present inventors examined DCs, defined by CD11c expression, in view of their important role in pathogenesis (Wykes and Good, *Nat Rev Microbia* 6, 64-67, 2008) and since PD-L1 and PD-L2 on DCs can down-regulate immune responses by T cells (Brown et al., *J. Immunol.* 170: 1257-1266, 2003; Freeman et al., J. Exp. Med. 192: 1027-1034, 2000). In all seven volunteers, 90% of DCs expressed PD-L1 before infection, and there was no significant change in the percentage of DCs expressing this ligand by day seven of infection (FIG. 1A). In contrast, while 80% of DCs also expressed PD-L2 before infection, five of seven individuals showed a significantly reduced (17-57%) percentage of PD-L2$^+$ DCs at day seven post infection (FIG. 1B). Notably, significant inverse correlation was observed between the level of parasitemia and the ratio of percentage PD-L2 to PD-L1 expression on DCs at day seven post infection (FIG. 1C). Overall, contrary to the generally perceived role of PD-L2 as an immune inhibitor, higher frequencies of PD-L2-expressing DCs were associated was observed in individuals with lower parasitemia after infection with *P. falciparum*.

Materials and Methods

Human Studies

The method for conduct of the clinical trial (McCarthy et al., *PLoS One.* 6: e21914, 2011) (ClinicalTrials.gov identifier: NCT02389348) and the PCR method used to quantify parasitemia (Rockett et al., *Malar. J.* 10: 48, 2011) are described in detail elsewhere. Each participant gave informed consent. Seven of eight healthy volunteers (n=4 males; and n=3 females) aged 19-55 years (median age, 24 years {interquartile range, 21-37}) who participated in a study to evaluate the effectiveness of the experimental anti-malarial therapeutics OZ439 and DSM265 separately consented to participate in this sub-study, nested within the clinical trial. This study was approved by the Human Research Ethics Committee of the QIMR Berghofer Institute for Medical Research (QIMR). Volunteers received approximately 1800 P. falciparum pRBCs via intravenous injection in 2.0 mL of saline. On day seven, the day designated for commencement of treatment, participants were admitted to the study unit and administered the investigational antimalarial drug treatment after blood was collected for the study.

Example 2

Pd-L2 Expression on DCs Inversely Correlates with Malaria Severity in Mice

Figure 2:
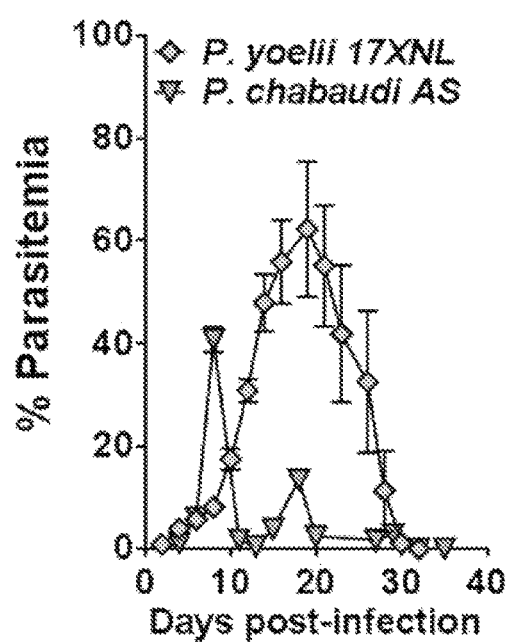
FIG. 2 is a graphical representation showing (A) mean percent parasitemia for typical courses of infection in mice infected with non-lethal $P.$ $chabaudi$ or $P.$ $yoelii$ 17XNL malaria and monitored for up to 40 days. (B) Mean percent parasitemia for typical courses of infection in mice infected with lethal $P.$ $yoelii$ YM or $P.$ $berghei$ and monitored for 10 days. Error bars represent SEM (n=4-8).
Figure 2:
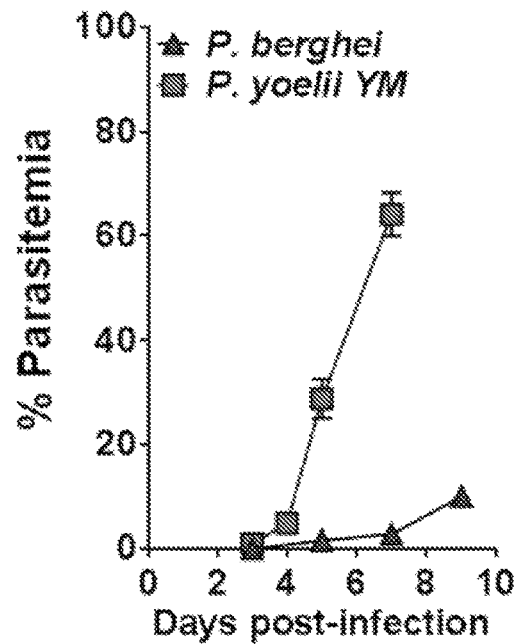

To understand the biological relevance of these data, the present inventors next investigated four mouse models of malaria. They chose four different species/strains of Plasmodium that infect mice, with each showing distinct biology and pathogenicity. When WT mice were infected with non-lethal P. yoelii 17XNL or P. chabaudi, and the blood was examined every 1-3 days for parasites, the infection progressed at different rates, but both groups cleared the infection within. 30 days (FIG. 2A). In contrast, WT mice infected with P. yoelii YM or P. berghei ANKA showed severe, but distinct disease courses (FIG. 2B; monitored as per Table 3 and 4). P. berghei parasitemia is low compared to P. yoelii YM infections because P. berghei-infected RBC sequester from the blood into deep tissues including the brain, leading to lethal cerebral disease. However, all P. yoelii YM and P. berghei-infected mice had to be euthanized within 10 days when the clinical score was ≥4 (Table 3 and 4).

Figure 3:
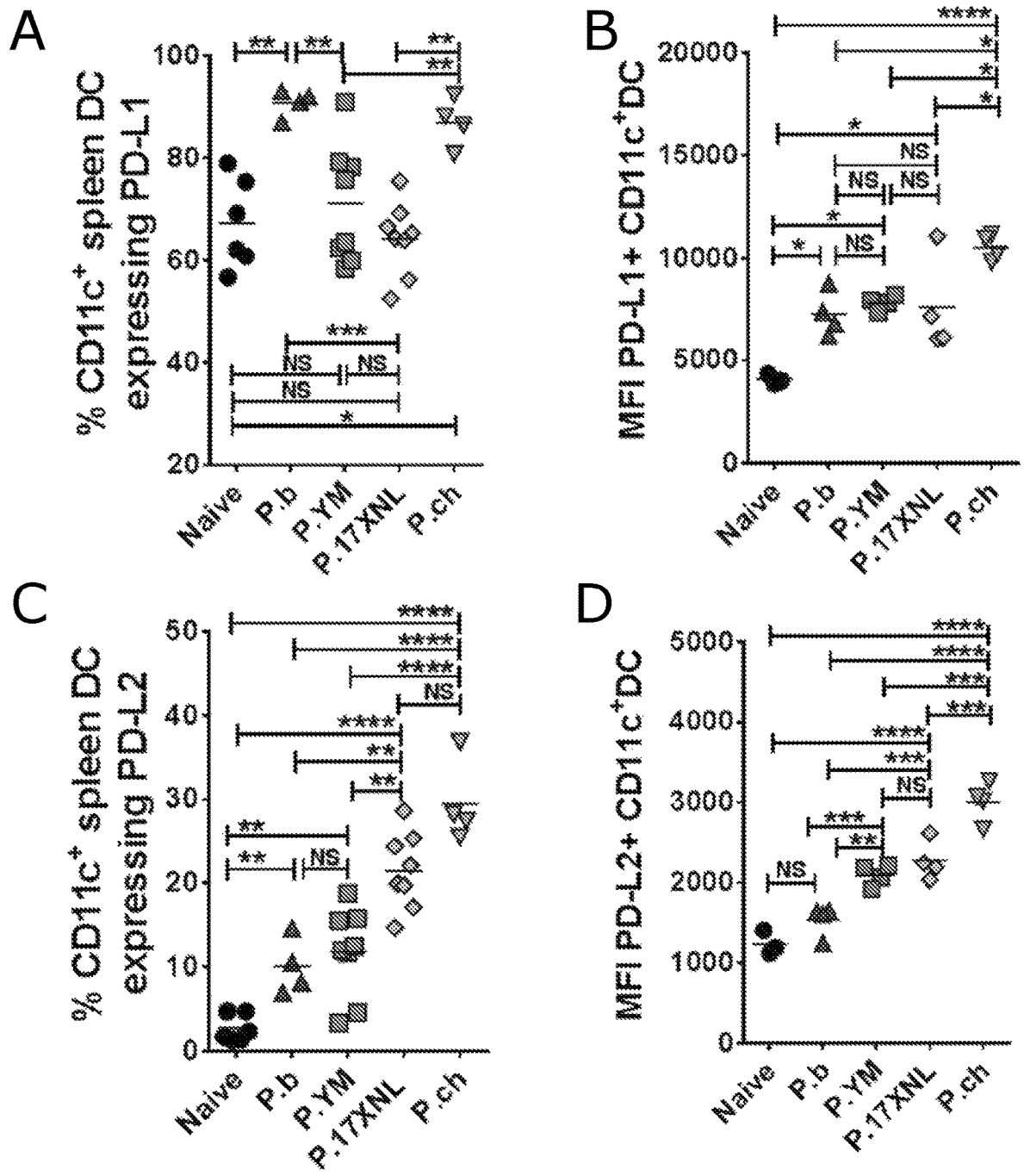
FIG. 3 is a graphical representation showing (A) the percentage of total CD11c+DC expressing PD-L1 and (B) Mean Fluorescence Intensity (MFI) of surface PD-L1-expression on PD-L1$^+$ CD11c$^+$ spleen DCs from naive and infected mice (seven days post infection). (C) Percentage of total CD11c+DC expressing PD-L2 and (D) MFI of surface PD-L2-expression on PD-L2$^+$ CD11c$^+$ spleen DCs from native and infected mice (day 7 post infection). Bars on scatter plots represent mean value. Significance between matched day 0 and day 7 human samples was analysed by Wilcoxon matched-pairs signed rank test. Significance between multiple groups was analysed using one way ANOVA with Tukey's multiple comparisons test. (* $p<0.05$;  $p<0.01$; * $p<0.001$; **** $p<0.0001$ are for comparisons between groups). Data for (A) and (C) represent pooled independent experiments in which similar results were obtained.

Surface expression of PD-L1 and PD-L2 was examined on DCs from the spleen, which has been shown to be a major site of parasite killing and regulation of parasite-specific immune responses in mice (Yadava et al., Proc. Natl. Acad. Sci. USA, 93: 4595-4599, 1996). Approximately 70% of CD11c DCs in the spleens of native mice expressed PDL1 and this percentage increased in P. berghei and P. chabaudi-infected mice but not during lethal or non-lethal P. yoelii infections (FIG. 3A). PD-L1-expressing DCs did show increases in the level of surface expression (MFI) of PD-L1I following all four malarial infections compared to DCs from native mice, with non-lethal P. chabaudi-infected mice showing the greatest increase (FIGS. 3B and 4A-F). In contrast, <5% of splenic DCs from native mice expressed PD-L2. This differed from human blood DCs that predominantly expressed PD-L2, which most likely reflects their different origins from blood and spleen. Furthermore, the percentages of PD-L2 DCs increased during all malarial infections with significantly greater percentages found in mice with non-lethal than lethal malaria (FIGS. 3C and 4A-E). The MFI of PD-L2 staining on PD-L2-expressing DCs also increased in mice infected with all but P. berghei parasites, compared to DCs from native mice (FIGS. 3D and 4A-F).

Finally, CD11c$^+$ DCs from lethal and non-lethal P. yoelii malaria showed similar increases in PD-L1 and PD-L2 mRNA levels (FIG. 4G) suggesting that the difference in PD-L2 between these parasites noted in FIG. 3C is dependent on post-transcriptional regulation or protein localization. Of note, DCs from lethal and non-lethal P. yoelii infections had the same surface levels of PD-L1 and PD-L2 expression and mRNA but differed in percentages of PD-L2+ and not PD-Li$^+$ DCs.

Overall, the results from all infections are consistent with a hypothesis that a higher percentage of PD-L2' DCs correlates with a favourable disease outcome.

Materials and Methods

Mice Studies

Specific pathogen-free C57BL/6J (wt) female mice 8-12 weeks of age were obtained from the Animal Resources Centre (Perth, Australia). Mice were housed in the QIMR animal research facility, and all procedures approved and monitored by the QIMR Animal Ethics Committee. Work was conducted under QIMR animal ethics approval number A0209-622M in accordance with the "Australian code of practice for the care and use of animals for scientific purposes" (Australian National Health & Medical Research Council). PD-1 knockout (ko) (Pdcd1$^{-/-}$) mice on a C57BL/6 background were kindly provided by Dr. T. Honjo through the Riken B R C (Nishimura et al., Science. 291: 319-322, 2001). The PD-L2 ko (Liang et al., Eur. J. Immunol. 36: 58-64, 2006), PD-L1 ko (Liang et al., Eur. J. Immunol. 36: 58-64, 2006) and PD-1 ko mice on a C57BL/6J background, used in these studies, were confirmed to have the gene deleted by PCR testing and/or flow cytometry. The sample size was estimated based on previous studies with similar assays, using the same parasites.

For experiments with multiple groups, all mice were first infected and then randomly assigned into treatment groups. No blinding was undertaken.

Parasitic Infection and Monitoring

Cohorts of 3-6 WT mice were infected intravenously with $10^5$ P. yoelii 17XNL, $10^5$ P. chabaudi AS, $10^4$ P. yoelii YM, or $10^4$ P. berghei ANKA parasitized red blood cells (pRBCs) freshly obtained from C57BL/6J mice previously infected mice. These parasite doses were previously shown to give obvious parasitemia around the same time. Tail-tip blood films were made every 1-2 days, stained using the Quick Dip modified Wright-Giemsa stain (Thermo Fisher Scientific) and examined for parasitemia, for up to 60 days. The percentage of pRBCs was assessed by counting at least 300 RBCs during parasitemia >1% and 20 fields with around 10,000 cells at other times.

The mean percentage parasitemia shown in several figures is the mean percentage pRBC of total RBC, from individual mice in a group. Mice were monitored daily for anemia, and physical symptoms of disease, including posture (hunching), lack of activity and fur texture. Mice were euthanized if they showed signs of significant distress as described in Tables 3 and 4, below.

TABLE 3

| Criteria | Grade 0 | Grade 1 | Grade 2 |
| --- | --- | --- | --- |
| Weight loss | <10% | 10 to 25% | |
| Posture | Normal | Hunching noted only at rest | Severe hunching impairs movement |
| Activity | Normal | Mild to moderately decreased | Stationary unless stimulated |
| Fur texture | Normal | Mild to moderate ruffling | Sever ruffling/poor grooming |
| Hemoglobin | Normal | <50 g/L | <20 g/L |

P. yoelii YM symptoms include anemia respiratory distress, and haematuria with complications such as coma and convulsions but never cerebral malaria. The mice are monitored daily by the above criteria for distress during the period of the experiment, to determine whether treatments described in the study are causing distress to mice to a degree to where they should be euthanized. If the cumulative score reaches above 3 by these assessment criteria, or if the weight loss is more than 25%, the distressed mouse is euthanized.

TABLE 4

| Symptoms | Score | Day post-infection |
| --- | --- | --- |
| Ruffled fur | 1 | 5 |
| Hunching | 1 | 5 |
| Wobbly gait | 1 | 6 |
| Limb paralysis | 1 | 6 |
| Convulsions | 1 | 6-7 |
| Coma | 1 | 6-7 |

*P. berghei* causes lethal cerebral disease and symptoms are usually evident by day 7 post infection. Scores are cumulative and mice with a cumulative score=4 are euthanized. Notably, ruffled fur and hunching are general clinical sigs, while other symptoms (in italics) are symptoms of cerebral malaria.

Flow Cytometry

Single-cell suspensions of processed blood or spleen cells were labeled with combinations of fluorophore-conjugated antibodies shown below. Fixable Viability Dye eFluor780 (eBioscience) was used to exclude dead cells from analysis. Serial dilutions of each antibody were pre-tested by flow cytometry to determine the optimal concentration for the main assay. Anti-CD16/32 (clone 2.4G2, BD) was used for blocking nonspecific Fc binding. Intracellular markers denoted with an asterisk were labeled following fixation and permeabilization of cells using BD Pharmingen Transcription Factor Buffer Set. Acquisition of data was performed using a BD LSR Fortessa flow cytometer and BD FACSDiva software. Analysis of data was performed using FCS express (De Novo Software) or FlowJo (Tree Star).

TABLE 5

| Marker | Antibody clone | Conjugate | Company |
| --- | --- | --- | --- |
| CD11c | N418 | BV421 | Biolegend |
|  | 3.9 | BV-605 | Biolegend |
| PD-L1 | 10F.9G2 | PE | BD |
|  | 29E.2A3 | PE-Cy7 | Biolegend |
| PD-L2 | TY25 | APC | BD |
|  | 24F.10C12 | Alexa Fluor 647 | Biolegend |
| PD-1 | RMP1-14 | PE-Cy7 | BioXell |
|  | J43 |  | eBioscience |
| CD4 | GK1.5 | Pacific Blue | Biolegend |
| CD62L | MEL-14 | BV605 | Biolegend |

Example 3

Pd-L2 is Required for Survival and Parasite Control

Figure 5:
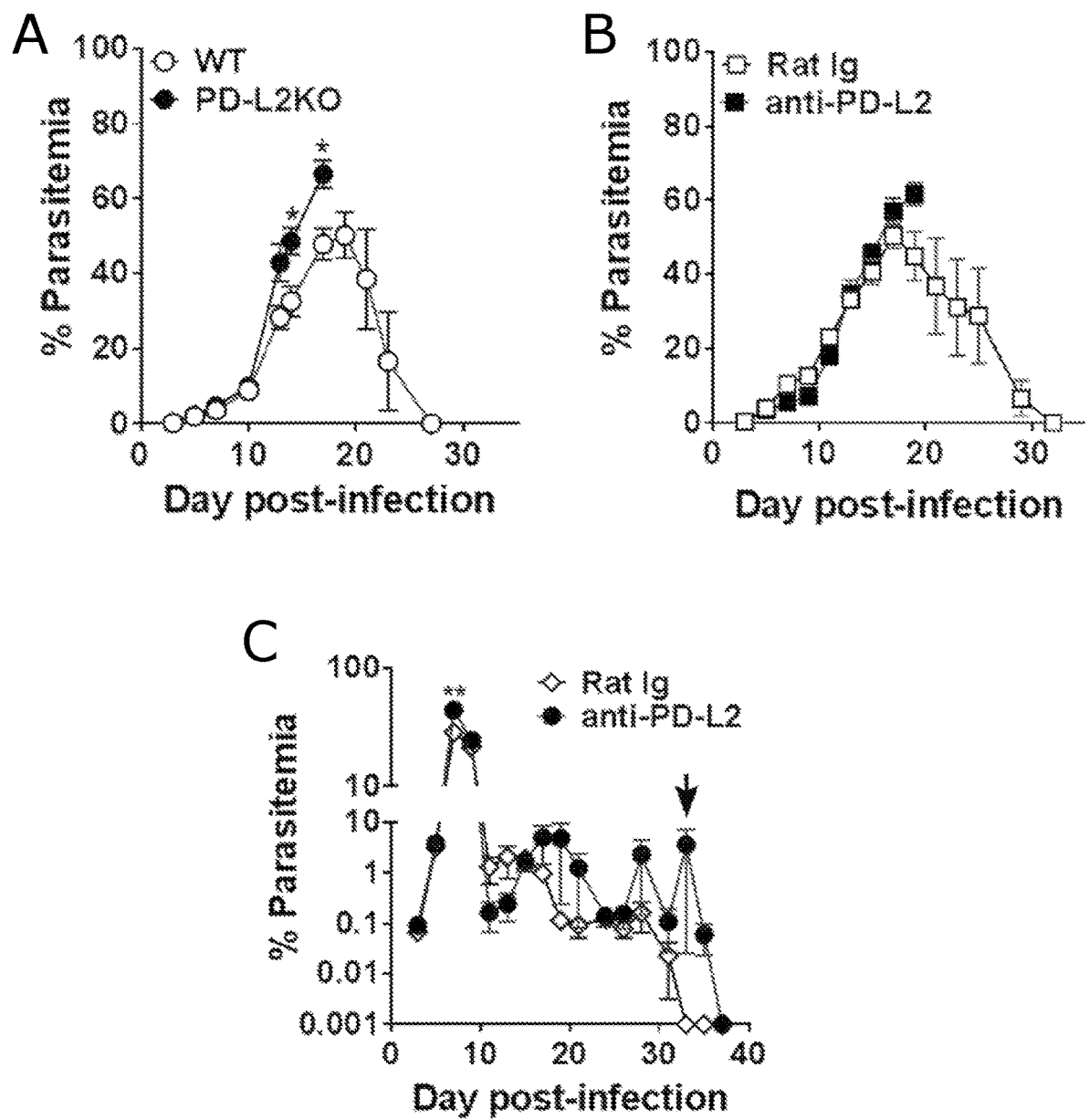
FIG. 5 is a graphical representation showing that PD-L2 improves immunity and survival from malaria infection. (A-C) mean percent parasitemia for a typical course of $P.$ $yoelii$ 17XNL malaria in (A) PD-L2 ko and wild-type mice (n=4) or (B) wild-type mice treated with Rat IgG or anti-PD-L2 blocking antibody (n=5); and (C) mean percent parasitemia (on a log scale) for a typical course of $P.$ $chabaudi$ malaria in wild-type mice treated with Rat IgG or anti-PD-L2 blocking antibody (n=5). Arrow indicates parasites were cleared four days earlier in rat IgG than anti-PD-L2-treated mice. Data represent one of two independent experiments that obtained similar results. Significance at certain time points were analysed using the non-parametric Mann-Whitney U test based on 2-sided tail. Error bars represent SEM (* $p<0.05$; ** $p<0.005$).

To determine the contribution of PD-L2 to the control of malarial parasites, the 5 present inventors next examined the outcome of *P. yoelii* 17XNL infection in PD-L2 ko mice (Liang et al., *Eur. J. Immunol.* 36: 58-64, 2006) (on a C57BL/6J background) compared with wt mice. All wt mice cleared the infection within 27 days (FIG. 5A).

Figure 6:
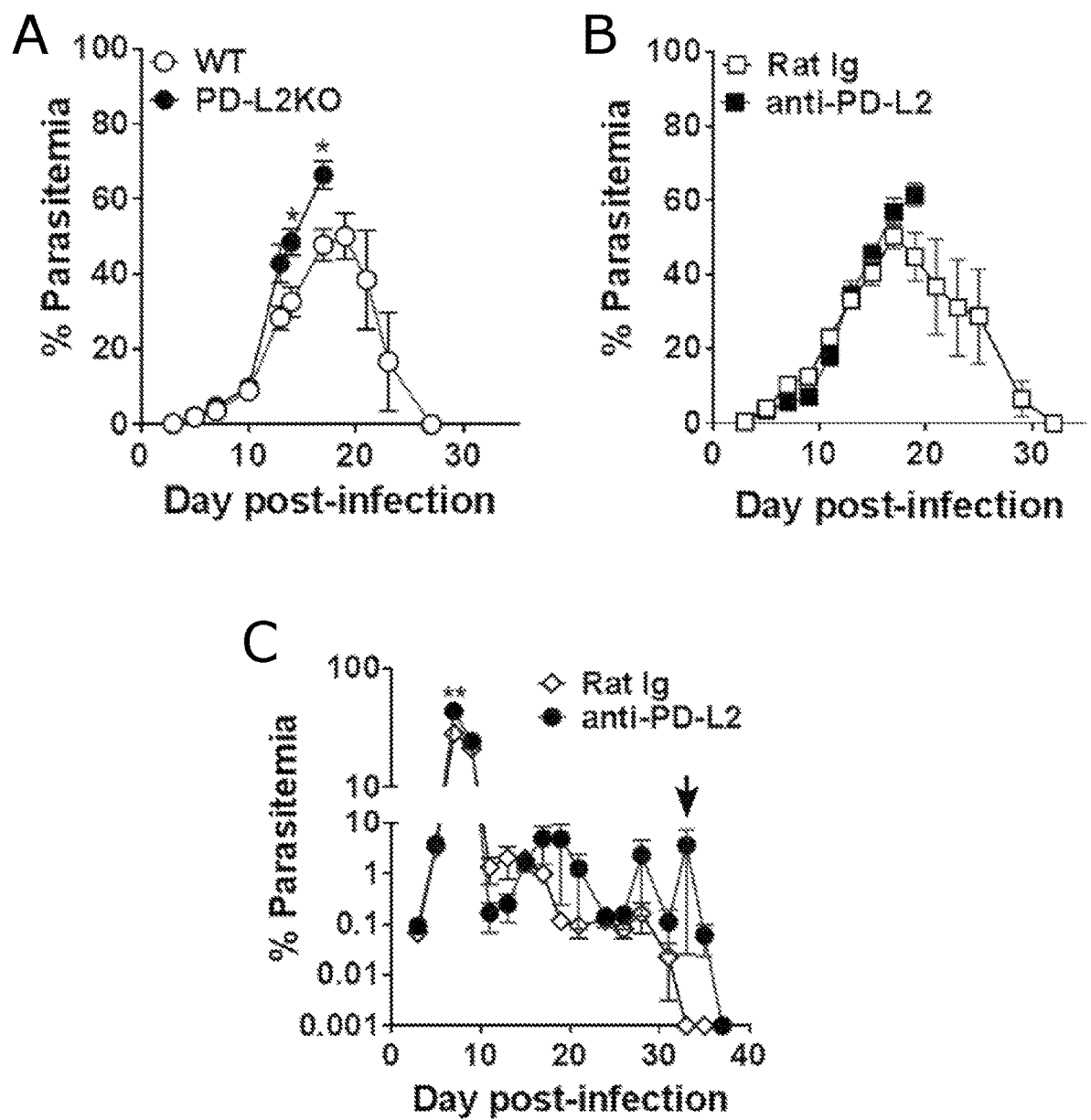
FIG. 6 is a graphical representation showing that PD-L2 regulates protection, symptoms and Th1 immunity during $P.$ $yoelii$ 17XNL malaria. (A-D) Parasitemia and clinical symptom scores from duplicate experiments for FIGS. 5A and B, during a typical course of $P.$ $yoelii$ 17XNL malaria in (A)-(B) wild-type mice and PD-L2 ko mice (n=5) or (C)-(D) wild-type mice treated with rat IgG or anti-PD-L2 blocking antibody (n=5). (E) Parasitemia during typical course of *P. chabaudi* malaria in wild-type mice treated with Rat IgG or anti-PD-L2 blocking antibody (n=5) in a duplicate experiment as described for FIG. 2C. Arrow indicates parasites were cleared three days earlier in Rat IgG than anti-PD-L2-treated mice.

However, the PD-L2 ko mice had significantly higher parasitemia than wt mice after day 13, and all of these mice died or had to be euthanized by day 19 (FIG. 5A and FIG. 6A) due to clinical scores ≥4 (FIG. 6B). Thus, PD-L2 expression is required for parasite control and survival from infection with *P. yoelii* 17XNL.

To confirm the observation that PD-L2 was required to survive *P. yoelii* 17XNL infections, the inventors next blocked PD-L2 with a monoclonal antibody when parasites became detectable in the blood. For this experiment, wt mice were infected with *P. yoelii* 17XNL and given either anti-PD-L2 or control rat IgG, four days post infection and every 3-4 days until day 14-18 post infection. All wt mice that received rat IgG survived and cleared the infection within 32 days (FIG. 5B and FIG. 6C). In contrast, 100% of the infected mice that were given the PD-L2 blocking antibody died, or were euthanized, by day 19, due to severe symptoms (FIG. 6D), although the degree of parasite control was similar in anti-PD-L2 and control antibody treated groups (FIG. 5B and FIG. 6C). This was in contrast to PD-L2 ko mice, which had significantly higher parasitemia after day 13 (FIG. 5A) suggesting either that the antibody did not completely inhibit function, or that four days of PD-L2 function, before blockade, partially improved immunity.

To further explore the role of PD-L2 in protection against another non-lethal infection, wt mice were infected with non-lethal *P. chabaudi* malaria and treated with either anti-PD-L2 or rat IgG (FIG. 5C and FIG. 6E) as for *P. yoelii* 17XNL experiments. Mice from both groups survived but blockade of PD-L2 significantly increased parasitemia during the acute infection (day 8; note log scale), led to generally higher parasitemia during the chronic phase of infection (>day 21) and delayed parasite clearance by four days (arrow indicates parasite clearance in rat IgG-treated mice; FIG. 5C). Overall, these protection/survival studies showed that PD-L2 expression was required for better control of non-lethal malarias and survival from *P. yoelii* 17XNL malaria.

Example 4

Pd-L2 Improves Parasite-Specific CD4+ T Cell Responses in Mice

Figure 7:
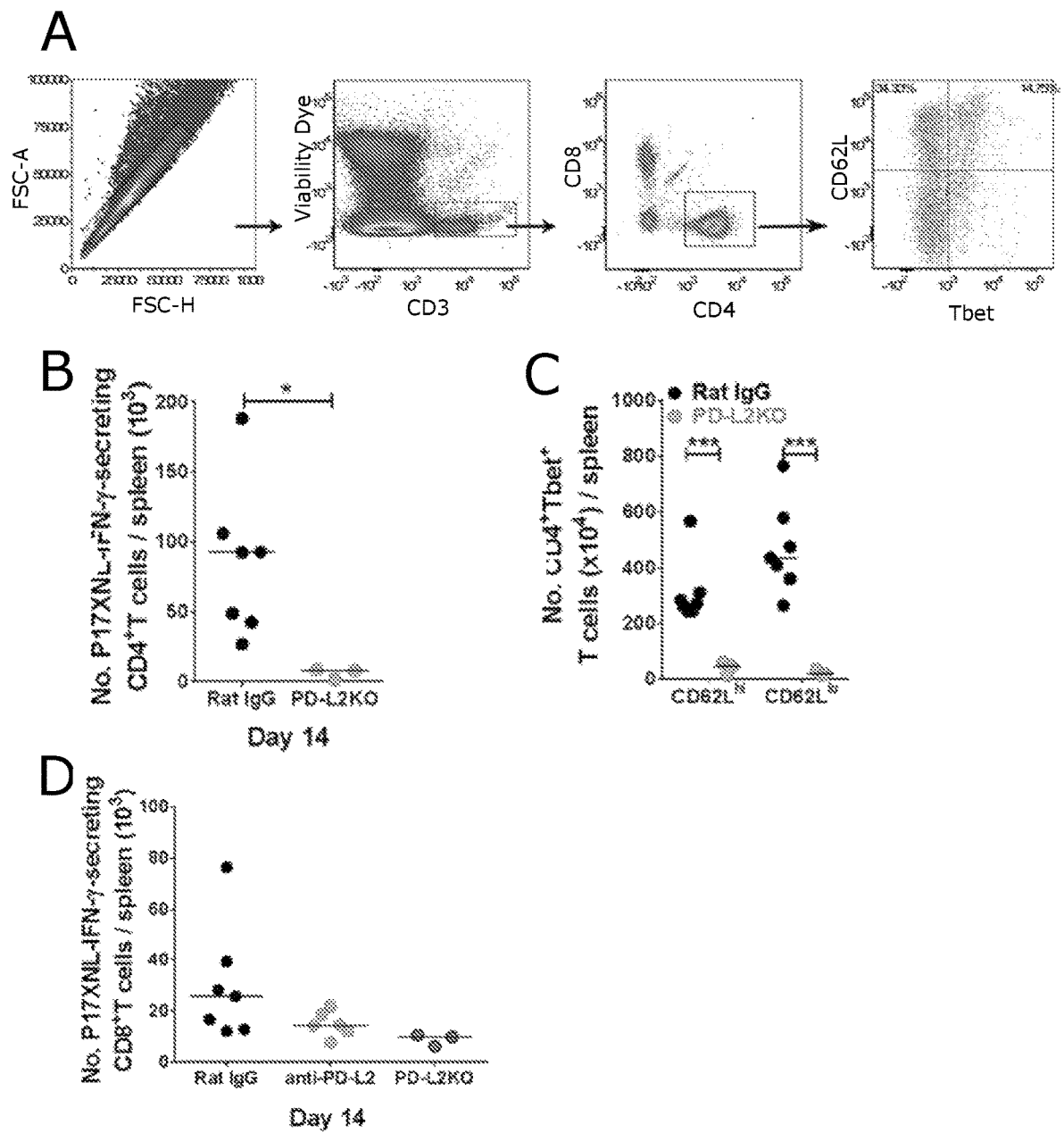
FIG. 7 is a graphical representation showing (A) the gating strategy used to assess $T_{bet}$ expression in CD4$^+$ T cells by flow cytometry. (B)-(C) Scatter plots show number of T cells per spleen, in wild-type mice treated with rat IgG (n=7) or anti-PD-L2 blocking antibody (n=7) or in PD-L2 ko mice (n=3) infected with *P. yoelii* 17XNL for 14 days. (B) Mean numbers of $T_{bet}$-expressing CD4$^+$ CD62L$^{hi}$ or CD4$^+$ CD62$^{lo}$ T cells per spleen. (C) Mean numbers of CD4$^+$ T cells per spleen, that secreted IFN-γ in an ELISPOT culture in response to parasite antigen (MSP1$_{19}$), in the presence of naive DCs. (D) Scatter plot shows number of CD8$^+$ T cells per spleen, at day 14, that secreted IFN-γ in an ELISPOT culture in response to parasite peptide (Pb1), in the presence of naive DCs. The data are pooled from 2 independent experiments except for PD-L2 ko mice which were assessed once. Significance was analysed using the non-parametric Mann-Whitney U test based on 2-sided tail. (* p<0.05; *** p<0.001).
Figure 8:
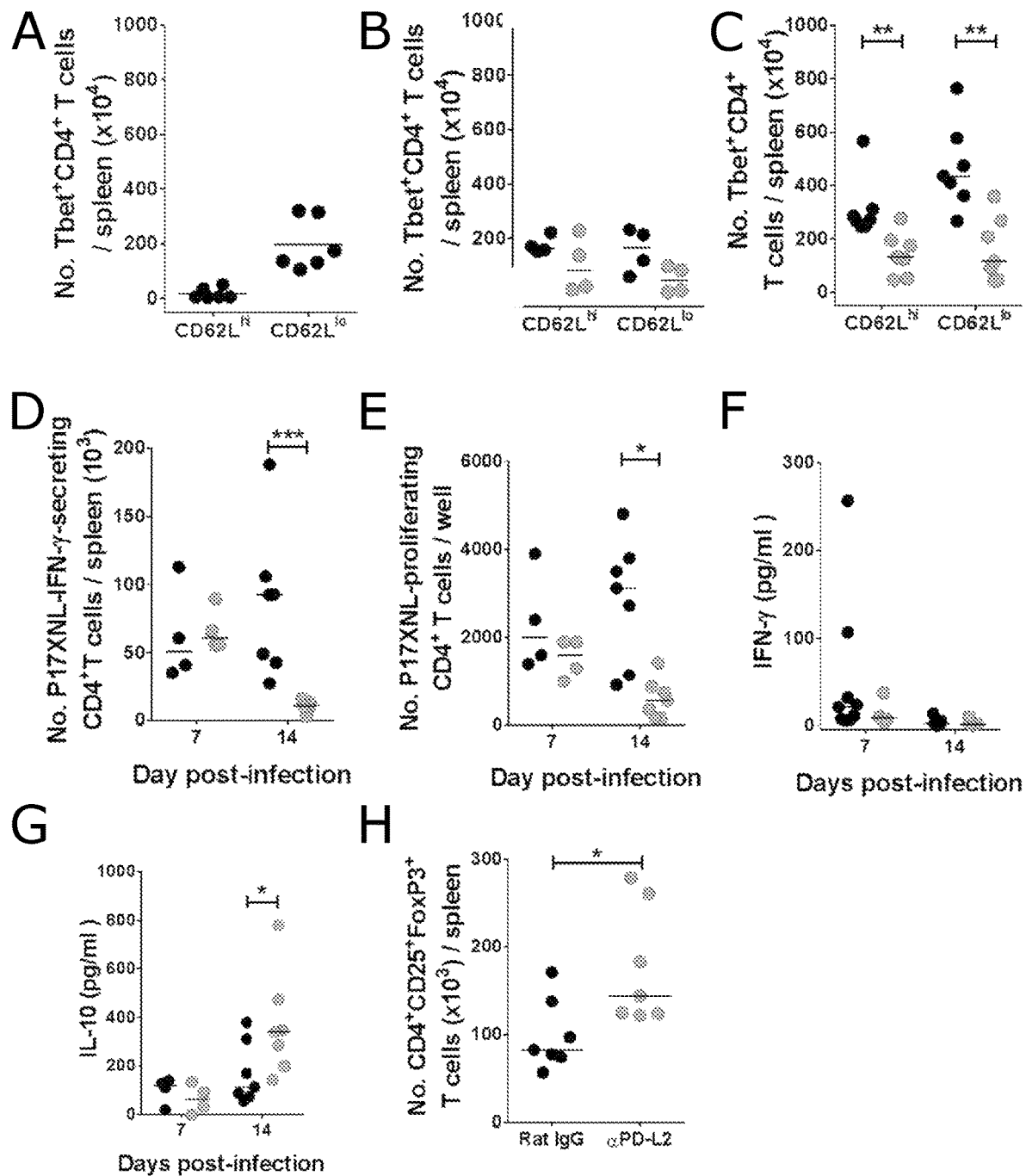
FIG. 8 is a graphical representation showing that blockade of PD-L2 inhibits the expansion of parasite-specific CD4$^+$ T cells in mice infected with *P. yoelii* 17XNL. Wild-type mice infected with *P. yoelii* 17XNL and treated with rat IgG or anti-PD-L2 blocking antibody (n=7). (A), (B), (C) Numbers of $T_{bet}$-expressing CD4$^+$ CD62L$^{hi}$ and CD4$^+$ CD62L$^\circ$ T cells per spleen on (A) day 0; (B) day 7; and (C) day 14; (D) Numbers of CD4$^+$ T cells that secreted Interferon-γ (IFN-γ) in an ELISPOT culture in response to parasite antigen (MSP1$_{19}$) in the presence of naive DCs. (E) Numbers of CD4$^+$ T cells that proliferated in cultures in response to parasite antigen MSP1$_{19}$ in the presence of naive DCs, measured by incorporation of EdU; (F) and (G) Mean levels of (F) IFN-γ; and (G) IL-10 in the serum *P. yoelii* 17XNL-infected mice. (H) Mean numbers of CD4$^+$ T cells expressing CD25 and FoxP3 (regulatory T cells) per spleen. Bar on scatter plots represent median values. The data represent two pooled independent experiments. Significance was analysed using the non-parametric Mann-Whitney U test based on two-sided tail (* p<0.05;  p<0.01; * p<0.001).

The present inventors next focused on understanding why mice did not survive infection with non-lethal *P. yoelii* 17XNL when PD-L2 was blocked. They therefore repeated the above blocking experiments and collected spleens at days 7 and 14 for evaluation by multiple immunoassays. First, CD4+ T cells were examined for the expression of $T_{bet}$, a transcription factor required for effector functions of Th1 CD4+ T cells, which are known to mediate protection against malaria (Kumar and Miller, *Immunol Lett*, 25: 109-114, 1990; Stephens and Langhorne, *PLoS Pathog*, 6: e1001208, 2010; and Su and Stevenson, *J Immunol*, 168: 1348-1355, 2002). T cells were also evaluated for expression of CD62L, a marker found on native T cells and which also distinguishes central memory ($CD62L^{hi}$) from effector memory (CD62L'O) T cells (FIG. 7A). Compared to native mice (day 0; FIG. 8A), there was a significant increase in numbers of $T_{bet}$-expressing $CD62L^{hi}$ CD4+ T cells per spleen by day 7 (FIG. 8B; p<0.0095) in control mice given Rat IgG but not mice with PD-L2 blockade (FIG. 8B; p>0.05). By day 14, the control mice had 2.2 and 3-fold more $T_{bet}$-expressing $CD62L^{hi}$ and CD62L'° CD4+ T cells per spleen, respectively, than the mice given anti-PD-L2 antibody (FIG. 8C). Similarly, control mice had >five-fold higher numbers of IFN-γ-secreting, parasite-specific CD4+ T cells at day 14 as measured by responses to parasite antigen $MSP1_{19}$ in culture, than mice with PD-L2 blockade (FIG. 8D). An in vitro EdU-uptake assay confirmed that control mice had higher numbers of parasite-specific CD4$^+$ T cells which proliferated in response to parasite antigen (FIG. 8E). However, levels of serum IFN-γ were not significantly affected by PD-L2 blockade (FIG. 8F). In contrast, mice with PD-L2 blockade had greater than two-fold more serum IL-10 than control mice by day 14 (FIG. 8G). This result correlated with a significant increase in numbers of regulatory T cells (T$_{reg}$) per spleen seen with PD-L2 blockade compared to control treated mice (FIG. 8H).

Studies with *P. yoelii* 17XNL-infected PD-L2 ko mice also found significantly lower numbers of T$_{bet}$-expressing and IFN-γ-secreting, parasite-specific CD4$^+$ T cells per spleen at day 14 compared to infected WT mice (FIGS. 7B and C). Finally, there was no significant reduction in IFN-γ-secreting, parasite-specific CD8$^+$ T cells per spleen at day 14 in infected PD-L2 ko mice or infected mice given anti-PD-L2 blocking antibody compared to infected wt mice (FIG. 7D).

Overall, the data showed that PD-L2 expression was necessary for effective Th1 CD4$^+$ T cell responses against *P. yoelii* 17XNL malaria. Given that a higher ratio of PD-L2 to PD-L1 expression on DCs was associated with lower parasitemia and blockade of PD-L2 resulted in reduced Th1 responses, it was hypothesized PD-L2 may inhibit PD-L1 functions which were reported to inhibit Th1 responses (Liang et al., *Eur. J. Immunol.* 36: 58-64, 2006). Furthermore, PD-L2 blockade caused mortality in mice infected with *P. yoelii* 17XNL but not *P. chabaudi* malaria. In alignment, PD-L1/PD-1-mediated immune suppression was previously shown to be greater during the acute phase of *P. yoelii* 17XNL (Butler et al., *Nat. Immunol.* 13: 188-195, 2012) than *P. chabaudi* malaria (Horne-Debets et al., *Cell. Reports.* 5: 1204-1213, 2013). As such, we concluded that PD-L2-mediated inhibition of PD-L1/PD-1-mediated immune suppression, could explain the different outcomes of PD-L2 blockade between the two infections.

Example 5

Pd-L1 and Pd-L2 Co-Expression on DCs Determine Immunity

Figure 9:
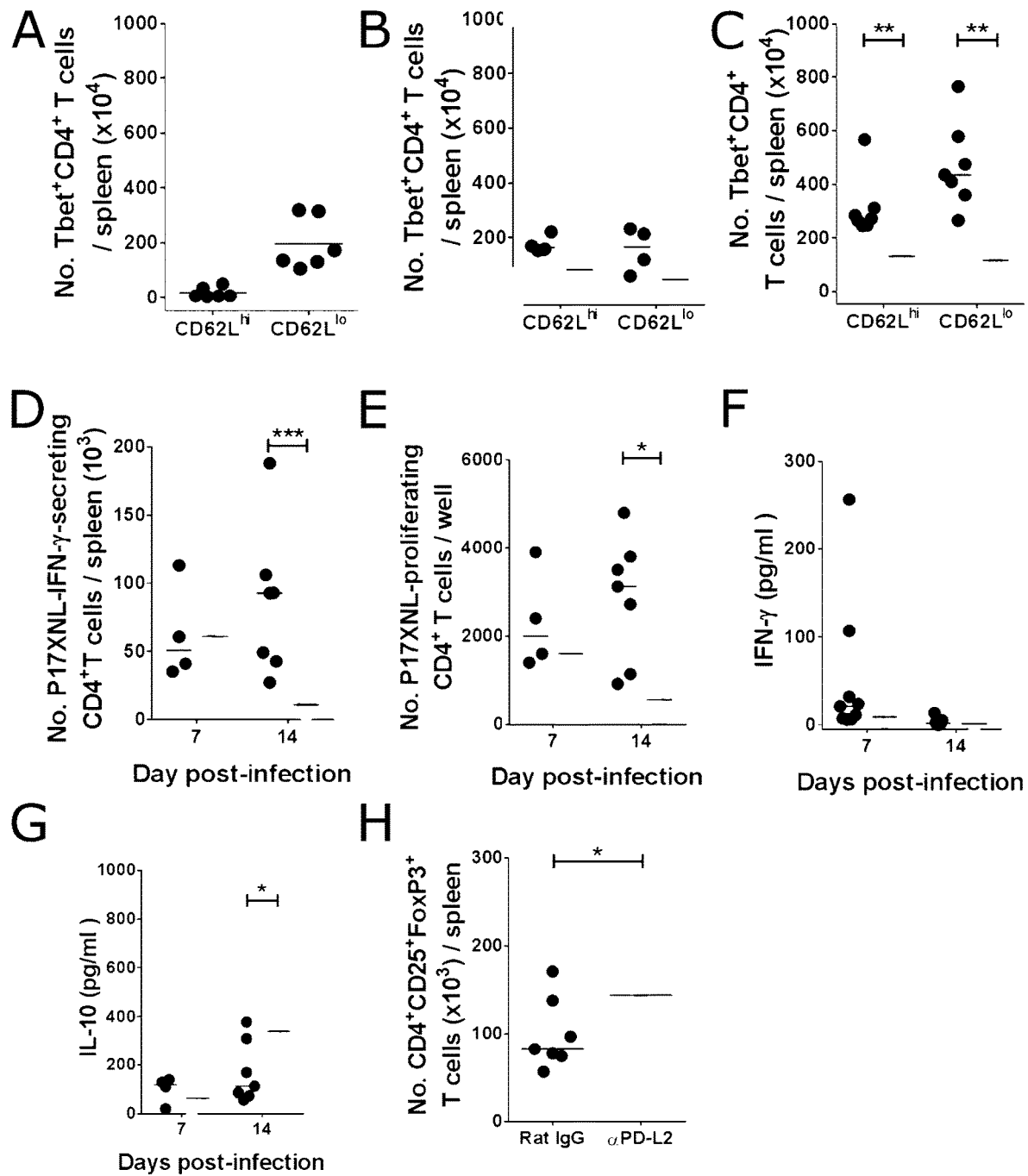
FIG. 9 is a graphical representation showing the differential effect of DC-expressed PD-L1 and PD-L2 on T cells and immunity. Flow cytometry profiles of CD19-CD3-CD11c+DC from (A) wild-type; and (B) PD-L1 ko mice, taken at day 7 of a lethal *P. yoelii* YM infection and labeled for markers of DC sub-populations (CD4$^+$; CD8$^+$; B220$^+$ pDC; and CD11b$^+$ DC). (C) Survival curves showing protection against lethal malaria by DCs without PD-L1 expression. Wile-type and PD-L1 ko mice were infected with lethal dose of 10$^4$ *P. yoelii* YM pRBC, DCs were isolated from infected (drug-cured) mice and 1×10$^7$ DCs were transferred to each mouse in groups of four naive mice, in duplicate experiments. After 24 hours, each mouse was infected with 10$^4$ *P. yoelii* YM pRBC, and survival monitored every 1-3 days for 50 days. (D)-(E) Duplicate experiments in which parasitemia in naïve mice transfused with ~1×10$^7$ DC from wild-type and PD-L1 ko mice, taken at day 7 of a lethal *P. yoelii* YM infection. After 24 hours, each transfused mouse was infected with 10$^4$ *P. yoelii* YM pRBC and monitored every 1-3 days for 50 days. Results are mean±SEM, n=4 mice/group. (F) Survival curves showing PD-1 ko mice are immune to lethal malaria. Groups of five wild-type and PD-1 ko mice were infected with lethal 10$^4$ *P. yoelii* YM pRBC and survival monitored every 1-3 days for 50 days in duplicate experiments. (G)-(H) Duplicate experiments in which parasitemia in wild-type and PD-1 ko mice infected with 10$^4$ *P. yoelii* YM pRBC and monitored every 1-3 days for 50 days. Results are mean±SEM, n=5 mice/group. (I)-(M) Flow cytometry analysis of CD3 and ICOS expression on CD4$^+$ CD62L'O PD-1$^+$ T cells cultured with DCs expressing PD-L1 and PD-L2; wherein (I) is a negative control comprising only T cells without DCs; (J) is a positive control comprising T cells and DCs; (K) blockade of PD-1; (L) blockade of PD-L1; and (G) blockade of PD-L2; after 36 hours. Both T cells and DCs were isolated from the spleens of mice infected with *P. yoelii* 17XNL for 12-14 days. Gates to determine high CD3 or ICOS expression were chosen based on clear double peaks found in anti-PD-L1 cultures. (N) Scatter plots showing percentages of CD4$^+$ CD62$^{lo}$ T cells/well with high CD3 and ICOS expression in replicate wells (n=3-5) from three independent experiments shown as white, pale blue and darker blue spots. Error bars represent mean. Significance was analysed using the unpaired t-test (one-sided tail) from one of the three experiments (* p<0.05;  p<0.005; * p<0.0005; **** p<0.0001).
Figure 9:
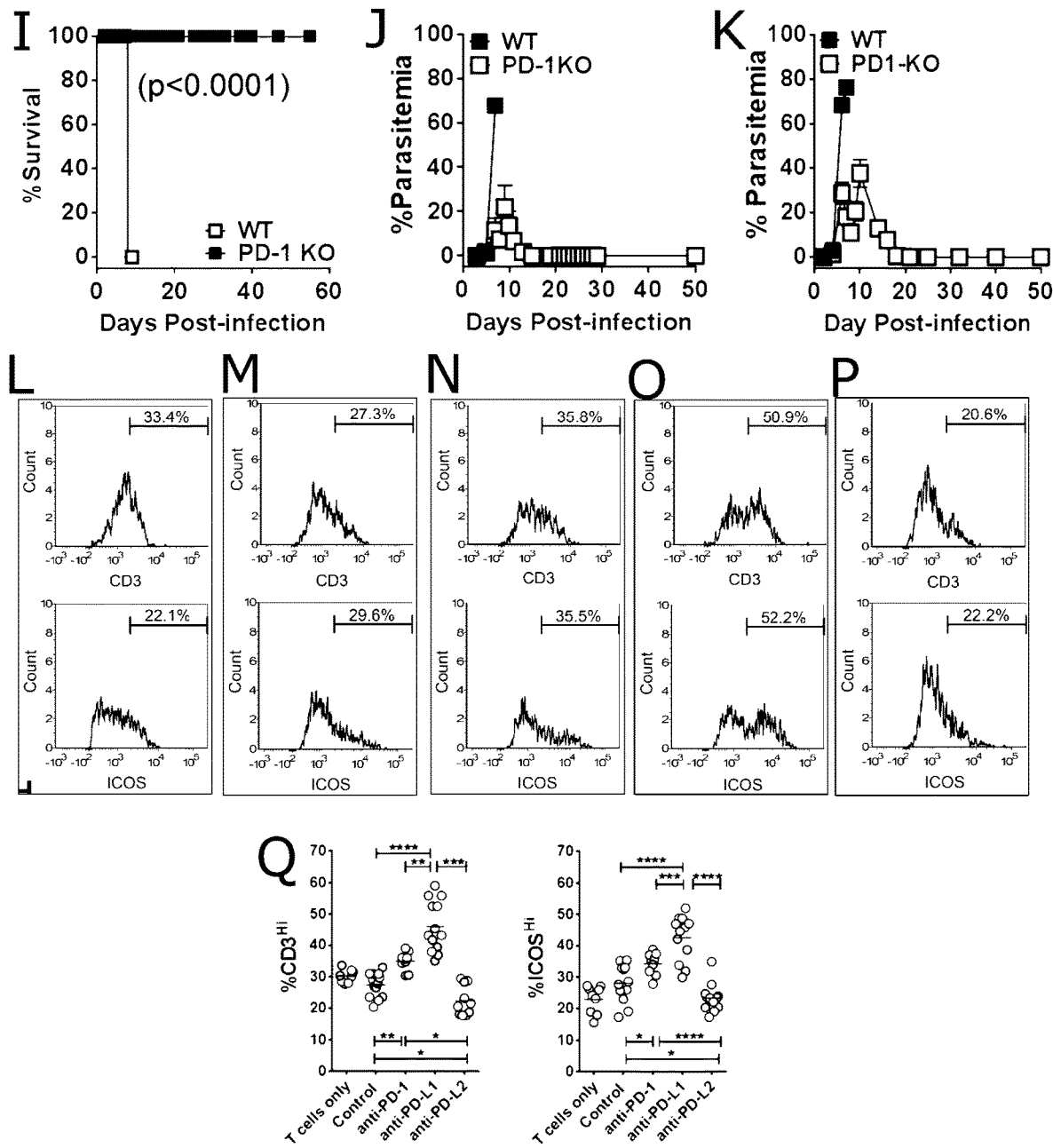

The present inventors next undertook DC-transfer studies to establish if PD-L1 expression on DCs was responsible for lethality of malaria. To do so, wt and PD-L1 ko mice were infected with lethal *P. yoelii* YM malaria, DCs isolated at day 7 post infection (FIGS. 9A and eB) and transferred to native mice which were then infected with lethal *P. yoelii* YM malaria. While 100% mice given DCs from wt mice had to be euthanized within ten days due to clinical scores 4, all mice given DCs from PD-L1 ko mice survived (FIG. 9C) and cleared the infection (FIGS. 9D and 9E). This transfer study showed that PD-L1 on DCs was mediating lethality as mice given DCs with abundant PD-L1 but little PD-L2 (see, FIGS. 3A, C and FIG. 4D) did not survive, while all mice given PD-L1 ko DCs survived.

WT and PD-I ko mice were then infected with lethal *P. yoelii* YM to confirm that the PD-1 pathway was responsible for the lethality of *P. yoelii* YM malaria. While 100% of WT had to be euthanized by day 10 due to clinical scores ≥4, all PD-1 ko mice survived (FIG. 9F) and cleared the infection (FIGS. 9G and 9H) confirming that the PD-1/PD-L1 pathway was driving lethality of *P. yoelii* YM infections. Overall, these studies showed PD-1 and PD-L1 mediated lethality of malaria.

Figure 4:
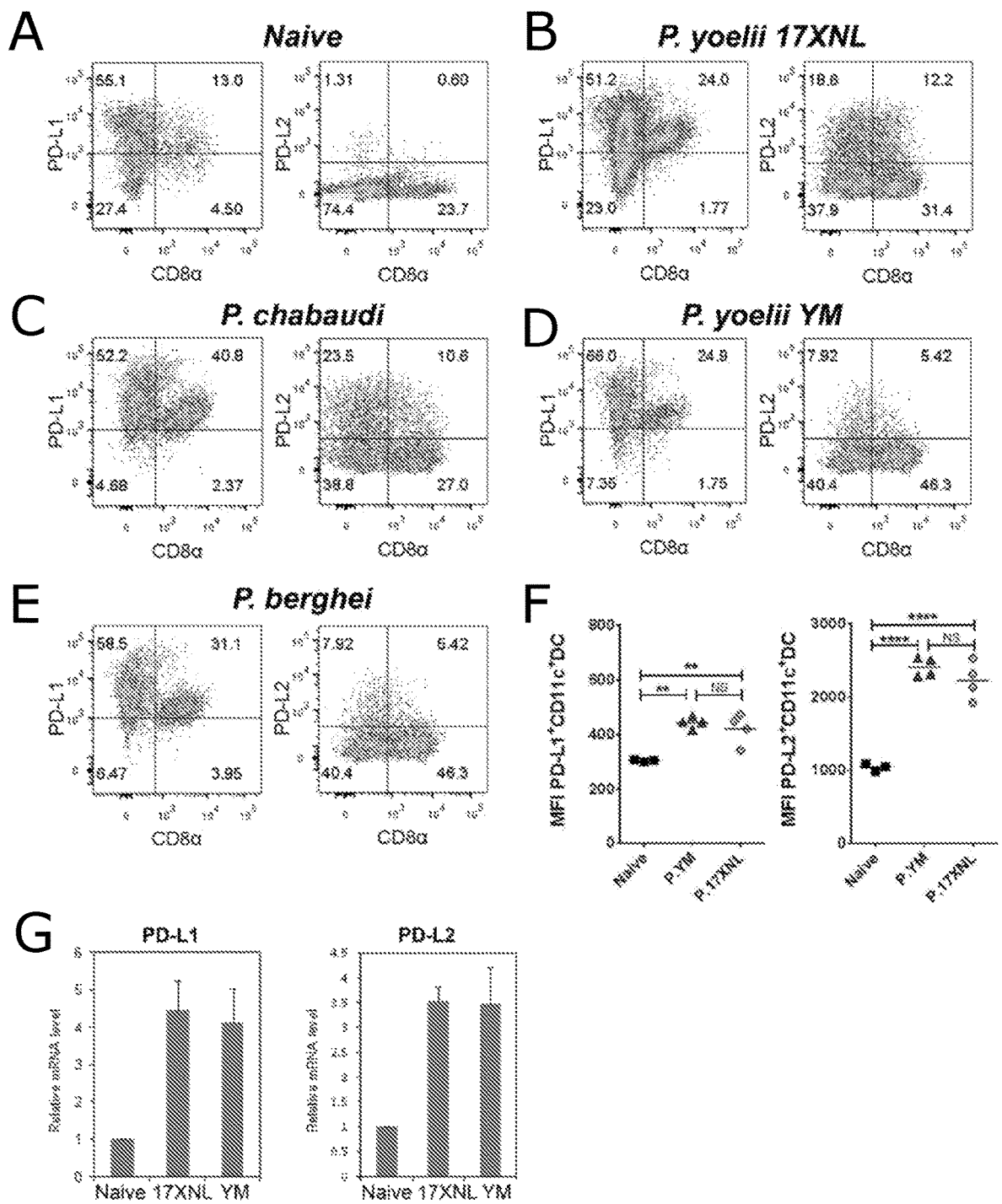
FIG. 4 is a graphical representation showing PD-L1 and PD-L2 expression levels on DCs from lethal and non-lethal malaria. (A)-(E) Flow cytometric profiles of PD-L1, PD-L2 and CD8 expression on viable CD19$^-$ CD3$^-$ D11c$^+$ DCs from (A) naïve mice and mice infected with malaria strains (B) non-lethal $P.$ $yoelii$ 17XNL or (C) non-lethal $P.$ $chabaudi$ (D) lethal $P.$ $yoelii$ YM or (E) lethal $P.$ $berghei$. (F) Repeat experiment for MFI of CD11c$^+$ spleen DCs from naive and infected mice (seven days post infection) expressing PD-L1 and PD-L2, measured on a different flow cytometer with different voltage settings to that used in FIGS. 3B and D. (G) Quantitative RT-PCR analysis of PD-L1 and PD-L2 from RNA isolated from DCs (naïve or infected with $P.$ $yoelii$ 17XNL and YM at day seven). Results are normalised to the geometric mean of three housekeeping genes (CxxC1, TBP and mRPL13A). Values are expressed as mean±SEM of three independent experiments, and expressed relative to results from uninfected mice.

Given that PD-L2 expression was associated with survival from malaria, the inventors next examined how PD-L2 co-expression with PD-L1 on DCs could modulate immunity. A previous study showed that the interaction between PD-L1 on DCs and PD-1 on CD8$^+$ OTI T cells contributed to ligand-induced T cell receptor (TCR) down-modulation (Karwacz et al., *EMBO. Mol. Med.* 3: 581-592, 2011). Experiments were conducted to investigate if PD-L2 co-expression with PD-L1 on DCs could inhibit PD-L1-mediated down-regulation of TCRs and inducible T-cell co-stimulator (ICOS) expression. To do so, purified DCs and T cells were cultured from infected mice (1:5 cells), with antibodies to block PD-1, PD-L1 or PD-L2 functions and examined the T cells after 36 hours for high expression of CD3, a component of the TCR, and high ICOS expression which can indicate T cell activation (FIGS. 9I-9N). Blockade of PD-1-signalling to T cells with anti-PD-1 antibody in the DC: T cell cultures significantly increased the expression of CD3 and ICOS, indicating PD-1 signals down-regulated expression of these molecules on T cells (FIGS. 4K 9K and 9N). When PD-L1 signals were blocked with antibody, leaving only PD-L2 to function, T cells had significantly increased levels of ICOS and CD3 (FIGS. 9L and 9N). In contrast, when PD-L2 was blocked, leaving PD-L1 function intact, there was a significant loss of CD3 and ICOS (FIGS. 9M and 9N). Overall, these findings show that in the context of cells from *P. yoelii* 17XNL-infected mice, PD-L1 expression on DCs is likely to inhibit T cell activation, whilst PD-L2 appears to promote CD3 and ICOS expression.

Materials and Methods

DC Transfer Study

CD11c$^+$ DC obtained from spleens of wt and PD-L 1 ko mice infected with 10$^4$ *P. yoelii* YM (lethal) pRBC. Four days post infection, mice were treated with 250 μg Pyrimethamine daily for four days to clear the infection. At day 7, the spleens were digested and DC enriched using Dynal DC enrichment kit. Samples were run on the AutoMACs to remove residual Dynal labeled cells and hemozoin. Highly purified DCs were obtained by labelling DCs with anti-CD11c MACS beads and isolated on AutoMACS. Approximately 1.5×10$^7$ DC were then transfused intravenously to naive mice. After resting the mice for greater than 15 hours, they were infected with a lethal dose of *P. yoelii* YM (10$^4$ pRBC). Mice were followed for 48 days when monitoring was stopped.

DC-T Cell Culture

Mice were infected with 10$^5$ *P. yoelii* 17XNL pRBC and on day 14 post infection, the spleens were digested and total T cells were isolated using CD90.2 MACS beads, to minimize any effect on the TCR. DCs were then isolated from remaining spleen cells using Dynal DC enrichment kit.

Approximately 10$^6$ T cells were cultured with 2×10$^9$ DCs in at least triplicate wells. Control or blocking anti-PD-1 (RMP1-14), anti-PD-L1 (10F.9G2) or anti-PD-L2 (TY25) antibodies were added to cultures at a concentration of 20 μg/ml. After 36 hours culture, cells were washed and labeled for flow cytometry. CD3 and ICOS expression was assessed on viable CD$^{4+}$ CD62L$^{Lo}$PD-1$^+$ T cells.

Example 6

Pd-L2 Expression on DCs from Patients with Metastatic Cancer

Figure 10:
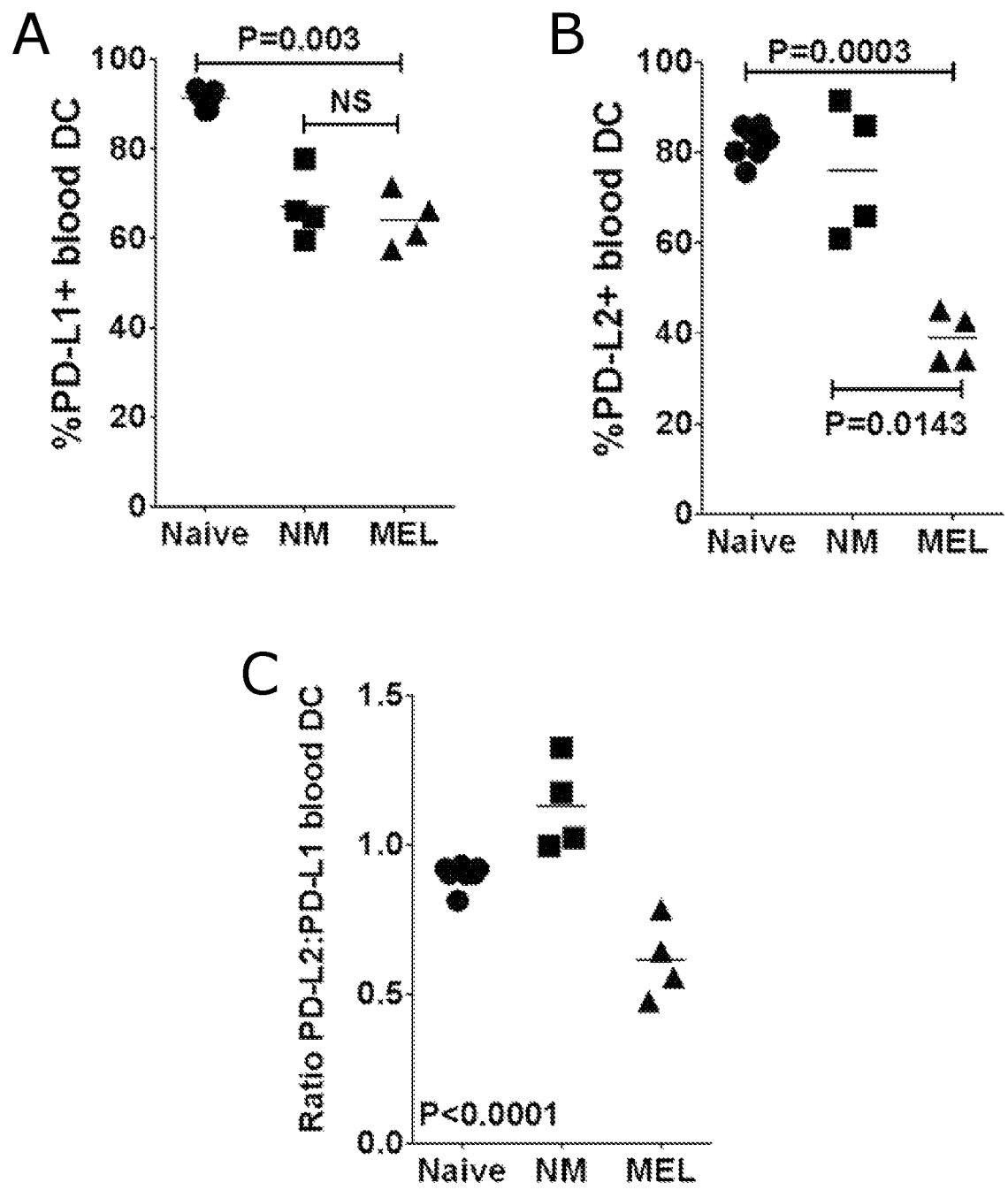
FIG. 10 is a graphical representation showing that PD-L2 expression on blood DCs is reduced in patients with metastatic melanomas. (A-C) Blood was taken from eight healthy human volunteers, four patients with non-melanoma lesions and four patients with metastatic melanomas. Their blood was examined for percentage of CD11c$^+$ DC expressing (A) PD-L1 and (B) PD-L2. (C) Plot showing ratio of % PD-L2: % PD-L1 DCs in each group. The P value for (A) and (B) used Mann Whitney test between each group and (C) was calculated by Kruskal-Wallis multiple comparison test.

To provide additional proof of concept data, blood DCs from patients with either benign lesions or metastatic melanoma were compared. A significant loss of PD-L2$^+$ DCs was observed in patients suffering from metastatic disease (see, FIG. 10). While healthy volunteers have a ratio of % PD-L2:% PD-L1 of around 0.9, this ratio drops to between 0.4 to 0.8 during metastatic melanoma. Interestingly, in patients with localized lesions (i.e., benign tumours), the % PD-L2:% PD-L1 ratio increases to between 0.9 and 1.3.

Based on the findings with systemic malaria and cancer, it appears that PD-L2, but not PD-L1 predicts the severity of Th immune response-associated systemic disease. Overall, it is predicted that PD-L2 levels increase during autoimmune disease, which drives expansion of damaging immune effector cells. This is reflected by patients with local lesions having a higher ratio.

Example 7

Pd-L2 Multimerization is Indicative of Th1 Immune Status

The present inventors hypothesized that a multimeric soluble PD-L2 (sPD-L2) would outcompete PD-L1 for binding to PD-1 on Th1 cells and thus reduce the suppressive effects of PD-L1 on T cell functions. To test this, a plasmid construct containing the extracellular domain of mouse PD-L2 fused to the Fc part of human IgG was generated and transfected into mammalian cells by Geneart (Life Technologies; Germany). The soluble dimeric PD-L2 Ig protein (PD-L2) was purified from culture supernatants using Protein G columns. This protein was shown to have <0.2EU/mL endotoxin. PD-L2 was multimerized by biotinylating dimeric PD-L2 with EZ-link-sulpho-NHS Biotin according to manufacturer's instructions to get 2-5 biotin molecules per PD-L2 dimer as measured by kit to measure the level of biotinylation (Pierce, US). Excess biotin was removed by passing the protein through PD-10 columns. The biotinylated PD-L2 was mixed with streptavidin (Cedarlane, US) at a 4:1 molar ratio to yield a multimeric PD-L2 chimeric polypeptide that was largely in octameric form. Each batch of Streptavidin was tested by a protein assay as the amount provided in the vial was in excess to the purchased amount. The ratio was optimized for each batch of Streptavidin as each batch can have different activities (e.g., 6:1). Western blot studies with a low percentage native SDS-PAGE gel confirmed that protein was multimerized as octamers with bands around 300-400 kDa.

Next, wild-type mice were infected with lethal *P. yoelii* YM or *P. berghei* and administered PD-L2 on day 3, after parasitemia(s) were measurable and then on days 5 and 7 post-infection. All wild-type mice infected with *P. yoelii* YM and treated with control human IgG (Control Ig) died or had to be euthanized within ten days (FIG. 11A-C).

Figure 11:
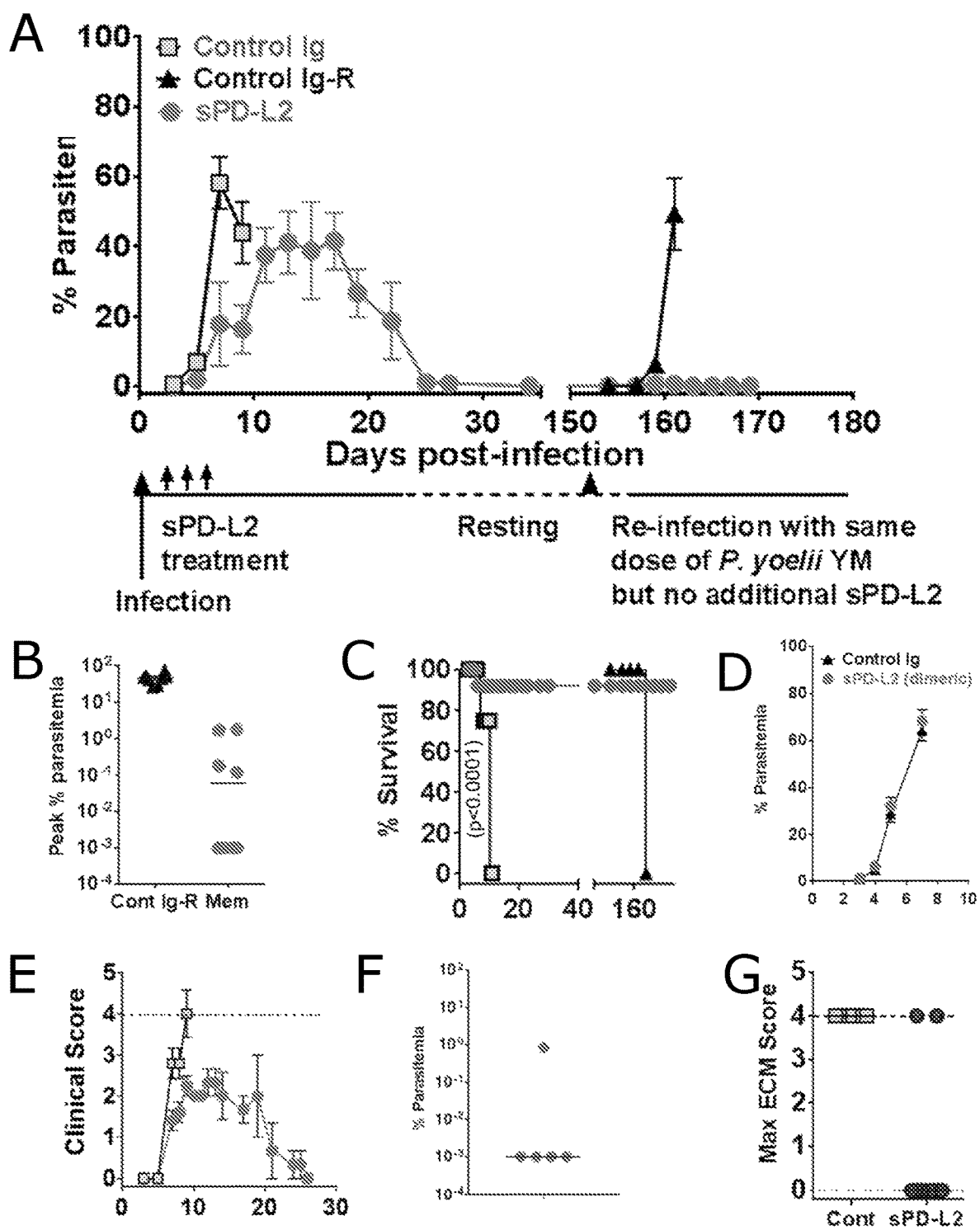
FIG. 11 is a graphical representation showing that an octameric form of PD-L2 protects against lethal malaria. (A) Mean percent parasitemia; (B) log-scale showing number of mice with parasitemia; (C) survival (x-axis showing number days post infection); (D) Percentage parasitemia for a typical course of *P. yoelii* YM malaria in wild-type mice treated with negative control (human) IgG or dimeric PD-L2 on days 3, 5 and 7 post infection, and (E) clinical symptom scores (x-axis showing number days post infection) for a typical course of *P. yoelii* YM malaria in wild-type mice treated with control (human) IgG or PD-L2 after detectable parasitemia, on day 3 and then days 5 and 7 (total n=12, from three independent experiments). All surviving mice were rested and after 150 days, rechallenged with the same dose of lethal *P. yoelii* YM malaria (no additional PD-L2 was administered) along with new age-matched control mice (control Ig-R). (F) Peak percent parasitemia in naïve mice given 200 μL blood from PD-L2-treated mice, 20 days after rechallenge with *P. yoelii* YM (x-axis showing number days post infection). This assay detects low numbers of parasite in the blood of donor mice. (G) Clinical symptom scores, (H) survival (x-axis showing number days post infection), and (I) mean percent parasitemia (x-axis showing number days post infection) for a typical course of *P. berghei* infection in wild-type mice treated with control (human) IgG or PD-L2 on days 3, 5 and 7 post-infection (total n=9 from two independent experiments). Error bars represent SEM. Significance of survival was analysed using Log-rank (Mantel-Cox) test.
Figure 11:
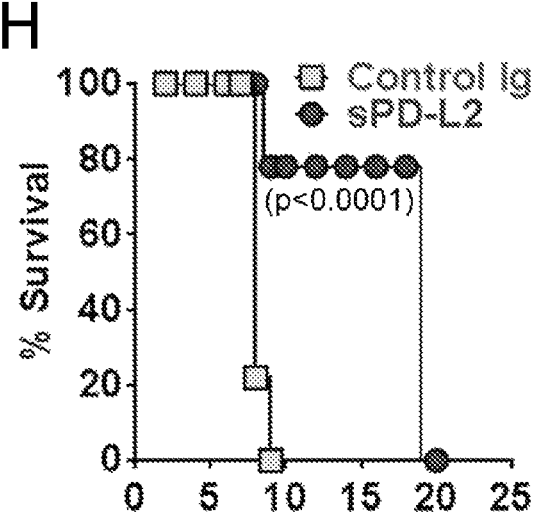
Figure 11:
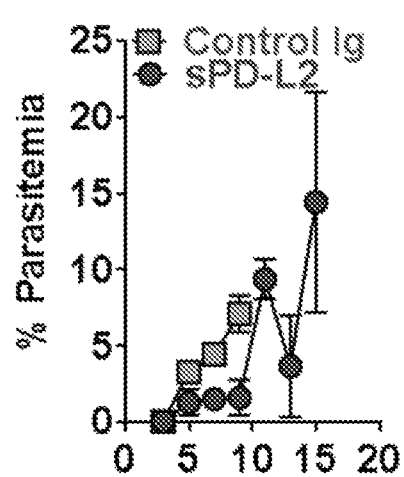

Similarly, dimeric PD-L2 did not offer any protection from increasing parasitemia (FIG. 11D). In contrast, 92% of *P. yoelii* YM-infected mice (n=12) treated with PD-L2 survived and cleared the infection in 25 days with fewer symptoms (FIG. 11A-E). All of the surviving mice were rested until day 150 and re-challenged with the same dose of lethal *P. yoelii* YM malaria (no additional PD-L2 was administered; FIG. 11A) along with new age-matched, naïve control mice (Control Ig-R). All of the mice previously treated with PD-L2 survived re-infection with no symptoms, and only 4 out of 8 mice showed any parasitemia, as shown by a log scale in the FIG. 11B. Within 20 days of re-infection, 80% of these sPD-L2-treated, re-infected mice had completely cleared the infection, as the transfer of 200 μl of blood from these mice to naïve mice did not transfer the infection (FIG. 11F). In comparison, the second set of age-matched control mice succumbed to the infection, confirming the lethality of the parasite used for re-infections (FIG. 11C). Overall, multimeric PD-L2 could overcome PD-L1 mediated lethality following infection with *P. yoelii* YM.

Likewise, 100% of control mice infected with *P. berghei* developed experimental cerebral malaria symptoms (ECM) within 8 days (FIG. 11G) and succumbed to the infection by day 10 (FIG. 11H). Only 22% of the *P. berghei*-infected mice treated with sPD-L2 developed cerebral malaria as seen by their ECM scores (FIG. 11G). Furthermore, the surviving mice controlled the infection for approximately 20 days (FIGS. 11H and I), before succumbing 13 days after the last dose of PD-L2. Additional doses did not improve survival (data not shown). In summary, the administration of multimeric PD-L2 significantly improved survival from lethal infections and reduced the severity of the clinical symptoms, especially for cerebral malaria.

Example 8

Dodecameric Pd-L2 Enhances Immune Response to Tumors

A soluble chimeric PD-L2 polypeptide was designed that self-assembles into dodecamers. This chimeric polypeptide contains the extracellular domain of mouse PD-L2 fused to the Fc portion of human IgG as well as a C-terminal α-tail piece (mouse PD-L2-Fc-atp) and has the following amino acid sequence:

[SEQ ID NO: 58]
MLLLLPILNLSLQLHPVAALftvtapkevytvdvgssyslecdfdrrecte legiraslqkvendtslqseratlleeqlplgkalfhipsvqvrdsgqyrc lvicgaawdykyltvkvkasymridtrilevpgtgevqltcqargyplaev swqnvsvpantshirtpeglyqvtsvlrlkpqpsrnfscmfwnahmkelts aiidplsrmepkvprtw*plhvfipac*DKTHTCPPCPAPELLGGPSVFLFPP

KPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGKPT

HVNVSVVMAEVDGTCY.

The sequence in uppercase and underlined font represents the amino acid sequence of mouse PD-L2 signal peptide; the sequence in lowercase font corresponds to the amino acid sequence of mouse PD-L2 ectodomain; the sequence in italicized lowercase font represents the amino acid sequence of a portion of the mouse PD-L2 transmembrane domain; the sequence in uppercase font corresponds to the amino acid sequence of an Fc polypeptide for human IgG1; and the sequence in bold uppercase font represents the amino acid sequence of the alpha tailpiece (atp) of an IgA molecule.

A construct expressing a DNA sequence encoding the chimeric polypeptide was transfected into proprietary mammalian cells by Geneart (Life Technologies; Germany) and the soluble largely dodecameric PD-L2-Ig protein (sPD-L2) was purified from culture supernatants using Protein G columns column and then FPLC fractionation to exclude dimeric forms of the protein. This protein was shown to have <0.2EU/mL endotoxin.

Next, established B16.F0 and B16.F10 melanoma cell lines were grown in the laboratory and C57BL/6 mice implanted with $5 \times 10^5$ or $1 \times 10^5$ cells, subcutaneously, respectively.

Figure 12:
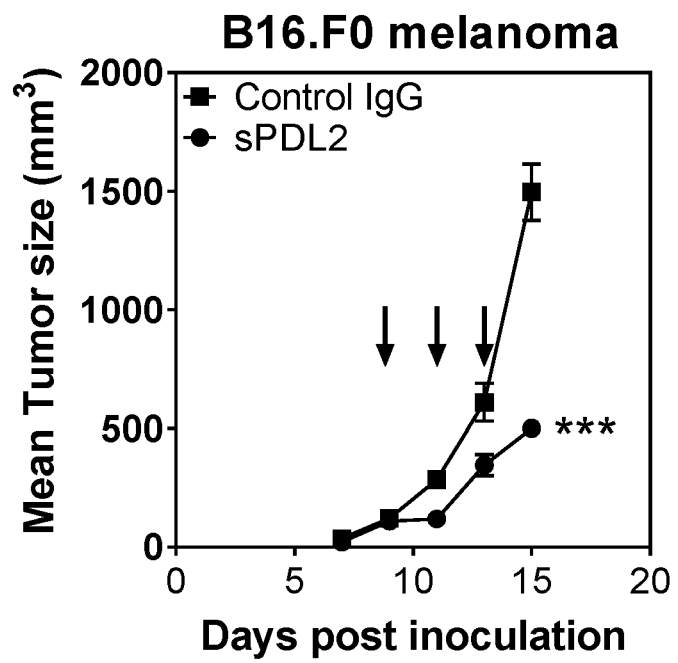
FIG. 12 a graphical representation showing protection of soluble dodecameric PD-L2 (sPD-L2) against advanced melanomas. Groups of six C57BL/6 mice were implanted subcutaneously with 5×10$^5$ B16.F0 melanoma cells. Around day 9, when the average tumor size was ~100 mm$^3$, mice were given either 200 μg human IgG or sPD-L2 on days 9, 11 and 13 and tumor size monitored every 1-2 days. Data represent pooled one of two independent experiments in which similar results were obtained. P values were determined using the non-parametric Mann-Whitney U test based on 1-sided tail. (***p=0.0006 are for comparisons between groups).

To determine the effects of sPD-L2 on advanced melanomas, when the B16.F0 tumours reached 100 mm³ volumes around day 9, mice were given either 200 μg human IgG or sPD-L2 on days 9, 11 and 13 and tumor size monitored every 1-2 days. For ethical reasons, mice were euthanized if tumors were >1000 mm³, or showed any ulceration or symptoms of discomfort. The results from this study, which are presented in FIG. 12, clearly show that sPD-L2 enhances the immune response to and protects against advanced melanomas.

Figure 13:
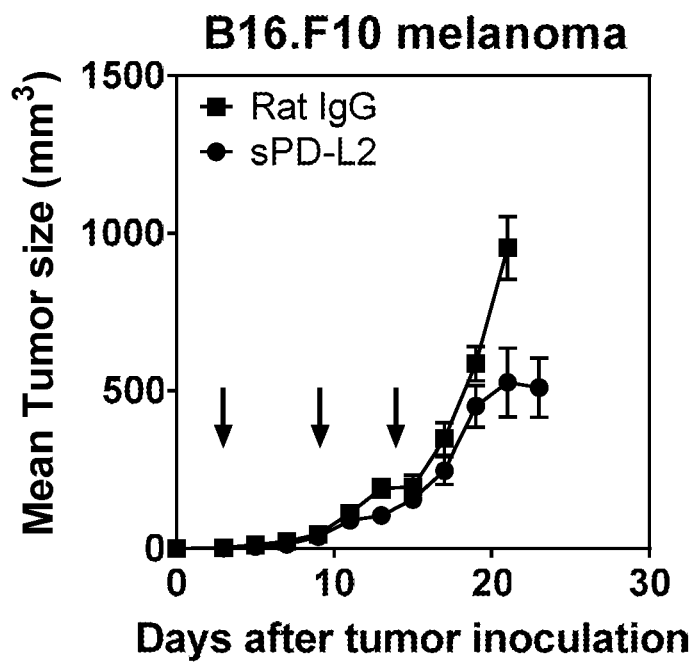
FIG. 13 a graphical representation showing early protection against melanomas by sPD-L2. Groups of six C57BL/6 mice were implanted subcutaneously with 1×10⁵ B16.F10 melanoma cells. Around day 9, when the average tumor size was ~100 mm³, mice were given either 200 μg human IgG or sPD-L2 on days 3, 9 and 15 and tumor size monitored every 1-2 days. Data represent pooled one of two independent experiments in which similar results were obtained. P values were determined using the non-parametric Mann-Whitney U test based on 1-sided tail. (***p=0.03 are for comparisons between groups).

The effect of sPD-L2 was also investigated on early tumors. In these experiments, B16.F10 cells were implanted at around day 3, when tumors reached ~50 mm³ volumes, and mice were treated with either 200 μg human IgG or sPD-L2 on days 3, 9 and 15. The results from this study (see, FIG. 13) revealed that sPD-L2 provides early protection against melanomas.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A polypeptide complex that is represented by formula (I):

[P]$_n$ (I)

wherein:

P, independently for each occurrence, represents a proteinaceous molecule consisting essentially of a single polypeptide chain consisting of a PD-L2 polypeptide, an optional peptide linker and at least one oligomerization domain, wherein the at least one oligomerization domain is other than an Fc domain with affinity for an Fc receptor; and n is in the range of 4 to 12; and wherein oligomerization domains of different proteinaceous molecules of the complex are complementary with one another to facilitate association of the oligomerization domains and oligomerization of the proteinaceous molecules.

2. The polypeptide complex of claim 1, wherein the proteinaceous molecule lacks one or both of a PD-L2 transmembrane domain and a PD-L2 cytoplasmic domain.

3. The polypeptide complex of claim 1, wherein n is 5 or 6.

4. The polypeptide complex of claim 1, wherein the at least one oligomerization domain is operably connected upstream and/or downstream of the PD-L2 polypeptide.

5. The polypeptide complex of claim 1, wherein the proteinaceous molecule comprises a single polypeptide chain represented by formula (II):

$$PD\text{-}L2\text{-}L\text{-}OMD_A \qquad (II)$$

wherein:
PD-L2 represents a PD-L2 polypeptide;
$OMD_A$ is an oligomerization domain that forms oligomers $(OMD_A)_i$ of i subunits $OMD_A$, wherein i is in the range of 4 to 6; and
L is a bond or a peptide linker.

6. The polypeptide complex of claim 1, wherein the proteinaceous molecule comprises a single polypeptide chain represented by formula (III):

$$PD\text{-}L2\text{-}L\text{-}OMD_A\text{-}L\text{-}OMD_B \qquad (III)$$

wherein:
$OMD_A$ is an oligomerization domain that forms oligomers $(OMD_A)_i$ of i subunits $OMD_A$, wherein i is $\geq 2$;
L, independently for each occurrence, represents a bond or a peptide linker; and
$OMD_B$ is an oligomerization domain that forms oligomers $(OMD_B)_j$ of j subunits $OMD_B$, wherein j is an integer greater than i.

7. The polypeptide complex of claim 1, wherein the proteinaceous molecule comprises a single polypeptide chain represented by formula (IV):

$$OMD_A\text{-}L\text{-}PD\text{-}L2 \qquad (IV)$$

wherein:
$OMD_A$ is an oligomerization domain that forms oligomers $(OMD_A)_i$ of i subunits $OMD_A$, wherein i is in the range of 4 to 6;
L is a bond or a peptide linker; and
PD-L2 represents a PD-L2 polypeptide.

8. The polypeptide complex of claim 1, wherein the proteinaceous molecule comprises a single polypeptide chain represented by formula (V):

$$OMD_B\text{-}L\text{-}OMD_A\text{-}L\text{-}PD\text{-}L2 \qquad (V)$$

wherein:
$OMD_B$ is an oligomerization domain that forms oligomers $(OMD_B)_j$ of j subunits $OMD_B$, wherein j is $\geq 2$;
L, independently for each occurrence, represents a bond or a peptide linker; and
$OMD_A$ is an oligomerization domain that forms oligomers $(OMD_A)_i$ of i subunits $OMD_A$, wherein i is an integer greater than j; and
PD-L2 represents a PD-L2 polypeptide.

9. The polypeptide complex of claim 1, wherein the at least one oligomerization domain is selected from dimerization domains, trimerization domains, tetramerization domains, pentamerization domains and hexamerization domains.

10. A nucleic acid construct that comprises a coding sequence for a proteinaceous molecule, operably connected to a regulatory element that is operable in a host cell, wherein the proteinaceous molecule-consists essentially of a single polypeptide chain consisting of a PD-L2 polypeptide, an optional peptide linker and at least one oligomerization domain that facilitates self-assembly of the proteinaceous molecule to form a polypeptide complex represented by formula (I)

$$[P]_n \qquad (I)$$

wherein:
P, independently for each occurrence, represents the proteinaceous molecule, and wherein n is in the range from 4 to 12;
the at least one oligomerization domain is other than an Fc domain with affinity for an Fc receptor; and
oligomerization domains of different proteinaceous molecules of the complex are complementary with one another to facilitate association of the oligomerization domains and oligomerization of the proteinaceous molecules.

11. A host cell that contains the nucleic acid construct of claim 10.

12. An immune-modulating composition comprising the polypeptide complex of claim 1, and a pharmaceutically acceptable carrier, diluent or adjuvant.

13. A method of stimulating, eliciting or augmenting an immune response, including a Th1 immune response, in a subject, wherein the method comprises administering to the subject the polypeptide complex of claim 1 or composition of claim 12.

14. A method for treating a Th1-related disease or disorder in a subject, the method comprising administering to the subject an effective amount of polypeptide complex of claim 1 or composition of claim 12, wherein the Th1-related disease or disorder is a cancer or a pathogenic infection.

15. The method of claim 13, wherein the polypeptide complex or composition is administered to a subject when the subject is identified as having impaired Th1 immunity by a method comprising: (1) determining a Th1 immune status biomarker profile of a sample obtained from the subject, wherein the Th1 immune status biomarker profile comprises a first biomarker value that is at least partially indicative of an amount of a first Th1 immune status biomarker and a second biomarker value that is at least partially indicative of an amount of a second Th1 immune status biomarker in the sample, wherein the first and second Th1 immune status biomarkers are biomarkers on antigen-presenting cells (APCs), wherein the first Th1 immune status biomarker is programmed cell death protein 1 ligand 2 (PD-L2) and the second Th1 immune status biomarker is programmed cell death protein 1 ligand 2 (PD-L1); and (2) determining the indicator using the first and second biomarker values, the indicator being indicative of a sample PD-L2:PD-L1 biomarker value ratio that is at least partially indicative of the subject's Th1 immune status, wherein the indicator is determined to be at least partially indicative of impaired Th1 immunity in the subject if the sample PD-L2:PD-L1 biomarker value ratio is reduced relative to a control PD-L2:PD-L1 biomarker value ratio that correlates with the presence of normal or unimpaired Th1 immunity, wherein the indicator is determined to be at least partially indicative of elevated Th1 immunity in the subject if the sample PD-L2:PD-L1 biomarker value ratio is increased relative to a control PD-L2:PD-L1 biomarker value ratio that correlates with the presence of normal or unimpaired Th1 immunity, and wherein the indicator is determined to be at least partially indicative of normal or unimpaired Th1 immunity in the subject if the sample PD-L2:PD-L1 biomarker value ratio is about the same as a control PD-L2:PD-L1 biomarker value ratio that correlates with the presence of normal or unimpaired Th1 immunity.

16. The method of claim 15, wherein the APCs are selected from the group consisting of dendritic cells and macrophages.

17. The method of claim 15, wherein the APCs comprise CD11c-expressing dendritic cells.

18. The method of claim 15, wherein a respective biomarker value is at least partially indicative of a concentration of a corresponding Th1 immune status biomarker in the sample obtained from the subject.

19. The method of claim 15, wherein a respective biomarker value includes the abundance of a corresponding Th1 immune status biomarker.

20. The method of claim 15, wherein an individual biomarker value includes the percentage of APCs that express a corresponding Th1 immune status biomarker on the cell surface.

21. The method of claim 15, wherein a respective biomarker value is a measurement of PD-L2 clustering on the surface of the APCs.

* * * * *